(12) United States Patent
Horner et al.

(10) Patent No.: US 11,234,754 B2
(45) Date of Patent: *Feb. 1, 2022

(54) SMOKE EVACUATION DEVICE

(71) Applicant: Megadyne Medical Products, Inc., Draper, UT (US)

(72) Inventors: Shawn K. Horner, Woods Cross, UT (US); Jason L. Harris, Lebanon, OH (US); Frederick Shelton, Hillsboro, OH (US); Chad S. Frampton, American Fork, UT (US); Steven D. Andrews, West Jordan, UT (US); Benjamin J. Danziger, Seattle, WA (US); Mark D. Glassett, Sandy, UT (US); Darcy W. Greep, Herriman, UT (US); Roger Millis, West Jordan, UT (US); David C. Yates, West Chester, OH (US)

(73) Assignee: Megadyne Medical Products, Inc., Draper, UT (US)

( * ) Notice: Subject to any disclaimer, the term of this patent is extended or adjusted under 35 U.S.C. 154(b) by 715 days.

This patent is subject to a terminal disclaimer.

(21) Appl. No.: 15/826,376

(22) Filed: Nov. 29, 2017

(65) Prior Publication Data

US 2019/0159830 A1     May 30, 2019

(51) Int. Cl.
*A61B 18/14*     (2006.01)
*A61M 1/00*     (2006.01)
(Continued)

(52) U.S. Cl.
CPC .............. *A61B 18/1402* (2013.01); *A61B 2018/00017* (2013.01); *A61B 2018/00702* (2013.01);
(Continued)

(58) Field of Classification Search
CPC ......... A61B 18/14; A61M 1/00; A61M 27/00; A61F 13/00; A61F 13/02; A61K 9/22
See application file for complete search history.

(56) References Cited

U.S. PATENT DOCUMENTS

| 1,165,288 A | 12/1915 | Rimmer |
| 1,789,194 A | 1/1931 | Rockwell |

(Continued)

FOREIGN PATENT DOCUMENTS

| CN | 204312376 U | * 5/2015 |
| GB | 2117982 | 10/1983 |

(Continued)

OTHER PUBLICATIONS

Non-Final Office Action for U.S. Appl. No. 15/826,287 dated Jul. 17, 2019.

(Continued)

*Primary Examiner* — Michele M Kidwell
*Assistant Examiner* — Ilya Y Treyger
(74) *Attorney, Agent, or Firm* — Workman Nydegger

(57) ABSTRACT

A smoke evacuation device that evacuates smoke from a surgical site and filters the smoke from the air. The smoke evacuation device can include a fluid trap for removing moisture from the smoke. The smoke evacuation device can also include a filter with a compression mechanism for compressing a filter medium. The smoke evacuation device can also include features for controlling flow parameters, noise, and vibrations of the device. A remote activation device can also be used to activate the smoke evacuation device upon detection of certain system parameters.

20 Claims, 49 Drawing Sheets

(51) Int. Cl.
  *A61M 27/00* (2006.01)
  *A61F 13/00* (2006.01)
  *A61F 13/02* (2006.01)
  *A61K 9/22* (2006.01)
  *A61B 90/00* (2016.01)
  *A61B 18/00* (2006.01)

(52) U.S. Cl.
  CPC .............. *A61B 2018/00827* (2013.01); *A61B 2090/034* (2016.02); *A61B 2218/008* (2013.01)

(56) References Cited

U.S. PATENT DOCUMENTS

| | | | |
|---|---|---|---|
| 2,577,606 A | 12/1951 | Conley | |
| 3,815,752 A | 6/1974 | Hoffman et al. | |
| 3,841,490 A | 10/1974 | Hoffman et al. | |
| 4,116,649 A | 9/1978 | Cullen et al. | |
| 4,157,234 A | 6/1979 | Shaffer et al. | |
| 4,396,206 A | 8/1983 | Tsuge et al. | |
| 4,619,672 A | 10/1986 | Robertson | |
| 4,642,128 A * | 2/1987 | Solorzano | A61B 18/00 340/607 |
| D291,353 S | 8/1987 | Conero | |
| 4,701,193 A | 10/1987 | Robertson et al. | |
| 4,786,298 A | 11/1988 | Billet et al. | |
| 4,788,298 A | 11/1988 | Wang | |
| 4,810,269 A | 3/1989 | Stackhouse et al. | |
| 4,826,513 A | 5/1989 | Stackhouse et al. | |
| 4,986,839 A | 1/1991 | Wertz et al. | |
| 4,988,839 A | 1/1991 | Kennicott | |
| D315,410 S | 3/1991 | Aten | |
| 5,108,389 A | 4/1992 | Comescu | |
| 5,144,176 A | 9/1992 | Popper | |
| 5,144,178 A | 9/1992 | Sugiura | |
| 5,160,334 A | 11/1992 | Billings et al. | |
| 5,221,192 A | 6/1993 | Heflin et al. | |
| 5,226,939 A | 7/1993 | Nicolas et al. | |
| 5,228,939 A | 7/1993 | Chu | |
| 5,242,474 A | 9/1993 | Herbst et al. | |
| 5,288,469 A | 2/1994 | Skalla et al. | |
| 5,288,489 A | 2/1994 | Reich et al. | |
| 5,318,516 A | 6/1994 | Comescu | |
| 5,336,218 A | 8/1994 | Linhares | |
| 5,342,349 A | 8/1994 | Kaufman | |
| D357,738 S | 4/1995 | Kaufman | |
| 5,423,779 A | 6/1995 | Yeh | |
| 5,431,650 A | 7/1995 | Comescu | |
| 5,456,248 A | 10/1995 | Holian et al. | |
| 5,507,859 A | 4/1996 | Kaiser | |
| 5,522,808 A | 6/1996 | Skalla | |
| 5,597,385 A | 1/1997 | Moerke | |
| 5,619,992 A | 4/1997 | Guthrie et al. | |
| 5,620,441 A | 4/1997 | Greff et al. | |
| 5,674,219 A | 10/1997 | Monson et al. | |
| 5,690,480 A | 11/1997 | Suzuki et al. | |
| 5,853,410 A | 12/1998 | Greff et al. | |
| 5,874,052 A | 2/1999 | Holland | |
| 5,910,291 A | 6/1999 | Skalla et al. | |
| 5,947,694 A | 9/1999 | Hablanian | |
| 5,992,413 A | 11/1999 | Martin et al. | |
| D420,140 S | 2/2000 | Noble | |
| 6,050,792 A | 4/2000 | Shaffer | |
| 6,089,527 A | 7/2000 | Utterberg | |
| 6,110,259 A | 8/2000 | Schultz et al. | |
| 6,129,530 A | 10/2000 | Shaffer | |
| 6,145,509 A | 11/2000 | Tanner | |
| 6,203,590 B1 | 3/2001 | Byrd | |
| 6,203,762 B1 | 3/2001 | Skalla et al. | |
| 6,331,246 B1 | 12/2001 | Beckham | |
| 6,439,864 B1 | 8/2002 | Shaffer | |
| D467,654 S | 12/2002 | Klug et al. | |
| 6,511,308 B2 | 1/2003 | Shaffer | |
| 6,524,307 B1 | 2/2003 | Palmerton et al. | |
| 6,544,210 B1 | 4/2003 | Trudel et al. | |
| 6,585,791 B1 | 7/2003 | Garito et al. | |
| 6,589,316 B1 | 7/2003 | Schultz et al. | |
| 6,589,318 B2 | 7/2003 | El-Shoubary et al. | |
| 6,592,543 B1 | 7/2003 | Wortrich et al. | |
| 6,616,722 B1 | 9/2003 | Cartellone | |
| 6,663,698 B2 * | 12/2003 | Mishin | B01D 46/0005 55/320 |
| D485,339 S | 1/2004 | Klug | |
| 6,709,248 B2 | 3/2004 | Fujioka et al. | |
| 6,736,620 B2 | 5/2004 | Satoh | |
| 6,758,885 B2 | 7/2004 | Leffel et al. | |
| 6,786,707 B2 | 9/2004 | Kim | |
| D513,314 S | 12/2005 | Iddings | |
| 7,014,434 B2 | 3/2006 | Fujioka et al. | |
| D521,137 S | 5/2006 | Khalil | |
| D545,955 S | 7/2007 | Arlas | |
| 7,258,712 B2 | 8/2007 | Schultz et al. | |
| D553,228 S | 10/2007 | Virr | |
| 7,276,052 B2 | 10/2007 | Kobayashi et al. | |
| D555,803 S | 11/2007 | Galrto | |
| 7,294,116 B1 | 11/2007 | Ellman et al. | |
| D568,991 S | 5/2008 | Schweikert | |
| D574,323 S | 8/2008 | Waaler | |
| 7,465,156 B2 | 12/2008 | Lee | |
| 7,497,340 B2 | 3/2009 | Hershberger et al. | |
| 7,597,731 B2 | 10/2009 | Palmerton | |
| D608,447 S | 1/2010 | Meyer | |
| D616,986 S | 6/2010 | Biegen | |
| D625,399 S | 10/2010 | Horiguchi | |
| D626,204 S | 10/2010 | Morgan | |
| 7,819,957 B2 | 10/2010 | Roberts et al. | |
| 7,942,655 B2 | 5/2011 | Shaffer | |
| D646,368 S | 10/2011 | Osendorf et al. | |
| 8,033,798 B2 | 10/2011 | Suh et al. | |
| D648,841 S | 11/2011 | Lam | |
| 8,142,175 B2 | 3/2012 | Duppert et al. | |
| D657,468 S | 4/2012 | Held | |
| 8,147,577 B2 | 4/2012 | Palmerton et al. | |
| 8,190,398 B2 | 5/2012 | Kitaguchi et al. | |
| D666,704 S | 9/2012 | Osendorf | |
| 8,298,420 B2 | 10/2012 | Burrows | |
| 8,556,570 B2 | 10/2013 | Ishihara | |
| 8,608,816 B2 | 12/2013 | Palmerton et al. | |
| 8,684,705 B2 | 4/2014 | Magoon et al. | |
| 8,727,744 B2 | 5/2014 | Magoon et al. | |
| 8,974,569 B2 | 3/2015 | Matula | |
| 9,011,366 B2 | 4/2015 | Dean et al. | |
| 9,028,230 B2 | 5/2015 | Shaffer | |
| 9,067,030 B2 | 6/2015 | Stearns et al. | |
| 9,074,598 B2 | 7/2015 | Shaffer et al. | |
| D736,933 S | 8/2015 | Qiu | |
| D737,449 S | 8/2015 | Zheng | |
| D739,770 S | 9/2015 | Scampoli | |
| 9,199,047 B2 | 12/2015 | Stearns et al. | |
| 9,215,964 B2 | 12/2015 | Loske | |
| 9,215,984 B2 | 12/2015 | Hattery et al. | |
| 9,366,254 B2 | 6/2016 | Murakami | |
| 9,387,295 B1 | 7/2016 | Mastri et al. | |
| 9,387,296 B1 | 7/2016 | Mastri et al. | |
| D764,649 S | 8/2016 | Ko | |
| 9,415,160 B2 | 8/2016 | Bonano et al. | |
| 9,435,339 B2 | 9/2016 | Calhoun et al. | |
| 9,474,512 B2 | 10/2016 | Blackhurst et al. | |
| 9,532,843 B2 | 1/2017 | Palmerton | |
| 9,549,849 B2 | 1/2017 | Charles | |
| 9,579,428 B1 | 2/2017 | Reasoner et al. | |
| D783,178 S | 4/2017 | Mead | |
| D799,055 S | 10/2017 | Kennedy | |
| D802,024 S | 11/2017 | Aoki | |
| 9,867,914 B2 | 1/2018 | Bonano et al. | |
| 9,943,355 B2 | 4/2018 | Babini | |
| D868,287 S | 11/2019 | Frampton | |
| 10,631,916 B2 | 4/2020 | Maltese et al. | |
| D886,976 S | 6/2020 | Horner et al. | |
| D890,900 S | 7/2020 | Bink et al. | |
| 10,758,293 B2 | 9/2020 | Horner et al. | |
| 10,758,855 B2 | 9/2020 | Horner et al. | |
| 10,758,856 B2 | 9/2020 | Horner et al. | |
| D912,762 S | 3/2021 | Horner et al. | |
| 2004/0223859 A1 | 11/2004 | Sharp | |

(56) References Cited

U.S. PATENT DOCUMENTS

| | | |
|---|---|---|
| 2005/0000196 A1 | 1/2005 | Schultz |
| 2005/0189283 A1 | 9/2005 | Smit et al. |
| 2005/0263004 A1 | 12/2005 | Larsen et al. |
| 2006/0099096 A1 | 5/2006 | Shaffer et al. |
| 2006/0224150 A1 | 10/2006 | Arts et al. |
| 2007/0066970 A1 | 3/2007 | Ineson |
| 2009/0022613 A1 | 1/2009 | Dai et al. |
| 2010/0185139 A1 | 7/2010 | Stearns |
| 2011/0067699 A1 | 3/2011 | Caruso |
| 2011/0203585 A1 | 8/2011 | Cozean et al. |
| 2013/0023160 A1 | 1/2013 | Healey et al. |
| 2013/0231606 A1 | 9/2013 | Stearns et al. |
| 2013/0251514 A1 | 9/2013 | Oakman |
| 2014/0356207 A1 | 12/2014 | Yang |
| 2015/0133750 A1 | 5/2015 | White et al. |
| 2015/0224237 A1 | 8/2015 | Reasoner et al. |
| 2015/0273381 A1 | 10/2015 | Stoner et al. |
| 2016/0000494 A1 | 1/2016 | Comescu |
| 2016/0001102 A1 | 1/2016 | Huh |
| 2016/0169941 A1 | 6/2016 | Fukui |
| 2016/0287817 A1 | 10/2016 | Mastri et al. |
| 2016/0367266 A1 | 12/2016 | Palmerton et al. |
| 2017/0014557 A1 | 1/2017 | Minskoff et al. |
| 2017/0014560 A1 | 1/2017 | Minskoff et al. |
| 2017/0095603 A1 | 4/2017 | Cho |
| 2017/0165725 A1 | 6/2017 | Hersey et al. |
| 2017/0181768 A1 | 6/2017 | Galley |
| 2017/0181788 A1 | 6/2017 | Dastjerdi et al. |
| 2017/0274125 A1 | 9/2017 | Minskoff et al. |
| 2019/0001029 A1 | 1/2019 | Davie et al. |
| 2019/0159825 A1 | 5/2019 | Frampton et al. |
| 2019/0159826 A1 | 5/2019 | Horner et al. |
| 2019/0159827 A1 | 5/2019 | Horner et al. |
| 2019/0160409 A1 | 5/2019 | Horner et al. |
| 2019/0160410 A1 | 5/2019 | Horner et al. |
| 2019/0162186 A1 | 5/2019 | Frampton et al. |
| 2020/0214760 A1 | 7/2020 | Horner et al. |
| 2020/0324238 A1 | 10/2020 | Jones et al. |
| 2020/0353399 A1 | 11/2020 | Horner et al. |

FOREIGN PATENT DOCUMENTS

| | | |
|---|---|---|
| JP | 2016 148281 | 8/2016 |
| PL | 220 478 | 10/2015 |
| WO | 9408698 | 4/1994 |
| WO | 2016142690 | 9/2016 |
| WO | 201703712 | 1/2017 |
| WO | 2017066720 | 4/2017 |
| WO | 2017112684 | 6/2017 |
| WO | 2017177069 | 10/2017 |

OTHER PUBLICATIONS

Final Office Action for U.S. Appl. No. 15/826,287 dated Dec. 20, 2019.
Notice of Allowance for U.S. Appl. No. 15/826,287 dated Feb. 12, 2020.
International Search and Written Opinion for PCT/IB2018/059376 dated May 7, 2019.
International Search Report and Written Opinion for PCT/IB2018/059371 dated Feb. 15, 2019.
Non-Final Office Action for U.S. Appl. No. 29/627,788 dated Feb. 19, 2019.
Notice of Allowance for U.S. Appl. No. 29/627,788 dated Jul. 23, 2019.
Non-Final Office Action for U.S. Appl. No. 15/826,325 dated Aug. 1, 2019.
Notice of Allowance for U.S. Appl. No. 15/826,325 dated Dec. 26, 2019.
Notice of Allowance for U.S. Appl. No. 29/627,793 dated Feb. 21, 2020.
Non-Final Office Action for U.S. Appl. No. 15/826,342 dated Jul. 16, 2019.
Final Office Action for U.S. Appl. No. 15/826,342 dated Nov. 5, 2019.
Notice of Allowance for U.S. Appl. No. 15/826,342 dated Jan. 31, 2020.
Notice of Allowance for U.S. Appl. No. 15/826,342 dated Apr. 23, 2020.
International Search Report and Written Opinion for PCT/IB2018/059377 dated Mar. 6, 2019.
Non-Final Office Action for U.S. Appl. No. 15/826,344 dated Sep. 12, 2019.
Notice of Allowance for U.S. Appl. No. 15/826,344 dated Jan. 23, 2020.
Notice of Allowance for U.S. Appl. No. 15/826,344 dated Apr. 22, 2020.
International Search Report and Written Opinion for PCT/IB2018/059375 dated May 7, 2019.
Non-Final Office Action for U.S. Appl. No. 29/627,794 dated Jul. 10, 2019.
Non-Final Office Action for U.S. Appl. No. 29/627,794 dated Feb. 19, 2020.
Exam Report for MX/f/2018/001583 dated Jan. 20, 2020.
International Search Report and Written Opinion for PCT/IB2018/059378 dated May 10, 2019.
U.S. Appl. No. 16/825,998, filed Mar. 20, 2020.
U.S. Appl. No. 29/627,793, filed Nov. 29, 2017.
U.S. Appl. No. 29/627,794, filed Nov. 29, 2017.
Bovie 35 hour filter found online [Sep. 11, 2018]—http://www.boviemedical.com/smoke-shark-ii/.
"Megadyne Surgical Smoke Evacuation System found online [Sep. 11, 2018]—http://www.hcp-austria.com/Minivac%20Smoke%20Evacuators.html".
Non-Final Office Action for U.S. Appl. No. 29/627,793 dated Oct. 29, 2018.
Examiner Interview Summary received for U.S. Appl. No. 15/826,370, dated Nov. 27, 2020, 2 pages.
Non-Final Office Action Received for U.S. Appl. No. 15/826,370, dated Aug. 18, 2020, 24 pages.
Non-Final Office Action received for U.S. Appl. No. 16/825,998, dated Feb. 2, 2021, 9 pages.
Requirement for Restriction/Election received for U.S. Appl. No. 15/826,289, dated Dec. 15, 2020, 8 pages.
Non-Final Office Action received for U.S. Appl. No. 15/826,289, dated May 28, 2021, 12 pages.
Non-Final Office Action received for U.S. Appl. No. 16/937,000, dated Aug. 31, 2021, 8 pages.
Notice of Allowance received for U.S. Appl. No. 16/825,998, dated Apr. 6, 2021, 9 pages.
Notice of Allowance received for U.S. Appl. No. 16/825,998, dated Jul. 27, 2021, 10 pages.
Final Office Action received for U.S. Appl. No. 15/826,289, dated Oct. 5, 2021, 10 pages.
Non-Final Office Action received for U.S. Appl. No. 15/826,370, dated Nov. 23, 2021, 35 pages.
Notice of Allowance received for U.S. Appl. No. 16/825,998, dated Oct. 22, 2021, 2 pages.

\* cited by examiner

|  | Pressure Increase | Operational Pressure | Pressure Ratio | Air Volume |
|---|---|---|---|---|
| Fan | Low Increase | Atm - 1.5psig | below 1.1 | High |
| Blower | Moderate Increase | 1.5psig - 2.72 psig | 1.11-1.20 | Very High |
| Compressor | High Increase | >2.72psig | >2.0 | Low |

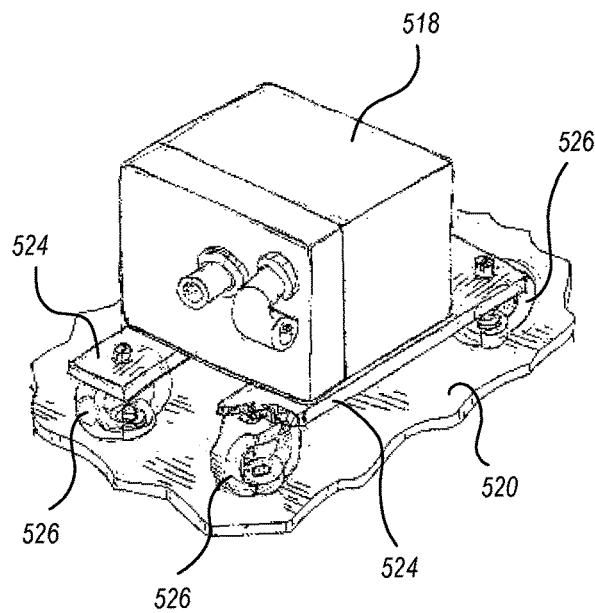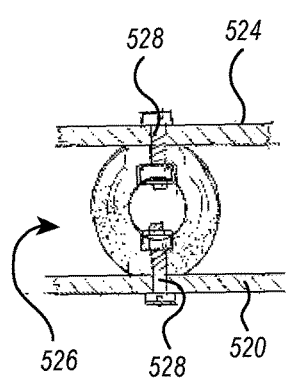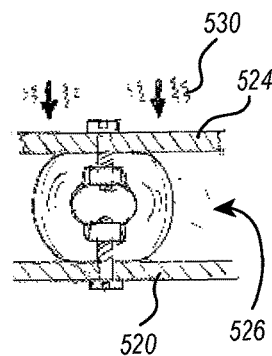
FIG. 24A     FIG. 24B     FIG. 24C
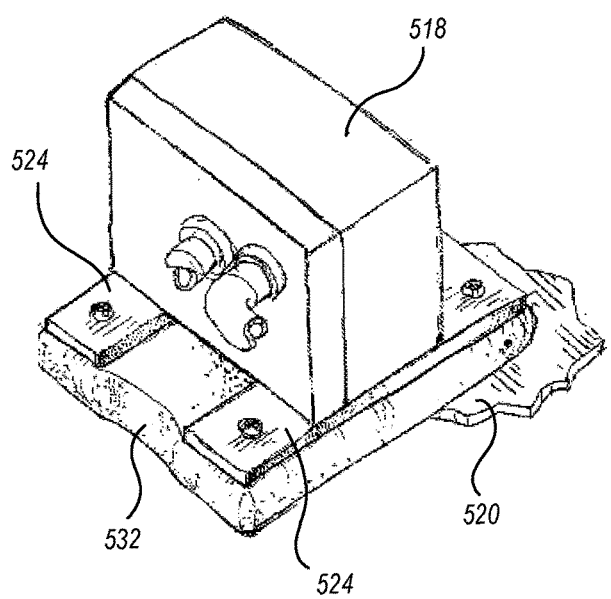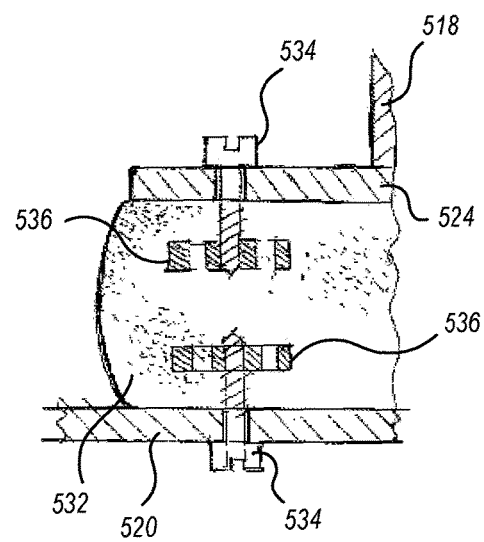
FIG. 25A     FIG. 25B

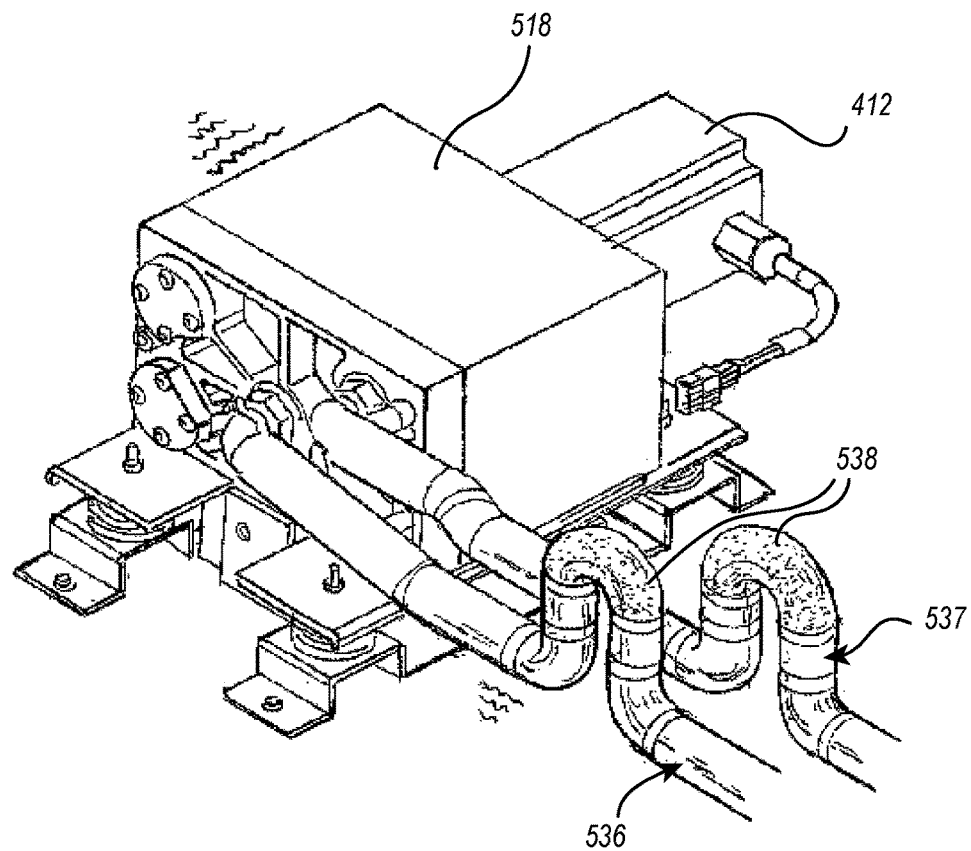
FIG. 26
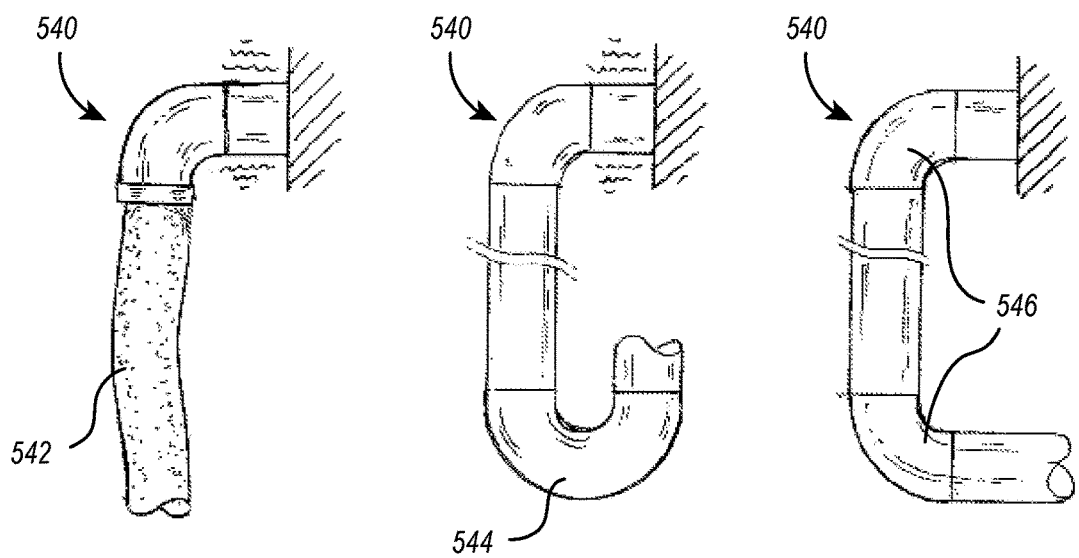
FIG. 27A  FIG. 27B  FIG. 27C

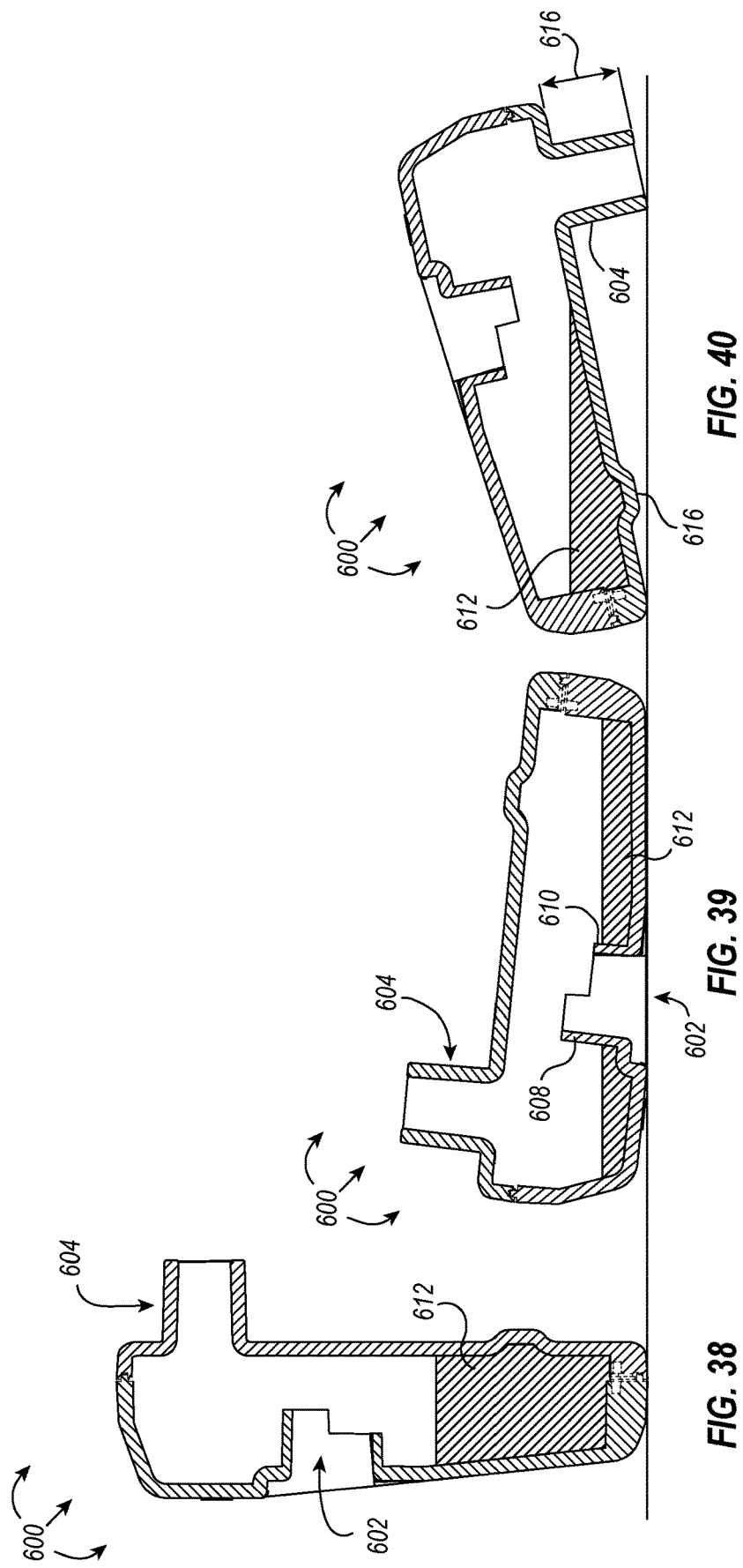

SMOKE EVACUATION DEVICE

BACKGROUND

1. Technical Field

The present disclosure relates to smoke evacuation systems.

2. The Relevant Technology

As is known to those skilled in the art, modern surgical techniques typically employ radio frequency (RF) power to cut tissue and coagulate bleeding encountered in performing surgical procedures. Such electrosurgery is widely used and offers many advantages including the use of a single surgical instrument for both cutting and coagulation. A monopolar electrosurgical generator system has an active electrode, such as in the form of an electrosurgical instrument having a hand piece and a conductive electrode or tip, which is applied by the surgeon to the patient at the surgical site to perform surgery and a return electrode to connect the patient back to the generator.

The electrode or tip of the electrosurgical instrument is small at the point of contact with the patient to produce an RF current with a high current density in order to produce a surgical effect of cutting or coagulating tissue through cauterization. The return electrode carries the same RF signal provided to the electrode or tip of the electrosurgical instrument, after it passes through the patient, thus providing a path back to the electrosurgical generator.

Electrosurgical instruments communicate electrical energy to a target tissue of a patient to cut the tissue and/or cauterize blood vessels within and/or near the target tissue. This cutting and cauterization results in smoke released into the air that can be distracting or otherwise unpleasant. Many electrosurgical systems may therefore employ an evacuation system that captures the resulting smoke and directs it through a filter and exhaust port, away from practitioners and/or patients. A smoke evacuation system typically creates suction directed at the smoke using fans to draw the smoke through a tube connecting the surgical instrument to an exhaust port.

Smoke evacuation systems typically comprise a pump and a filter. The pump creates suction that draws smoke through a vacuum tube into the filter. A vacuum tube may terminate at the hand piece that includes the electrode tip so that the smoke is sucked in at the hand piece. Other electrosurgical systems may include separate hand pieces that are used to suck the smoke into the system. The smoke travels to the filter via a vacuum tube and offensive smells and particulate are filtered out as the smoke moves through the filter. Filtered air may then exit the smoke evacuation system as exhaust. Periodically replacing the filters is necessary for the smoke evacuation system to remain effective.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

The present disclosure relates to smoke evacuation systems used in electrosurgical systems.

In one embodiment, a smoke evacuation system includes a housing surrounding an enclosure and an airflow path extending inside the enclosure from an inlet port to an outlet port of the smoke evacuation system. The system also includes a motor and pump disposed within the enclosure. A cooling mechanism is configured to induce airflow through the enclosure to cool the enclosure. The induce airflow is proportionate to the work output of the motor.

In one embodiment, a smoke evacuation system includes an inlet port, outlet port, an airflow path extending between the inlet port and the outlet port, and one or more cooling vents. The smoke evacuation system also includes an exhaust mechanism near the outlet port. The exhaust mechanism is configured to diffuse air exiting at the outlet port.

In one embodiment, a smoke evacuation system includes an airflow control mechanism, an exhaust diffuser, and a rotary mechanism. The airflow control mechanism reduces a pressure within the smoke evacuation system when abnormal flow or high pressures are detected. The exhaust diffuser reduces the exit noise of the filtered air without baffling or redirecting flow causing an exit head pressure. The rotary mechanism induces an airflow through the smoke evacuation system at a flow rate that is proportional to the rate at which a pump is pumping filtered air through the smoke evacuation system.

In one embodiment, a filter connection for a smoke evacuation system includes a filter canister and a socket. The filter canister comprises first and second ends, a body extending between the first and second ends, a connection nipple, a seal disposed around the connection nipple, and a first electronic connector. The socket comprises a first recess configured to receive the canister body, a second recess configured to receive the connection nipple, and a second electronic connector. The longitudinal distance between the seal and the first electronic connector is greater than the longitudinal distance between the second recess of the socket and the second electronic connector.

In one embodiment, a filter canister for a smoke evacuation system includes a first end having an inlet port, a second end, an electronic connector, and a connection nipple disposed at the second end. The cross-sectional shape of the second end of the filter canister has only one line of symmetry. The electronic connector is disposed at the second end of the filter canister.

In one embodiment, a method for connecting a filter in a smoke evacuation system includes the following steps: providing a filter canister; providing a socket in the smoke evacuation system; inserting the filter canister a first distance into the socket so that the filter canister creates an airtight boundary between the filter canister and the socket; and inserting the filter canister a second distance into the socket so that an a electronic connection is made between the filter canister and the socket. The second distance is greater than the first distance.

In one embodiment, a smoke evacuation system includes a filter, a pump that has a sealed positive displacement airflow path, and a motor that drives the pump. The sealed positive displacement airflow path of the pump may comprise one or more circulation paths of a gas within the pump. In one embodiment, the pump has a first operating pressure and a second operating pressure. The flow rate of a gas being pumped may be the same regardless of the operating pressure. The pump may compress incoming gas to create a pressure difference between various zones of airflow within the smoke evacuation system.

In one embodiment, a smoke evacuation system may include various vibration absorption mechanisms. The system may have a first housing enclosing the motor and the pump and a second housing enclosing the entire system. Vibration mechanisms may be disposed between the two housings and outside the second housing. Flexible tubing may also be incorporated to absorb vibrations.

A method of reducing the vibrations and noise of a smoke evacuation system may include regulating the motor engaged with the pump. The regulation of the motor may include varying a supply of current to the motor in order to operate the motor in at least two distinct operating levels. Regulation of the motor may depend on sensory inputs, such as temperature or pressure. Orifices may also be provided within the airflow path that allow communication with ambient surroundings of the system in order to relieve excessive resistance pressures in the system caused by blockages or clogging of the airflow path.

In an embodiment, a fluid trap for minimizing the escape of contaminated fluids from the fluid trap when an orientation of the fluid trap changes during removal or transport includes (i) a front cover defining an inlet port that extends a first distance into an interior chamber of the fluid trap, (ii) a rear cover coupled to the front cover and which defines an exhaust port extending a second distance away from the rear cover of the fluid trap and positioned above the inlet port when the fluid trap is in an upright position, and (iii) an interior chamber defined by the front and rear covers. The interior chamber includes a maximum fluid volume at least partially defined by the lesser of a fluid reservoir volume, a front cover volume, and a rear cover volume.

In one or more embodiments, the fluid reservoir volume is the volume defined by the interior sidewalls of the fluid trap below the inlet port, the front cover volume is equivalent to a product of the surface area of the front cover and an average depth of the front cover with respect to the first distance of the inlet port, and the rear cover volume is the volume of the interior chamber defined by interior sidewalls of the fluid trap and bounded by a line tangent to a lowest interior-facing sidewall of the exhaust port that is parallel with a surface upon which the exhaust port lies.

In an embodiment, a fluid trap for minimizing the escape of contaminated fluids includes an interior chamber defined by sidewalls of the fluid trap, an inlet port extending into the interior chamber that is or includes a notched cylindrical body that directs smoke in a defined direction, and an exhaust port positioned opposite and above the inlet port. The exhaust port defines an open channel between the interior chamber of the fluid trap and an area outside the fluid trap. Additionally, the fluid trap can include a splash canopy positioned between the inlet port and the exhaust and extending laterally across a width of the inlet port, and in an embodiment, the fluid trap additionally includes a splash wall spanning opposing sidewalls of the interior chamber and extending vertically from a first point coplanar with at least a portion of the splash canopy to a second point coplanar with at least a portion of the exhaust port. The splash canopy and/or the splash wall can, in some embodiments, include a fibrous fluid wicking material that enables removal of aerosols and/or small droplet fluids and additionally, or alternatively, act as condensation promoting surfaces.

In an embodiment, a smoke evacuation system includes a suction pump, a filter connected to the suction pump, and a fluid trap connected to the filter. The fluid trap includes an interior chamber, a sensor disposed within the interior chamber for monitoring a fluid level within the fluid trap, and a visual indicator in electrical communication with the sensor that represents the fluid level within the fluid trap.

Additionally, in an embodiment, the sensor is an optical emitter and detector pair, an ultrasonic detector, a resistive strip, or a combination thereof that senses the amount of fluid in the fluid trap and activates a corresponding visual indicator to communicate the fill status of the fluid trap, such as the fluid trap reaching a maximum fill state.

In an embodiment, a filter includes (i) a filter body, (ii) a front cap associated with a first end of the filter body and coupled to and receiving smoke from a vacuum hose, (iii) a back cap associated with a second end of the filter body and having a filter exhaust sized and shaped to associate with and communicate suction from a smoke evacuation system, (iv) a compressed carbon reservoir disposed within the filter body between the front cap and the back cap, and (v) a flexible porous barrier disposed on at least a first side of the compressed carbon reservoir.

In an embodiment, a replaceable filter for processing smoke derived from electrosurgery includes (i) a filter body, (ii) a front cap associated with a first end of the filter body, (iii) a back cap associated with a second end of the filter body and configured to receive suction, (iv) one or more particulate filters disposed within the filter body between the front cap and the back cap, (v) a compressed carbon reservoir disposed within the filter body between the one or more particulate filters and the back cap, and (vi) a flexible porous barrier disposed on at least a first side of the compressed carbon reservoir.

In an embodiment, a three-stage filter for processing smoke derived from electrosurgery includes a first stage for removing one or more fluids from the smoke, a second stage for removing particulates, and a third stage having a compressed carbon reservoir. The first stage can include a fluid trap having a fluid trap inlet port and a fluid trap exhaust port. The fluid trap inlet port extends into an interior chamber of the fluid trap and couples to and receives smoke from a vacuum hose. The fluid trap exhaust port is positioned opposite and above the fluid trap inlet port and defines an open channel between an interior chamber of the fluid trap, where one or more fluids extracted from the smoke are retained, and the second stage of the three-stage filter. In some embodiments, the second-stage removes particulates using one or more particulate filters, such as a coarse media filter and an ultra-low penetration air (ULPA) filter in series. In some embodiments, the third stage can be under a compressive bias by a flexible porous barrier. The flexible porous barrier can transition from a flexed state to a partially relaxed state in response to the compressed carbon reservoir reducing in volume, which in some embodiments is caused by settling of the compressed carbon reservoir or pressure from suction applied to the compressed carbon reservoir.

In an embodiment, an RF current sensor is configured to operate in at least two modes—a first mode and a second mode—and includes (i) a sensor body having at least a cable interfacing sidewall and a retaining member, the cable interfacing sidewall and the retaining member defining a retention pocket configured to receive a cable communicating RF current, (ii) a sensor element for detecting RF current in the cable, and (iii) a sensor cable in electrical communication with the sensor element, the sensor cable communicating one or more of an activation signal or a current signal derived from the detected RF current to the smoke evacuation device.

The RF sensor can operate in the first mode when the sensor element identifies a single RF current in the cable. The single RF current in the cable can be communicated between a signal generator and an active electrode of a monopolar electrosurgical instrument or between a return electrode and the signal generator, and the activation signal and/or the current signal are derived from the single RF current when the RF current sensor operates in the first mode. The RF sensor can operate in the second mode when the sensor element identifies two RF currents—a first RF current flowing in an opposite direction as a second RF current—in the cable. Operating in the second mode causes the RF current sensor to detect the first RF current with respect to the second RF current and to derive the activation signal and/or the current signal from the first RF current.

In an embodiment, a method for remote activation of a smoke evacuation device includes (i) generating an RF current at a signal generator, (ii) communicating the RF current through a source cable to an electrosurgical instrument, (iii) detecting an activation of RF current with an RF current sensor communicatively coupled to a smoke evacuation device, (iv) communicating an activation signal from the RF current sensor to the smoke evacuation device in response to detecting the activation of RF current, (v) receiving the activation signal at the smoke evacuation device, and (vi) activating a vacuum source for one or more of a defined period of time or to generate a defined smoke evacuation flow rate in response to receiving the activation signal.

In some embodiments, the method for remote activation of a smoke evacuation device can additionally include (i) detecting the RF current with the RF current sensor subsequent to detecting the activation of RF current, (ii) periodically or continuously communicating a current signal from the RF current sensor to the smoke evacuation device in response to detecting the RF current, the signal current including data associated with the RF current, (iii) receiving the current signal at the smoke evacuation device, and (iv) in response to receiving the current signal, adjusting the defined period of time and/or the defined smoke evacuation flow rate of the vacuum source.

In some embodiments, the method for remote activation of a smoke evacuation device can additionally include deriving a treatment power based on the activation signal and/or the current signal and calculating an estimated smoke production based on the treatment power, and the defined period of time and/or the defined smoke evacuation flow rate can be based on the estimated smoke production.

In an embodiment, an electrosurgical system includes (i) a signal generator producing an RF current, (ii) a source cable electrically coupled to the signal generator and to an electrosurgical instrument, the source cable communicating the RF current from the signal generator to the electrosurgical instrument, (iii) a smoke evacuation device that includes a vacuum hose positioned proximate the electrosurgical instrument and configured to evacuate smoke generated by the electrosurgical instrument, and (iv) an RF current sensor communicatively coupled to the smoke evacuation device, the RF current sensor activating the smoke evacuation device in response to identifying the RF current.

In some embodiments, the RF current sensor is removably coupled to the source cable or the return cable and detects RF current flowing therethrough. In some embodiments, the RF current sensor is integrally formed within the return electrode or within the smoke evacuation device.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages of the disclosed embodiments will be set forth in the description which follows, and in part will be obvious from the description, or may be learned by the practice of the disclosure. These and other features will become more fully apparent from the following description and appended claims, or may be learned by the practice of the present disclosure.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIG. 24A illustrates one embodiment of vibration absorption mechanisms disposed between inner and outer housings;

FIGS. 24B and 24C illustrate various cross-sectional views of the vibration absorption mechanisms illustrated in FIG. 24A;

FIG. 25A illustrates one embodiment of a vibration absorption mechanism;

FIG. 25B illustrates a cross-sectional view of the vibration absorption mechanism illustrated in FIG. 25A;

FIG. 26 illustrates one embodiment of a vibration absorption mechanism;

FIGS. 27A through 27C illustrate various embodiments of vibration absorption mechanisms;

FIG. 38 illustrates a simplified vertical cross-section of the exemplary fluid trap depicted in FIG. 35 having fluid collected therein and in an upright position;

FIG. 39 illustrates a simplified vertical cross-section of the exemplary fluid trap depicted in FIG. 35 having fluid collected therein and positioned on a surface inlet-side down;

FIG. 40 illustrates a simplified vertical cross-section of the exemplary fluid trap depicted in FIG. 35 having fluid collected therein and positioned on a surface inlet side up;

DETAILED DESCRIPTION

The present disclosure relates to smoke evacuation systems used in electrosurgical systems. Some embodiments of the present disclosure relate to methods and apparatuses for managing noise and vibrations of smoke evacuation systems. Noise and vibrations produced by smoke evacuation systems can be distracting and irritating to practitioners performing surgery. Some embodiments relate to apparatuses and methods for controlling air flow parameters to cool the smoke evacuation system in order to avoid overheating. Still other embodiments relate to a filter connection for a smoke evacuation device. It may be difficult to determine when filters need to be replaced in smoke evacuation systems, and current filter connections can lead to faulty installations. The filter connection of the present disclosure may enable easy installation of filters, as well as other features to electronically detect and communicate when filters need to be replaced or when an incorrect filter has been installed. Further embodiments relate to fluid traps used to remove fluids and other materials evacuated from a surgical site. Embodiments disclosed herein also relate to remote activation devices that activate a smoke evacuation system upon detection of certain system parameters.

Reference is made herein to the evacuation of smoke and components that facilitate such function. It will be appreciated that references to "smoke" is merely for simplicity and convenience, and is not intended to limit the disclosed and claimed embodiments to evacuation of only smoke. Rather, the disclosed and claimed embodiments may be used to evacuate substantially any type of fluid, including liquids, gases, vapors, smoke, or combinations thereof. Additionally, rather than simply evacuating fluid, it is contemplated that at least some of the embodiments may be used to deliver fluids to a desired location, such as a surgical site. As used herein, the term "fluid" includes bulk liquids and/or liquid vapor, which can include liquids—biologic in origin or otherwise—obtained from or introduced into a surgical site (e.g., water, saline, lymph, blood, exudate, pyogenic discharge, and/or other fluid). A "fluid" is additionally intended to include cellular matter or debris that is transported through a vacuum hose and into the fluid reservoir of a mechanically coupled fluid trap.

General

Figure 1:
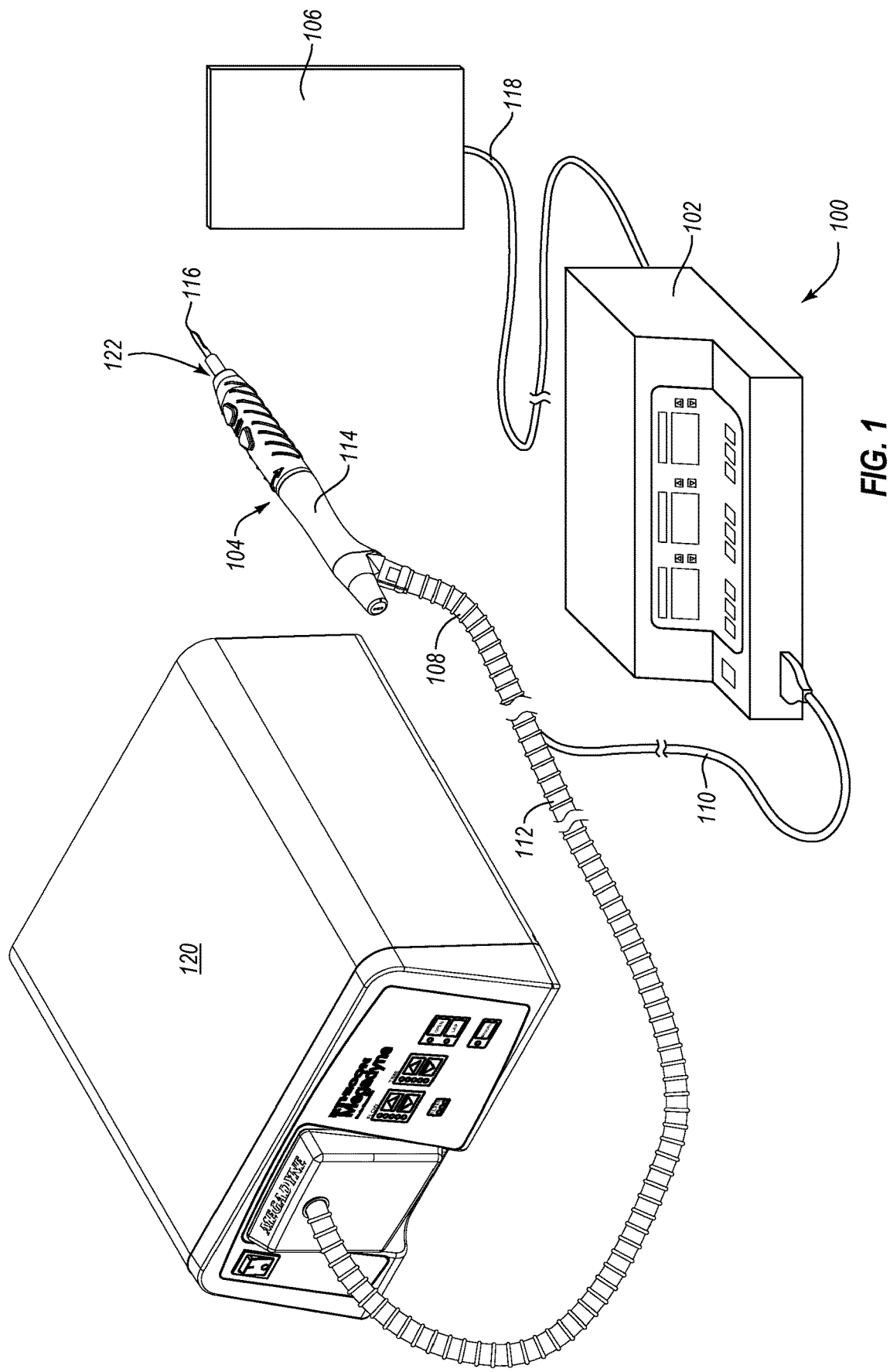
FIG. 1 illustrates an embodiment of an electrosurgical system.

FIG. 1 illustrates an exemplary electrosurgical system 100. The illustrated embodiment includes a signal generator 102, an electrosurgical instrument 104, a return electrode 106, and a smoke evacuation system 120. Generator 102, in one embodiment, is an RF wave generator that produces RF electrical energy. Connected to electrosurgical instrument 104 is a utility conduit 108. In the illustrated embodiment, utility conduit 108 includes a cable 110 that communicates electrical energy from generator 102 to electrosurgical instrument 104. The illustrated utility conduit 108 also includes a vacuum hose 112 that conveys captured/collected smoke and/or fluid away from a surgical site.

Generally, electrosurgical instrument 104 includes a hand piece or pencil 114 and an electrode tip 116. Electrosurgical instrument 104 communicates electrical energy to a target tissue of a patient to cut the tissue and/or cauterize blood vessels within and/or near the target tissue. Specifically, an electrical discharge is delivered from electrode tip 116 to the patient in order to cause heating of cellular matter of the patient that is in close contact with or adjacent to electrode tip 116. The tissue heating takes place at an appropriately high temperature to allow electrosurgical instrument 104 to be used to perform electrosurgery. Return electrode 106 is connected to generator 102 by a cable 118, and is either applied to or placed in close proximity to the patient (depending on the type of return electrode), in order to complete the circuit and provide a return electrical path to wave generator 102 for energy that passes into the patient's body.

The heating of cellular matter of the patient by the electrode tip 116, or cauterization of blood vessels to prevent bleeding, results in smoke being released where the cauterization takes place. The electrosurgical instrument 104 may comprise a smoke evacuation conduit opening 122 near the electrode tip 116 so as to be able to capture the smoke that is released during a procedure. Vacuum suction may draw the smoke into the conduit opening 122, through the electrosurgical instrument 104, and into the vacuum hose 112 toward the smoke evacuation system 120.

Figure 2:
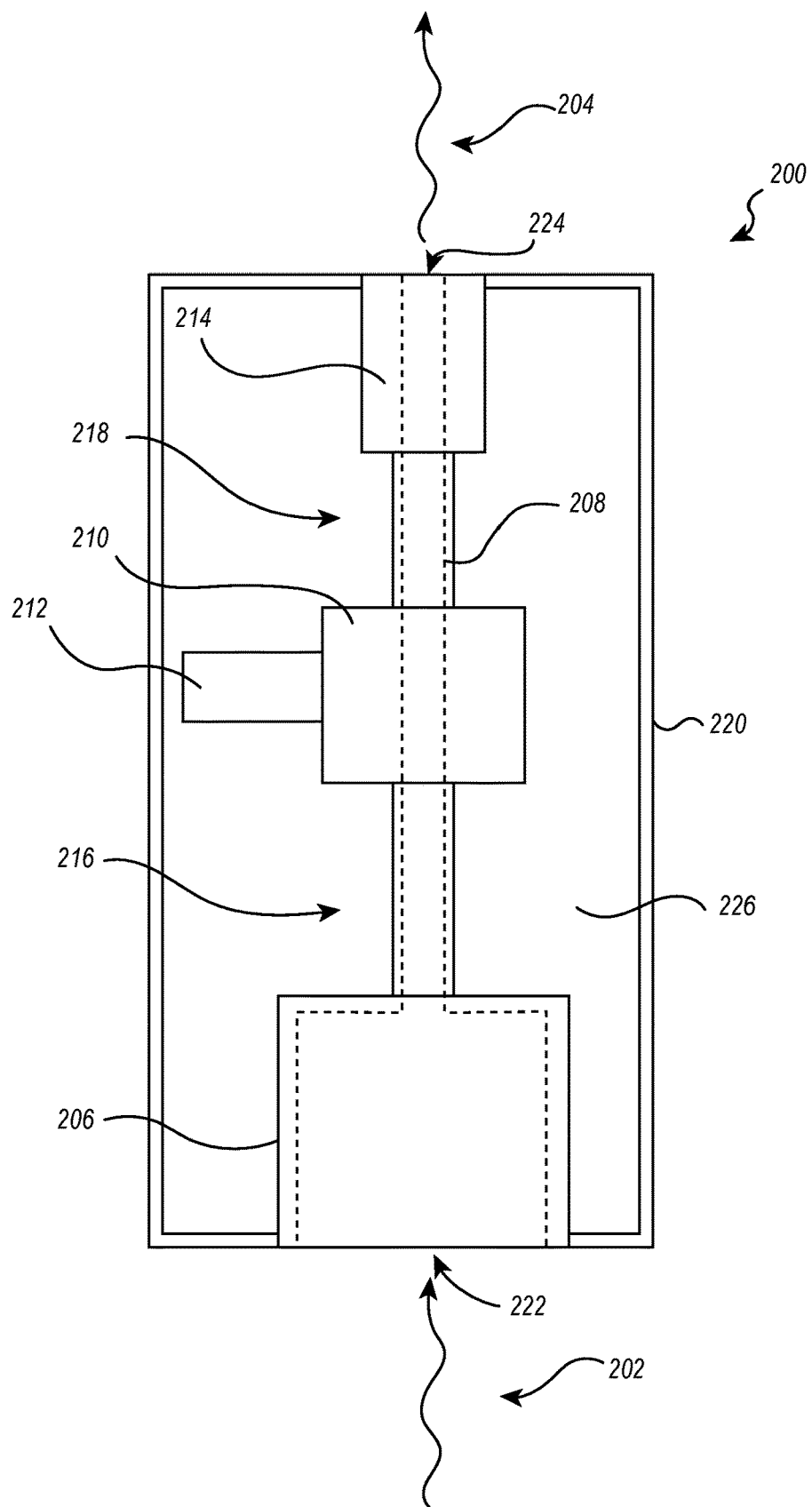
FIG. 2 illustrates a schematic of a smoke evacuation system.

FIG. 2 illustrates an embodiment of a smoke evacuation system 200. The smoke evacuation system 200 may include a filter 206 and an airflow path 208. The airflow path 208 may comprise a pump 210 disposed in-line with the airflow path 208 producing a pressure difference within the airflow path 208 by mechanical action. The term "pump" as used herein refers to blowers, compressors, and other mechanical means of moving a fluid/gas while increasing the pressure of the fluid/gas. This pressure difference may cause movement of a gas through the airflow path 208. The gas drawn through the airflow path 208 may be smoke 202, or the filtered air remaining after the smoke 202 has passed through the filter 206. A motor 212 drives the pump 210. The smoke evacuation system 200 may also include an exhaust mechanism 214 that may also be disposed in-line with the airflow path 208.

The airflow path 208 may be disposed between an inlet port 222 and an outlet port 224. The smoke 202 may flow into the filter 206 at the inlet port 222, be pumped through the airflow path 208 by the pump 210 so that the smoke 202 is drawn through the filter 206, through the exhaust mechanism 214, and out the outlet port 224 of the smoke evacuation system 200. The air exiting the smoke evacuation system 200 at the outlet port 224 may be the exhaust 204. The exhaust 204 may consist of filtered air/gas that has passed through the smoke evacuation system 200 and exits through the outlet port 224.

The airflow path 208 may comprise a first zone 216 and a second zone 218. The first zone 216 may be upstream from the pump 205 and the second zone 218 may be downstream from the pump 205. The pump 205 may pressurize the air in the airflow path 208 so that the air in the second zone 218 has a higher pressure than the air in the first zone 216. This pressure difference causes air to flow through the airflow path 208 from the inlet port 222 to the outlet port 224.

The smoke evacuation system 200 may also include a housing 220. FIG. 2 illustrates a schematic view of a smoke evacuation system 200 to show the various components within the housing 220. An enclosure 226 may be defined by the space inside the housing 220 but outside the airflow path 208. The housing 220 may completely or partially encompass or enclose the smoke evacuation system 200. The airflow path 208 may be at least partially comprised of a tube or other conduit that substantially contains and/or isolates the air moving through the airflow path 208 air outside the airflow path 208.

For example, the first zone 216 of the airflow path 208 may comprise a tube through which the airflow path 208 extends between the filter 206 and the pump 210. The second zone 218 of the airflow path 208 may also comprise a tube through which the airflow path 208 extends between the pump 210 and the exhaust mechanism 214. The airflow path 208 also extends through the filter 206, pump 210, and exhaust mechanism 214 so that a continuous airflow path 208 extends from the inlet port 222 to the outlet port 224.

Controlling Flow Parameters

Figure 3A:
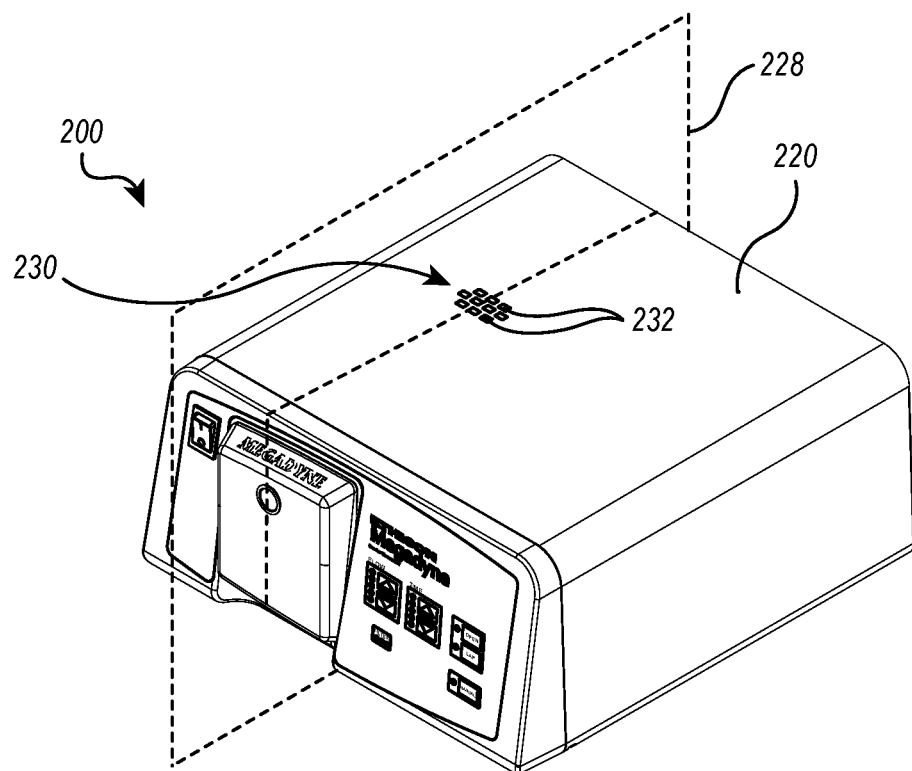
FIG. 3A illustrates a perspective view of an embodiment of a smoke evacuation system.

FIG. 3A illustrates a smoke evacuation system 200 that includes a cooling mechanism 230. The cooling mechanism 230 may include a plurality of openings 232 in the outer housing 220 of the smoke evacuation system 200. The embodiment illustrated in FIG. 3A includes ten square-shaped openings 232 disposed together in a group. Air may flow into the smoke evacuation system 200 through the openings 232 in the outer housing 220. Air that enters through the openings 232 may cool internal components of the smoke evacuation system 200, such as the motor and/or pump, by convective heat transfer.

Other embodiments of a smoke evacuation system 200 may include cooling mechanisms 230 that have more or less than ten openings 232. For example, one embodiment may include only one opening 232. Other embodiments may include more than ten openings 232. It will be appreciated that a large number of variations in the openings 232 in the outer housing 220, including the size, shape, and number of openings 232, may be employed in other embodiments to achieve the same or similar cooling effects of the openings 232.

The openings 232 may be positioned in the outer housing 220 to facilitate cooling of certain components within the outer housing 220. For example, in the embodiment illustrated in FIG. 3A, the openings 232 are positioned such that they may be directly over a motor (e.g., motor 212 in FIG. 2) inside the outer housing 220. In other embodiments, the openings 232 may be positioned elsewhere to correspond with a motor that may be at a different location inside the outer housing 220. The openings may be place on the top, bottom and/or side surfaces of the outer housing 220. One will appreciate that the openings 232 may be strategically place anywhere in the outer housing 220 to facilitate convective cooling of the various components inside the outer housing 220.

Figure 3B:
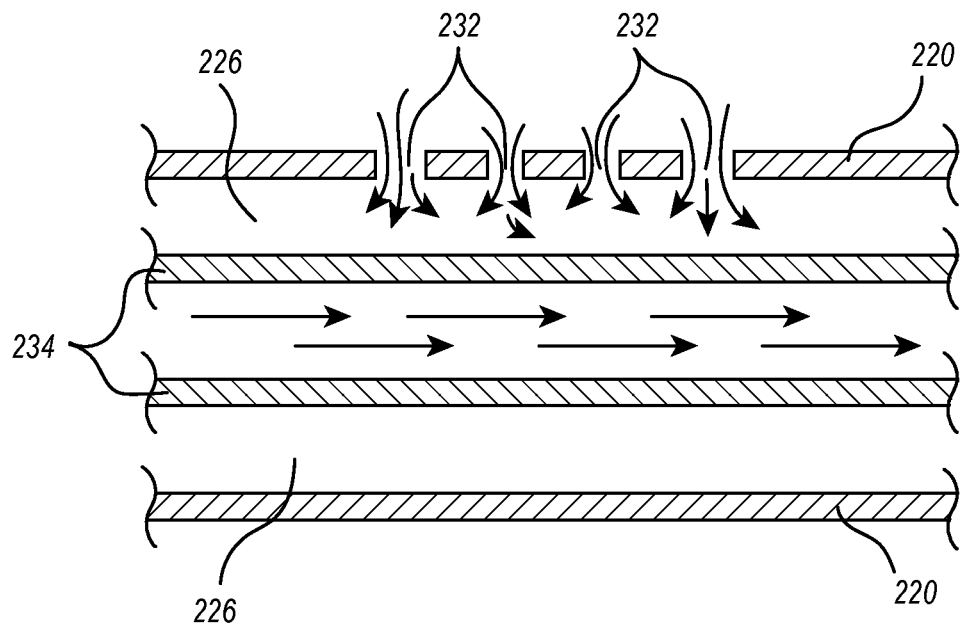
FIG. 3B illustrates a partial cross-sectional view of the smoke evacuation system illustrated in FIG. 3A.

FIG. 3B illustrates a partial cross-sectional view of the smoke evacuation system 200 of FIG. 3A on plane 228. The arrows in FIG. 3B indicate airflow. Air may flow inside the airflow path 208 of the smoke evacuation system 200 through a tube 234 and the various components that form or define the airflow path 208, such as the filter 206, pump 210, and exhaust mechanism 214. Air from outside the outer housing 220 may flow into the enclosure 226 of the smoke evacuation system 200 through the openings 232, as indicated by the arrows through the openings 232. In the illustrated embodiment, the air flowing through airflow path 208 may be sealed off from the air entering through the openings 232 so that no mixing occurs. The air entering through the openings 232 may cool the motor 215, pump 210, exhaust mechanism 214, tube 234 or other components the air comes into contact with by convective heat transfer. These components may also be cooled when hot air within the enclosure escapes out of the openings 232.

Figure 4:
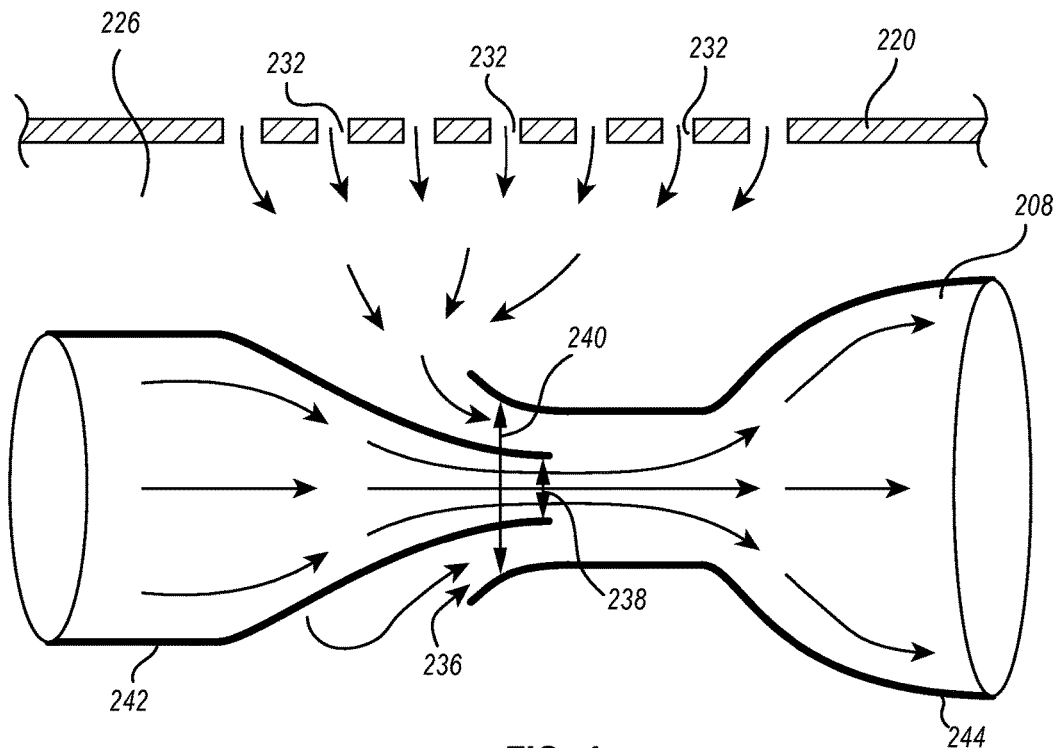
FIG. 4 illustrates a partial cross-sectional view of an embodiment of a cooling mechanism.

Alternatively, in another embodiment illustrated in FIG. 4, the air flowing through the airflow path 208 may not be sealed off from air entering the smoke evacuation system 200 through the openings 232 in the outer housing 220. In this embodiment, the air entering through the openings 232 may enter into the airflow path 208 to mix with the air flowing through the airflow path 208. This mixing may cause the air flowing inside the airflow path 208 to be cooled by the air flowing into the airflow path 208 through the openings 232 in the outer housing 220.

One or more airflow path openings 236 may be provided in the airflow path 208 so that air from outside the airflow path 208 may enter into the airflow path 208. In one embodiment, the opening may be an open juncture 236 between a first portion of the airflow path 242 and a second portion of the airflow path 430. The first portion 242 may extend into a second portion 244. The first portion 242 may have a first diameter 238 and the second portion 244 may have a second diameter 240. The first diameter 236 may be smaller than the second diameter 240. The first portion 242 may extend at least partially into the second portion 244 so that the second portion 244 at least partially receives the first portion 242. In this configuration, substantially all of the air flowing through the airflow path 208 may remain inside the airflow path 208 as it flows from the first portion 242 to the second portion 244.

As the air within the airflow path 208 flows from the first portion 242 to the second portion 244, a suction may be created that draws air from outside the airflow path 208 into the airflow path 208. In this way, air from outside the outer housing 220 may enter into the outer housing 220 through the openings 232 in the outer housing 220 and enter the airflow path 208 through the one or more open junctures 236 to mix with air flowing inside the airflow path 208. This mixing may cause the airflow path 208 or other components, such as the pump 210 and/or motor 212, to be cooled.

For example, after the air is mixed and cooled within the airflow path 208 according to the embodiment illustrated in FIG. 4, the cooled air may then pass through the pump 210. Also for example, air that enters the smoke evacuation system 200, but does not mix with the air inside the airflow path 208, may freely flow within the outer housing 220 so that it flows over/around the motor 212, causing the motor 212 to be cooled.

The embodiment illustrated in FIG. 4 illustrates an airflow path 208 that includes one open juncture 236 in the airflow path 208 through which air may enter. Other embodiments may include more than one airflow path openings 210. For example, one embodiment may include two or more open junctures 236 disposed in series along the airflow path 208. Increasing the number of open junctures 236 may increase the mixing of air from outside the airflow path 208 with air inside the airflow path 208 to increase cooling capacity.

Figure 5A:
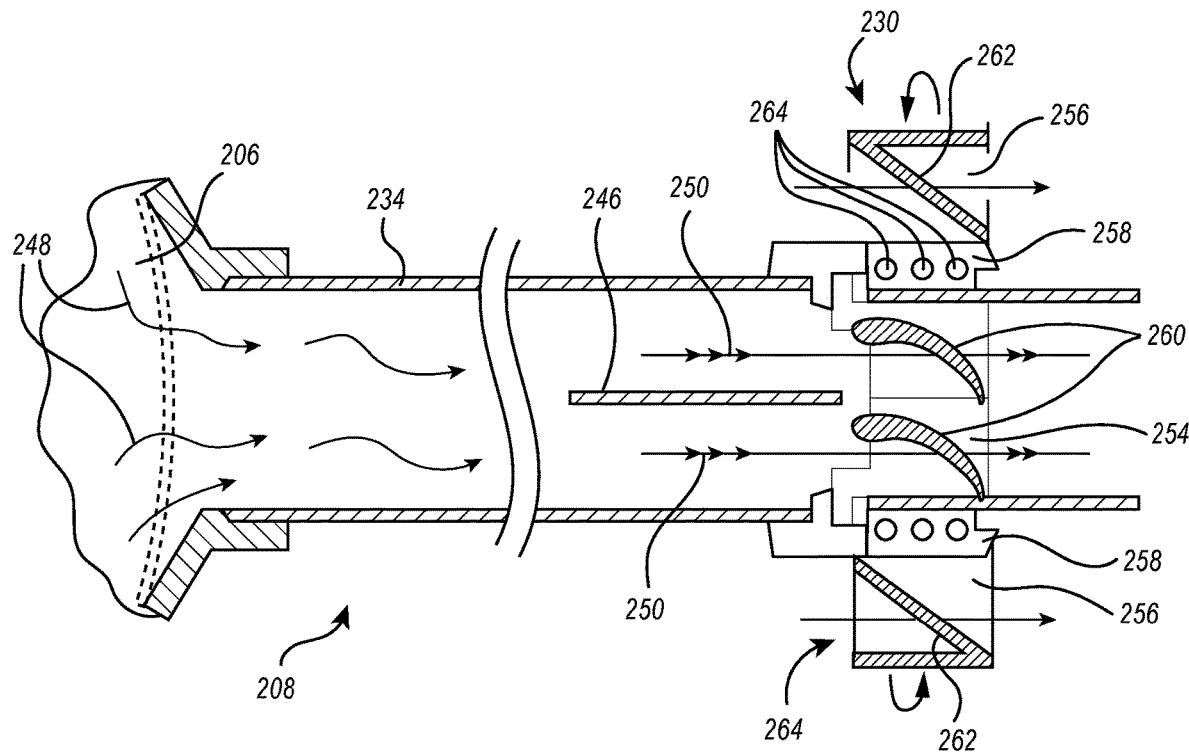
FIG. 5A illustrates a cross-sectional view of an embodiment of a cooling mechanism.

FIG. 5A illustrates an embodiment of an airflow path 208 that has a cooling mechanism 230. The airflow path 208 may be comprised of a tube 234 or other conduit through which air may flow. The air is indicated by the arrows in the airflow path 208. The airflow path may also include one or more interior walls 246 configured to straighten or direct the airflow. Air exiting the filter 206, indicated by arrows 248, may be flowing turbulently. The one or more walls 246 may create channels that direct air 250 in the downstream direction, as indicated by arrows 250, resulting in more laminar flow.

Figure 5B:
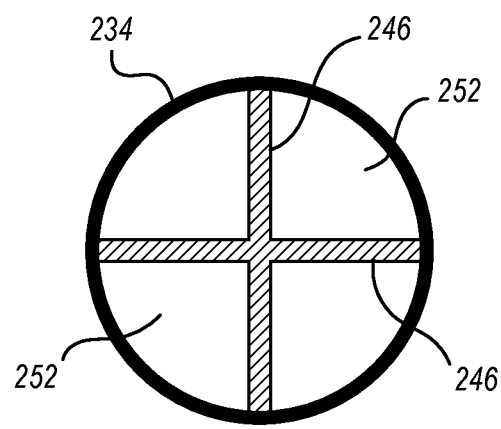
FIG. 5B illustrates a front view of an embodiment of an airflow path.

FIG. 5B illustrates a cross sectional view of the airflow path 208 where the one or more walls 246 are located in FIG. 5A. The one or more walls 246 may create one or more channels 252 through which the air 250 may flow. The channels may be bounded by the one or more walls 252 and the tube 234 or other conduit of the airflow path 208. Other embodiments may include one or more walls 246 that create more or less than the four channels 252 illustrated in FIG. 5B. Other embodiments may also include one or more walls 246 that create channels 252 having various shaped cross-sections, such as circular, square, or other shaped cross-sections.

Referring back to FIG. 5A, the cooling mechanism 230 may include a first rotary element 254 coupled to a second rotary element 256 via a rotary element coupler 258. The first rotary element 254 may comprise a plurality of first rotary element blades 260 and the second rotary element 256 may comprise a plurality of second rotary element blades 262. The second rotary element 256 may be disposed outside and surrounding the tube 234 of the airflow path 208 and inside the enclosure 226 of the smoke evacuation system 200. The first rotary element 254 may be disposed within the tube 234 of the airflow path 208.

As noted, the first and second rotary elements 254, 256 may be coupled by a rotary element coupler 258 so that rotation of the first rotary element 254 causes the rotation of the second rotary element 256. For example, air 250 flowing through the airflow path 208 may push against the first rotary element blades 260 causing the first rotary element 254 to rotate. The rotation of the first rotary element 254, which is coupled to the second rotary element 256, may cause the second rotary element 256 to rotate as well.

Figure 5C:
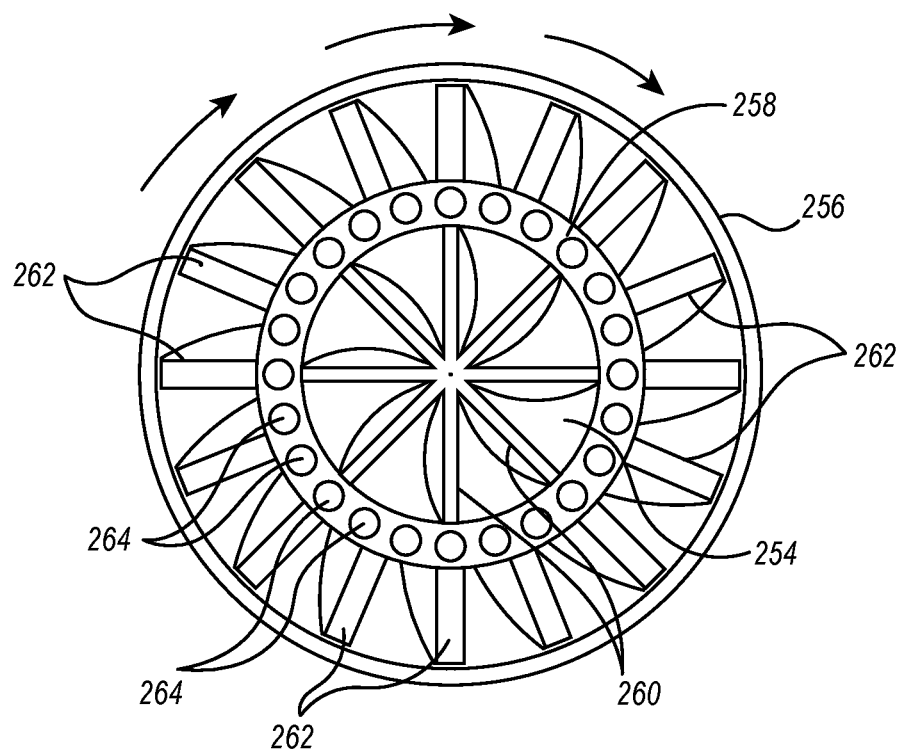
FIG. 5C illustrates a front view of the cooling mechanism illustrated in FIG. 5A.

The rotary element coupler 258 may be disposed in-line with the airflow path 208 so that air does not escape the airflow path 208 at the rotary element coupler 258. The rotary element coupler 258 may rotate with the first rotary element 254 and therefore may comprise a plurality of ball bearings 264 to reduce frictional resistance to rotation while maintaining a tight fit within the airflow path 208 to avoid leaking. In this way, the rotary element coupler 258 may also be integrated into the tube 234 of the airflow path 208 to maintain a sealed path for air to flow within the airflow path 208. FIG. 5C illustrates a front cross-sectional view of the first rotary element 254, second rotary element 256, and rotary element coupler 258 with ball bearings 264 for further reference.

The second rotary element blades 262 may move air in the enclosure 226 to flow to and/or around other components inside the enclosure 226. For example, a motor 212 may be disposed within the enclosure 226. The motor may drive the pump 210 to create a flow of air 248, 250 through the airflow path 208. The air 248 may flow through the first rotary element 254, causing the first and second rotary elements 254, 256 to rotate as discussed above. The second rotary element 256 may move air that has been drawn into the enclosure 226 from outside the enclosure 226, as described above, and circulate the air throughout the enclosure 226. The circulating air may cool the motor 212 by convective heat transfer.

Therefore, the cooling capacity of the circulated air pushed by the second rotary element 256 may be proportional to the work of the motor 212. For example, the more work output by the motor 212, the greater the rate of the airflow through the airflow path 208 may be. A greater rate of airflow may result in a greater velocity of circulated air pushed throughout the enclosure 226 by the second rotary element 256. Therefore, the more work produced by the motor 212, the greater the cooling capacity of the cooling mechanism 230 may be. The cooling mechanism 230 may also be configured to cool other components within the enclosure 226, such as the pump 210.

Figure 6:
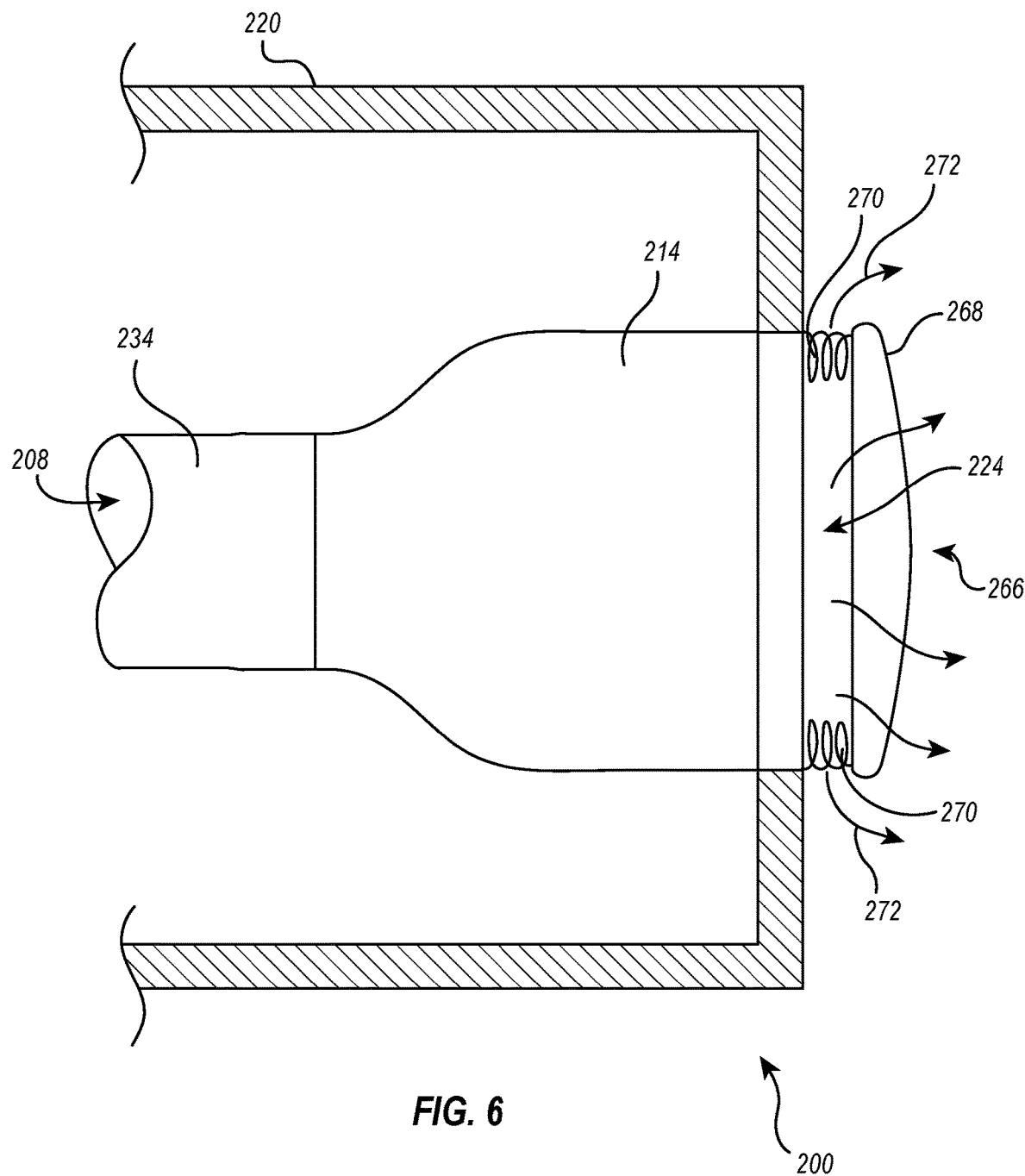
FIG. 6 illustrates an embodiment of an exhaust mechanism and a pressure relief mechanism disposed at an outlet port of a smoke evacuation system.

FIG. 6 illustrates an embodiment of an exhaust mechanism 214 disposed within the outer housing 220 near or at the outlet port 224. The exhaust mechanism 214 may include a pressure relief mechanism 266 disposed at the outlet port 224 of the smoke evacuation system 200. The exhaust port 266 may be connected with the tube 230 or other conduit through which air flows in the airflow path 208. The air flowing through the airflow path 208 may be pressurized by the pump 210 illustrated in FIG. 2. The pressure relief mechanism 266 may limit the suction of the smoke evacuation system 200 when abnormal flow or high pressure is detected within the airflow path 208.

The pressure release mechanism 266 may comprise an outlet port cover 268 disposed over the outlet port 224. The cover 268 may be secured over the outlet port 224 via one or more biasing members 270. In the illustrated embodiment, the one or more biasing members 272 are coil springs. Other types of biasing members 270 may be used in other embodiments or in combination with the springs illustrated in FIG. 6. The biasing springs 268 may hold the cover 268 away from the outlet port 224 so that filtered air 272 may exit out of the outlet port 224. As pressure within the airflow path 208 increases, the one or more biasing members 270 may extend so that the cover is further away from the outlet port 224 to increase airflow out of the outlet port 224. Increasing airflow out of the outlet port may decrease a pressure within the airflow path 208.

In this way, the pressure release mechanism 266 may limit the pressure within the airflow path 208 by increasing airflow out of the outlet port 224. A pressure limit, which depends on the biasing force of the biasing members 270, may therefore not be exceeded within the airflow path 208. A similar pressure release mechanism may also be disposed at the inlet port 222 of the smoke evacuation system 200 to regulate a pressure within the airflow path 208. It will also be appreciated that a similar pressure release mechanism may be disposed anywhere along the airflow path 208 to accomplish the same objective of relieving pressure in the system. For example, a pressure release mechanism may be disposed at an inlet or outlet of the pump 210.

It will be appreciated that other embodiments of a pressure relief mechanism may be employed to ensure that a pressure limit is not exceeded within the smoke evacuation system 200. For example, any mechanism that increases airflow out of the outlet port 224 or pump outlet, proportional to an increased pressure in the airflow path 208, may be suitable. Likewise, any mechanism that decreases airflow into the system at the inlet port 222 or pump inlet, proportional to an increase in pressure detected within the airflow path 208, may also be suitable.

For example, one embodiment of a pressure relief mechanism may include a controller and a pressure sensor. The pressure sensor may signal the controller to activate a mechanism that increases or decreases flow in or out of the smoke evacuation system similar to the pressure relief mechanisms described above. A pressure limit may be pre-determined and set so that when the sensor senses a pressure within the smoke evacuation system that is equal to or greater than the pressure limit, the pressure relief mechanism is activated by the controller.

Figure 7A:
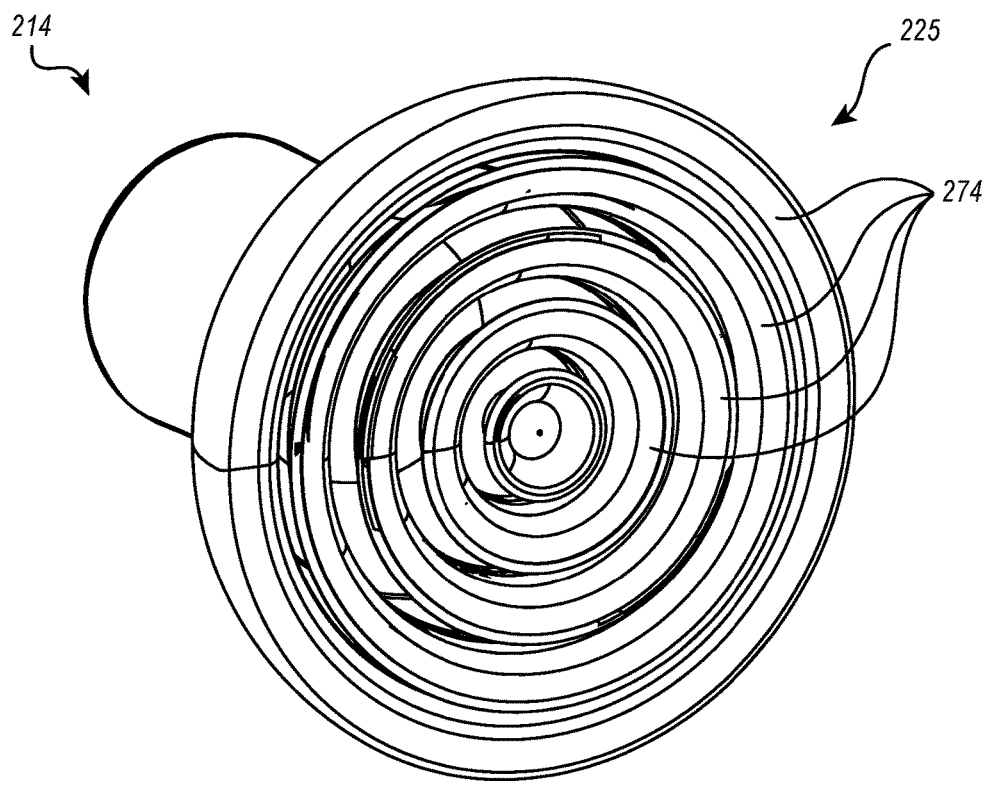
FIG. 7A illustrates a perspective view of a diffuser.
Figure 7B:
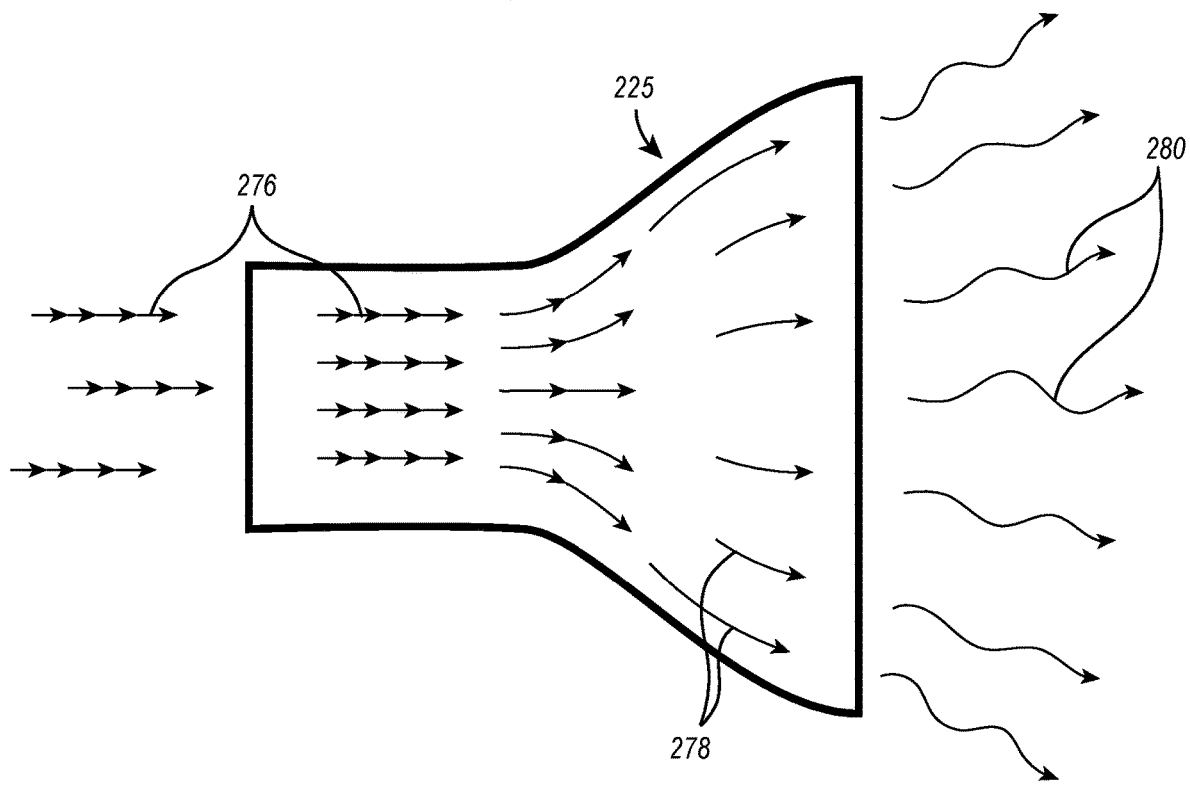
FIG. 7B illustrates a schematic of the diffuser illustrated in FIG. 7A.

FIGS. 7A and 7B illustrate an embodiment of an exhaust mechanism 214. The exhaust mechanism 214 may be configured to control or reduce the velocity of filtered air from the airflow path 208 exiting the smoke evacuation system 200 at the outlet port 224. The exhaust mechanism 214 may also be configured to decrease noise associated with high velocity filtered air exiting the outlet port 224. The exhaust mechanism 214 may help to reduce exit noise of the filtered air without baffling or redirecting flow causing an exit head pressure.

FIG. 7A illustrates a perspective view of an exhaust mechanism 214. The exhaust mechanism may be a diffuser 225. The diffuser 225 may include a plurality of vanes 274. The vanes 274 may be spaced apart and angled such that filtered air may flow out through the diffuser 225 between the vanes 274. The vanes 274 may be angled such that the vanes 274 force the air in a variety of directions upon exiting. FIG. 7B further illustrates how the diffuser 225 may decrease the velocity and noise of the filtered air exiting the system 200.

FIG. 7B illustrates a schematic of the diffuser illustrated in FIG. 7A. High velocity filtered air 276 may enter the diffuser in a substantially laminar flow pattern. The cross-sectional area of the diffuser 225 increases to expand the filtered air. The filtered air 278 exiting at the expanded cross-sectional area of the diffuser 225 decreases the velocity of the filtered air 278. The filtered air 280 then exits the diffuser through the plurality of vanes 274 shown in FIG. 7A so that the air is pushed in a variety of directions. Thus, the flow of the exiting filtered air 280 is no longer laminar. In this way, the diffuser 225 may reduce the velocity of the filtered air exiting the smoke evacuation system 200 at the outlet port 224, which in turn may reduce the noise of the exiting filtered air 280.

Filter Connection

Figure 8A:
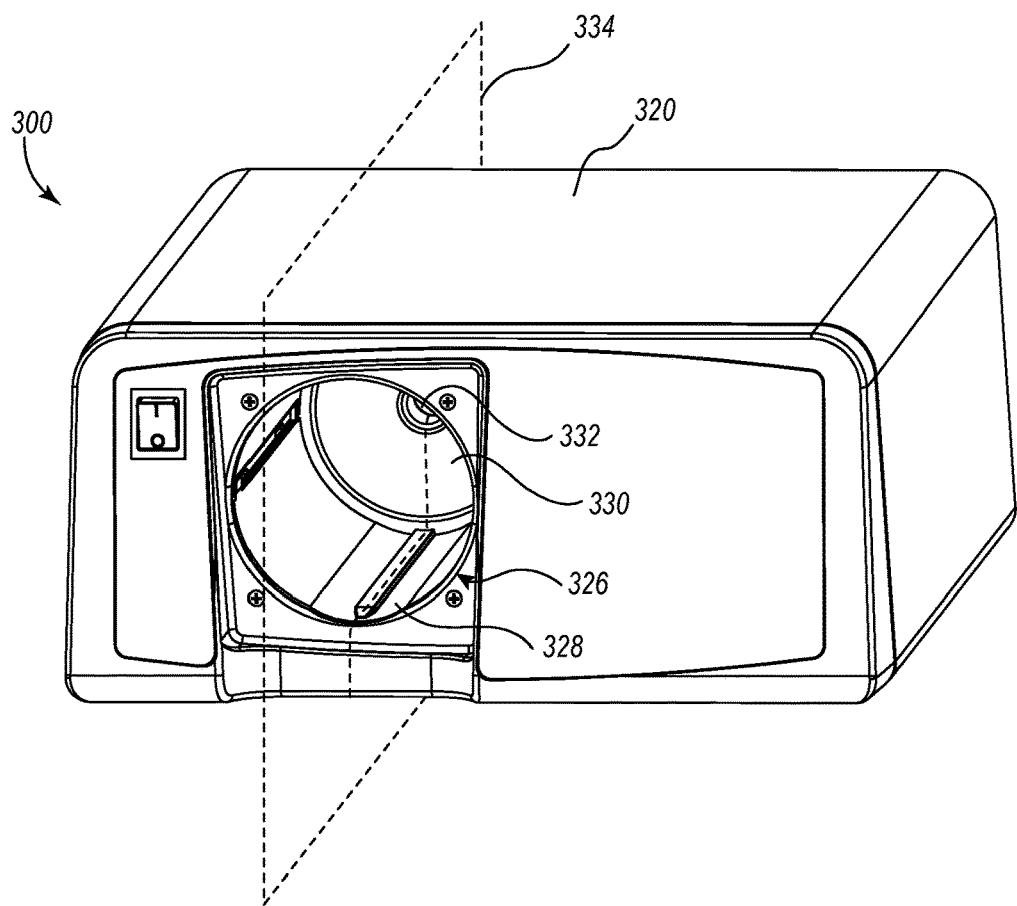
FIG. 8A illustrates a perspective view of an embodiment of a smoke evacuation system.

FIG. 8A illustrates a perspective view of a smoke evacuation system 300. The smoke evacuation system 300 may include a socket 326 configured to receive a filter 306. The filter 306 is not shown in FIG. 3 in order to illustrate the socket 326. The socket 326 may have a first recess 328 and a second recess 332. A transition surface 330 extends between the first recess 328 and the second recess 332. The socket 326 may be shaped to receive a filter 306 into the socket so that the filter 306 fits snuggly into the socket 326.

Figure 8B:
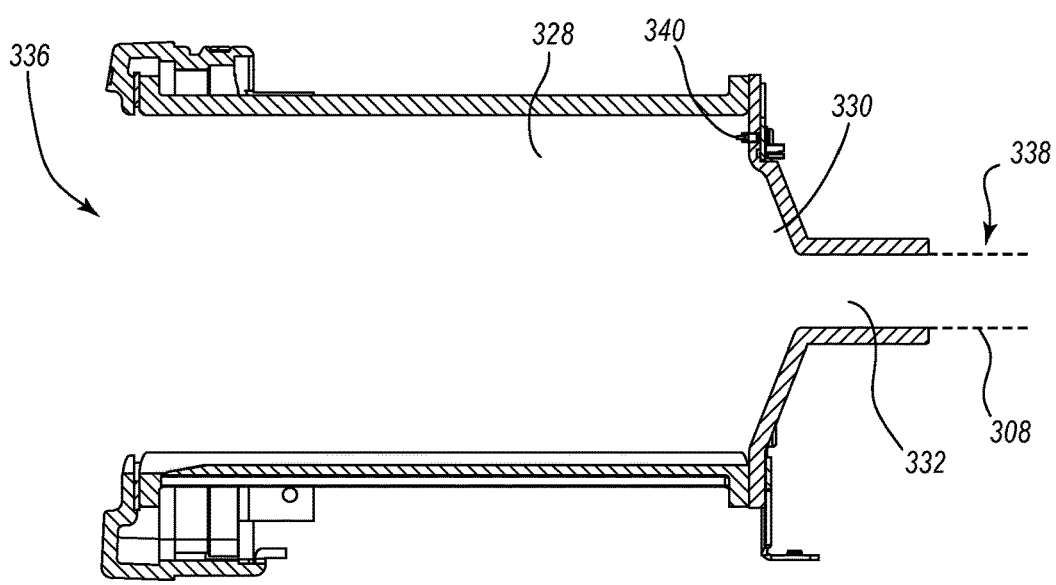
FIG. 8B illustrates a cross-sectional view of the system illustrated in FIG. 8A, wherein an embodiment of a socket is shown.

FIG. 8B illustrates a cross-sectional view of the smoke evacuation system 300 of FIG. 8A. FIG. 8B illustrates a cross-sectional view of plane 334 illustrated in FIG. 8A that passes through the socket 326. As shown in FIG. 8B, the socket comprises a first end 336 that is open to receive a filter 306 and a second end 338 in communication with the airflow path 308. A filter 306 may be inserted and removed from the first end 336 of the socket 326.

The socket 326 may also include a transition surface 330 configured to receive a second end of a filter canister assembly, a second recess 332 configured to receive a connection nipple, and an electronic connector 340. More details regarding filter canister assembly, including the body, second end, connection nipple, and electronic connector will be given hereafter.

Figure 9A:
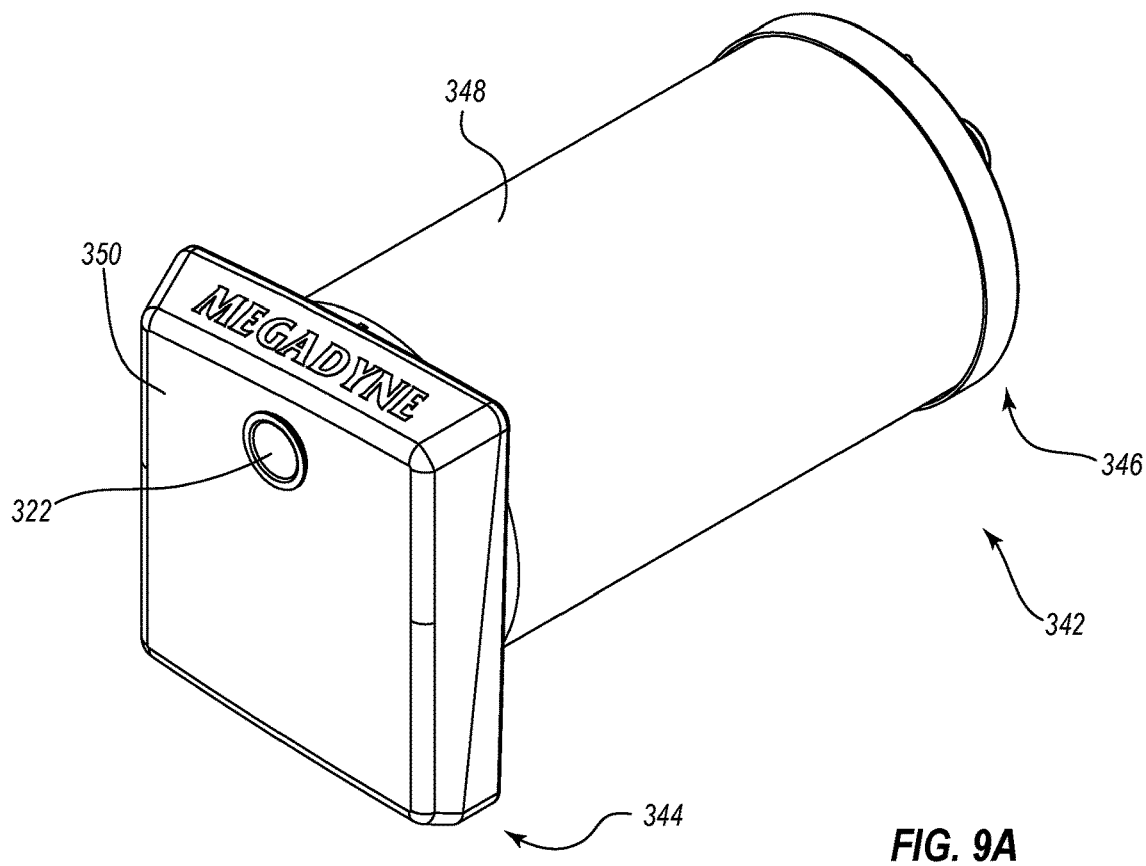
FIG. 9A illustrates a perspective view of an embodiment of a filter canister assembly.

FIGS. 9A through 4C illustrate various views of an embodiment of a filter canister assembly 342. FIG. 9A illustrates a perspective view of the filter canister assembly 342. The filter canister assembly 342 may include a first end 344 and a second end 346. The second end 346 of the filter canister 342 may be at least partially conical. A canister body 348 may be disposed between the first end 344 and the second end 346 of the canister assembly 342. The filter canister assembly 342 may be configured to be inserted into the socket 326 of the smoke evacuation system 300.

A plate 350 may be disposed on the first end 344 of the canister assembly 342 so that the canister assembly 342 may not be inserted too far into the socket 326. When the canister assembly 342 has been fully inserted into the socket 326, the plate 350 makes contact with the outer housing 320 and/or the second end 346 of the canister assembly 342 abuts the transition surface 330 of the socket 326 so that the canister assembly 342 may not be inserted further. The second end 346 and the body 348 of the canister assembly 342 may be able to fit into the socket 326, but the plate 350 may not. The canister assembly 342 may be inserted until the plate 350 comes into contact with the outer housing 320 of the smoke evacuation system 300. The plate 350 may include an inlet port 322 such as the inlet port 322 discussed above with reference to FIG. 2. The vacuum hose 112 illustrated in FIG. 1 may connect to the inlet port 322 so that smoke may travel through the vacuum hose 112 and into the filter canister assembly 342 at the inlet port 322.

Smoke may enter at the inlet port 322 and move through an inner pathway of the filter 306 disposed within the body 348 of the filter canister assembly 342. Potentially harmful and/or unpleasant toxins and particulates may become trapped in the filter 306 as the smoke moves through the filter 306. The filtered gas remaining after filtration may exit the filter canister assembly 342 through the canister outlet 352 illustrated in FIG. 9B. The filter canister assembly 342 may be inserted into the socket 326 of the smoke evacuation system 300 so that the canister outlet 352 communicates with the airflow path 308.

Figure 9B:
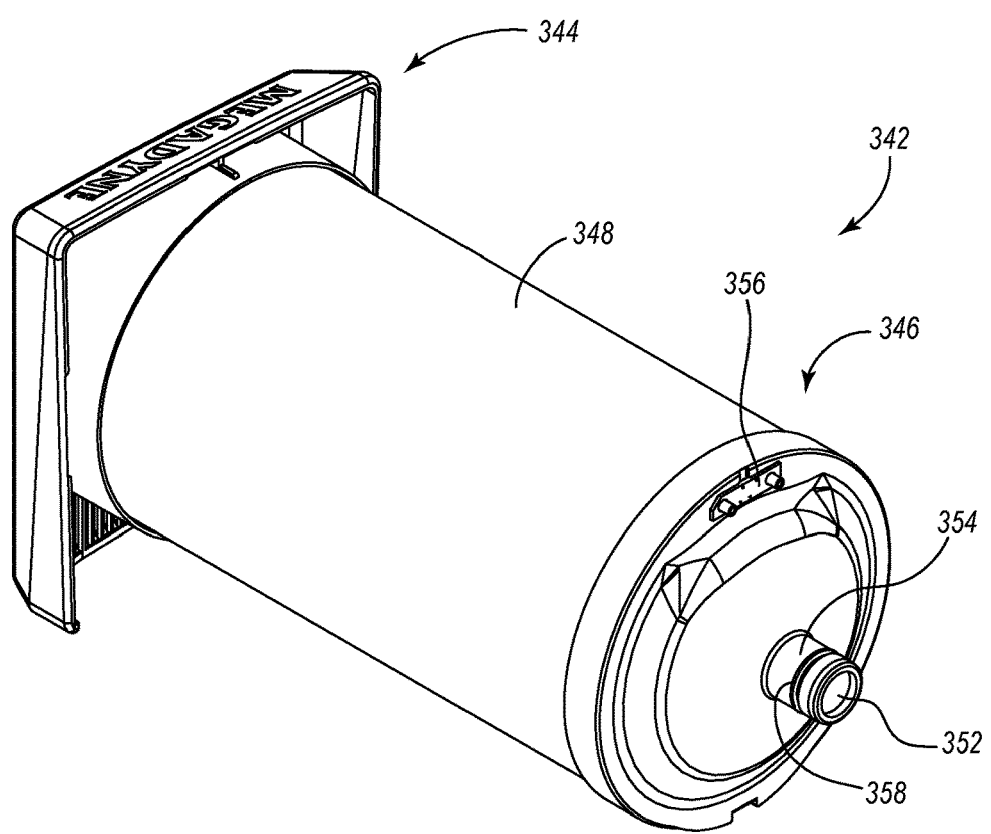
FIG. 9B illustrates a perspective view of an embodiment of a filter canister assembly.

FIG. 9B illustrates a perspective view of the second end 346 of the filter canister assembly 342. The second end 346 may include a connection nipple 354 surrounding the canister outlet 352 and a first electronic connector 356. In one embodiment, the first electronic connector may be an erasable programmable read-only memory (EPROM) connector. The first electronic programmable connector 356 may be a male connector. Other embodiments may include a first electronic programmable connector that is a female connector. The second end 346 of the canister assembly 342 may also include a seal 358 disposed around the connection nipple 354. More details regarding the connection nipple 354, seal 358, and electronic programmable connector 356 will be given hereafter in reference to FIG. 11A and FIG. 11B.

Figure 10B:
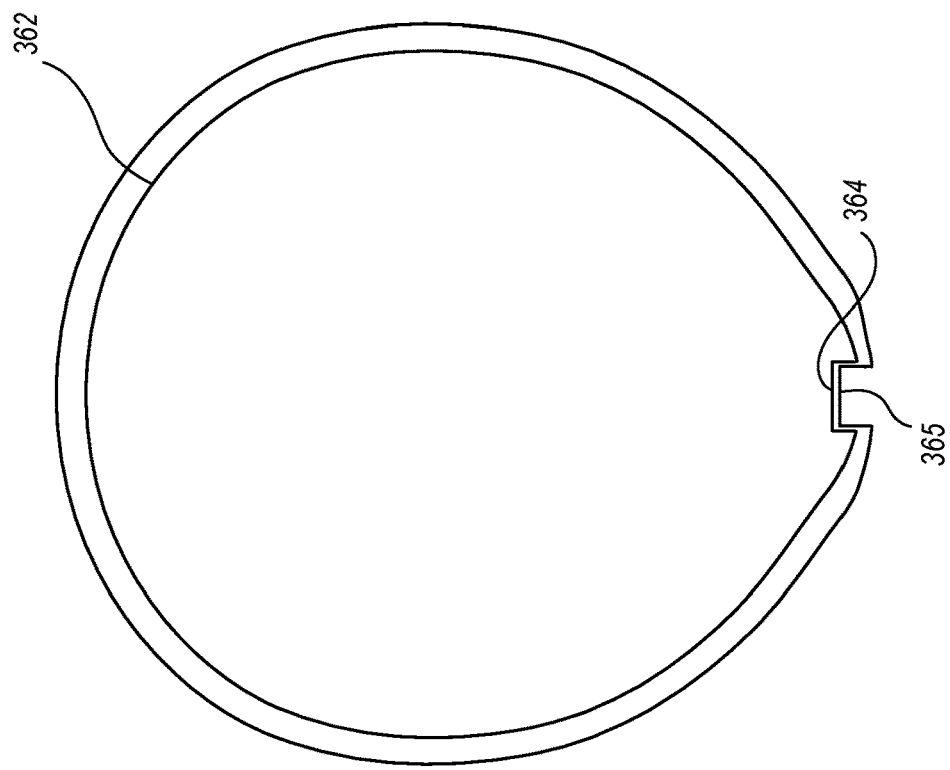
FIG. 10B illustrates a schematic of a cross-sectional shape of one end of a filter canister assembly and an opening of a socket.
Figure 10A:
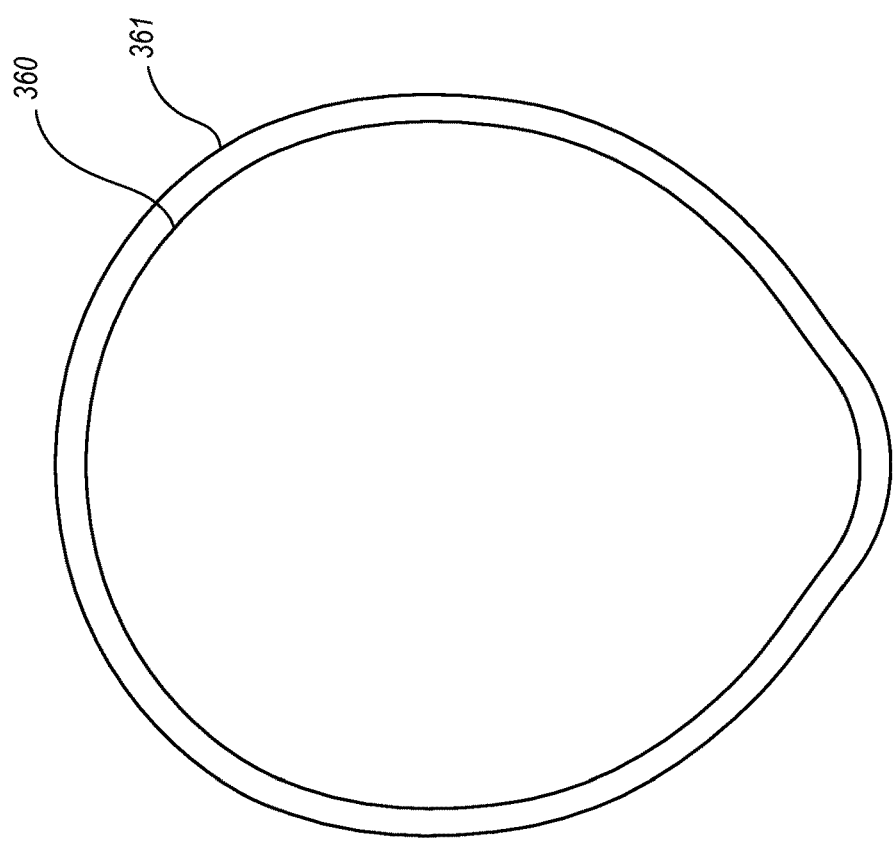
FIG. 10A illustrates a schematic of a cross-sectional shape of one end of a filter canister assembly and an opening of a socket.

FIG. 10A illustrates the cross-sectional shape of the second end of a filter canister 360 and the cross-sectional shape of the first recess of a socket 361. The cross-sectional shape of the second end of the filter canister 360 may be similar to the cross-sectional shape of the first recess of the socket 361 and only slightly smaller so that the filter canister assembly 360 may fit snuggly into the socket 361 when inserted. The cross-sectional shape of the second end of the canister assembly 360 may be slightly smaller than the cross-sectional shape of the first recess of the socket 361 so that the filter canister 360 may be inserted therein.

FIG. 10A illustrates teardrop shaped cross-sections 360, 361. A teardrop cross sectional shape 360, 361 may ensure that the filter canister 360 may only be inserted in a particular orientation so that the filter canister 360 fits into the socket 361. Other embodiments may include cross-sectional shapes that are different from the teardrop shape illustrated in FIG. 10A. Other embodiments may include any other cross-sectional shapes so long as the cross-sectional shape limits the canister assembly 360 to being inserted into the socket 361 in only one orientation.

For example, in one embodiment, the cross-sectional shape 360, 361 may be a triangle having only one line of symmetry. Other embodiments may include other cross-sectional shapes that only have one line of symmetry. Limiting the canister assembly 342 to a single orientation may assure that the filter canister 360 is inserted correctly into the socket 361.

Figure 10C:
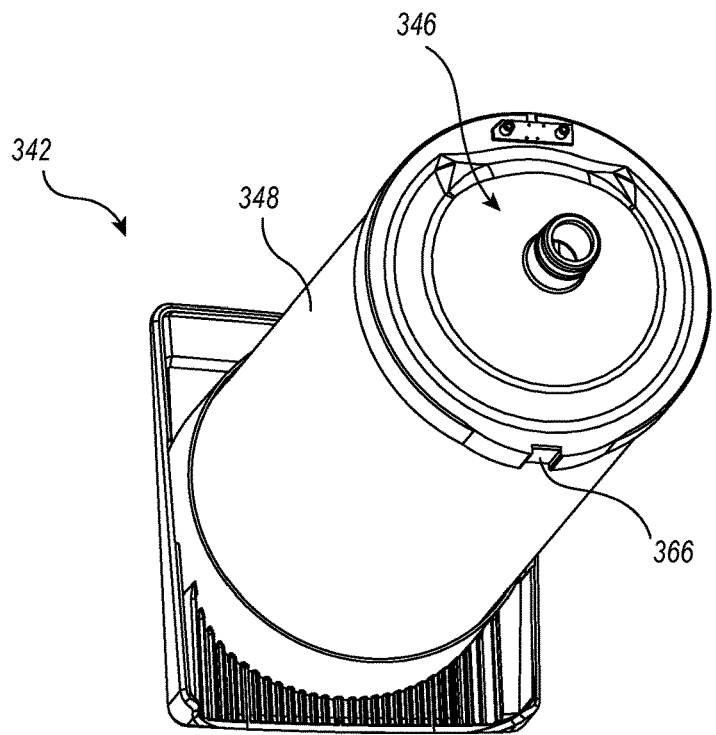
FIG. 10C illustrates a perspective view of an embodiment of a filter canister.
Figure 10D:
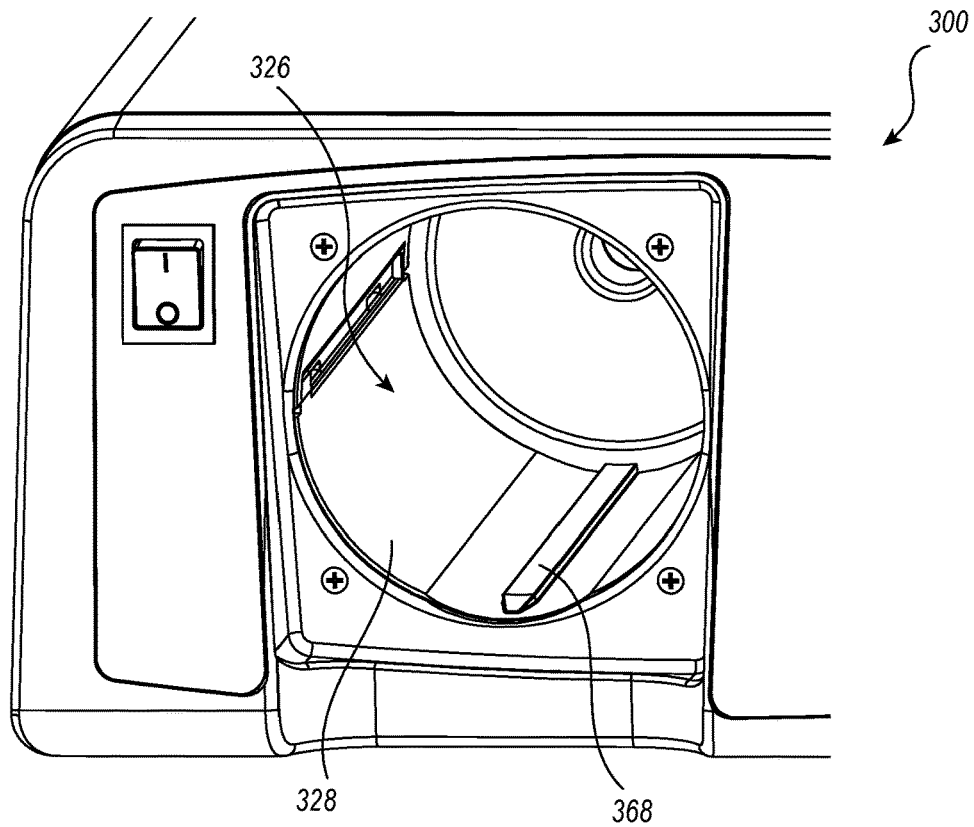
FIG. 10D illustrates a perspective view of an embodiment of a socket of a smoke evacuation system.

FIG. 10B illustrates another cross-sectional shape of a filter canister 362. The shape 362 shown in FIG. 10B is similar to the shape 360, 361 shown in FIG. 10A, except the cross-sectional shape 362 includes a key notch 364. The socket cross-sectional shape has a corresponding key groove 365. FIG. 10C illustrates a canister assembly 342 that includes a second end 346 having a cross-sectional shape 362 as shown in FIG. 10B. FIG. 10D illustrates a smoke evacuation system 300 that includes a socket 326 having a first recess 328 with a cross-sectional shape 362 as shown in FIG. 10B. The key notch 366 of the second end 346 of the canister assembly 342 must align with a key groove 368 of the first recess 328 of the socket 326 in order to be inserted. The key notch 366 and groove 368 may further assure that the canister assembly 342 is properly inserted into the socket 326. Other embodiments of shapes 360 and 362 are contemplated herein. For example, a circular or square shape with a key notch 364 may also be used.

Other embodiments may include more than one key notch 366 and groove 368 at various locations around the cross sectional shape 362 so that multiple key notches 366 and grooves 368 on the canister assembly 342 and socket 326 must be aligned before the canister assembly 342 is inserted into the socket 326. Some embodiments of a canister assembly 342 may also include a body 348 that also has a cross-sectional shape shown in FIGS. 10A and 10B and described herein so that the shape of the body 348 corresponds to the socket 326 when it is inserted.

In some embodiments, the key notch 366 may extend along the whole length of the body 348 of the canister assembly 342 and the key groove 368 may not extend along the whole length of the first recess 328 of the socket 326. In other embodiments, the key notch 366 may extend along the whole length of the body 348 of the canister assembly 342 and the key groove 368 may extend along the whole length of the first recess 328 of the socket 326. In any of the embodiments described herein, the key notch 366 and groove 368 may be configured such that the canister assembly 342 may not be rotated/twisted within the socket 326 once the canister assembly 342 has been inserted into the socket 326.

One of the reasons it is important to ensure that the canister assembly 342 is inserted in the correct orientation is so that the first and second electronic connectors 356, 340 come into contact with each other. In one embodiment, the second electronic connector 340 may be an EPROM connector. The second electronic connector 340 may be disposed within the socket 326 as illustrated in FIG. 8B. The first electronic memory 356 may be disposed at the second end 346 of the canister assembly 342 as shown in FIG. 9B. The first and second electronic connectors 356, 340 may be thus disposed so that when the canister assembly 346 and the first recess 328 of the socket 326 are aligned properly, the first and second electronic connectors 356, 340 meet when the canister assembly 342 is fully inserted into the socket 326.

Figure 11A:
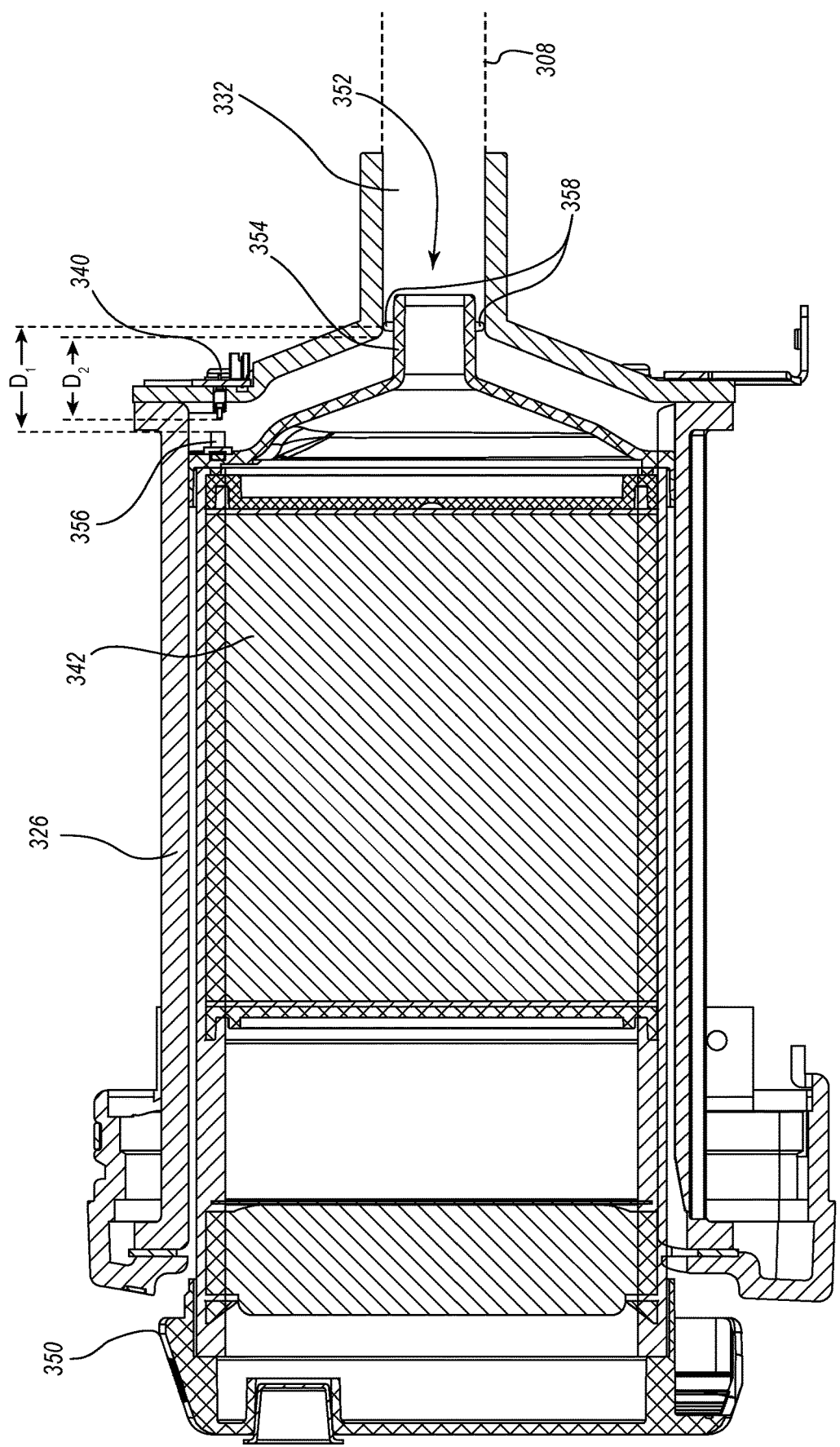
FIG. 11A illustrates a cross-sectional view of a filter canister assembly partially inserted into a socket.

In the illustrated embodiment of FIG. 9B, the first electronic connector 356 is disposed at an upper edge of the second end 346 of the canister assembly 342. This location corresponds to the location of the second electronic connector 340 disposed within the socket 326 as shown in FIG. 11A. Other embodiments may include first and second electronic connectors 356, 340 that are positioned at various locations on the second end 346 of the canister assembly 342 and in the socket 326. Any location is suitable so long as the first and second electronic connectors 356, 340 make contact when the canister assembly 342 is inserted into the socket 326.

Once the first and second electronic connectors 356, 340 contact each other, the electronic memory may relay information to a user or other components of the smoke evacuation system 342 regarding the filter. Such information may include, but is not limited to, the number of times the filter has been used, whether it is the correct filter, whether the filter is still functioning properly, how much life/filtration capacity is left in the filter, and so forth. This connection enables safe, reliable, and efficient use of filters that need to be periodically replaced. The electronic memory may also be used to signal that a filter has been inserted properly and activate the smoke evacuation system 300.

Figure 11B:
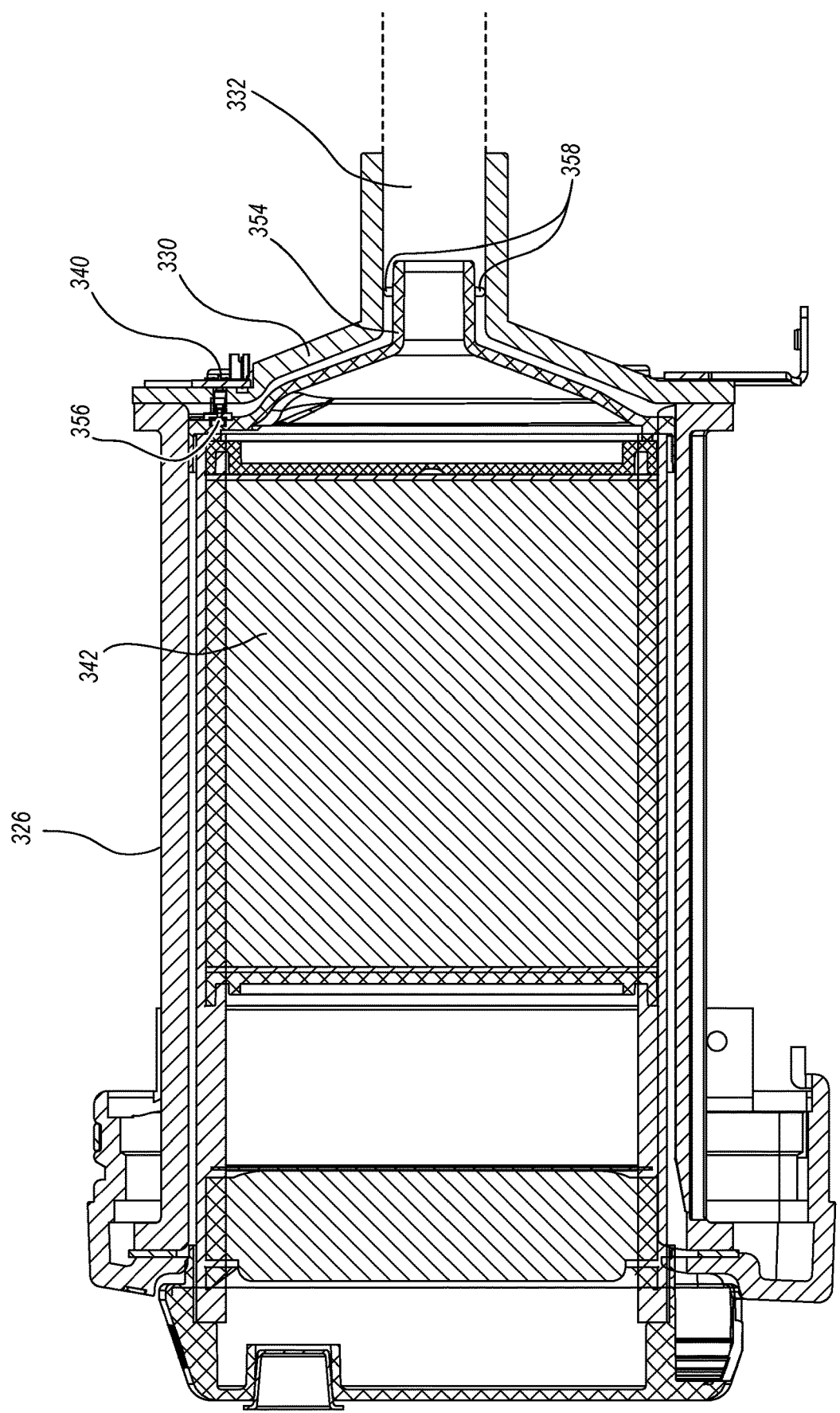
FIG. 11B illustrates a cross-sectional view of a filter canister assembly fully inserted into a socket.

FIGS. 11A and 11B illustrate an embodiment of canister assembly 342 inserted into socket 326. FIG. 11A illustrates canister assembly 342 partially inserted into the socket 326 and FIG. 11B illustrates a canister assembly 342 fully inserted into the socket 326. Referring to FIG. 11A, the canister assembly 342 is partially inserted into the socket 326 so that the connection nipple 354 is received by the second recess 332 of the socket 326. The seal 358 surrounding the connection nipple 354 makes contact with the inner surface of the second recess 332, creating a sealed path for a filtered gas exiting the canister assembly 342 at the canister outlet 352 to enter the airflow path 308 of the smoke evacuation system 300. In one embodiment, the seal 358 may be an O-ring. Other embodiments may include other seals 358.

The seal 358 makes contact with the inner walls of the second recess 332 to create a seal between the connection nipple 354 and the second recess 332 before the canister assembly 342 has been fully inserted into the socket 326. In this partially inserted configuration, the plate 350 does not contact the outer housing 320 of the smoke evacuation system 300 and the first and second electronic connectors 356, 340 do not make contact with one another.

FIG. 11B illustrates a canister assembly 342 fully inserted into the socket 326. When the canister assembly 342 is fully inserted into the socket 326, the seal 358 maintains a seal around the connection nipple 354 within the second recess 332. Additionally, when the canister assembly 342 has been fully inserted into the socket 326, the plate 350 makes contact with the outer housing 320 and/or the second end 346 of the canister assembly 342 abuts the transition surface 330 of the socket 326 so that the canister assembly 342 may not be inserted further. Furthermore, when the canister assembly 342 is fully inserted, the first and second electronic connectors 356, 340 contact one another. The electronic connection may then function as described above.

As discussed above, the electronic connection may activate or allow for activation of the smoke evacuation system 300 so that a suction begins drawing smoke into the filter 306 through the vacuum tube 112. In the embodiments illustrated herein, the seal creates an airtight boundary between the connection nipple 354 and the second recess 332 of the socket 326 before the first and second electronic connectors 356, 340 meet. In other words, the longitudinal distance D1 between the seal 358 and the first electronic connector 356 may be greater than the longitudinal distance D2 between the second recess 332 of the socket 326 and the second electronic connector 340. Longitudinal distances D1 and D2 are labeled in FIG. 11A.

Alternatively, the first electronic connector 356 may be disposed at the first end 344 of the filter canister 342 and the second electronic connector 340 may be disposed at or near the plate 350. In this configuration, the longitudinal distance between the seal 458 and the first electronic connector 356 may still be greater than the longitudinal distance between the second recess 332 of the socket 326 and the second electronic connector 340 so that a seal is created for smoke to pass through into the airflow path 308 before the first and second electronic connectors 356, 340 meet. It will be appreciated that both the first and second electronic connectors 356, 340 may be disposed at various locations on the filter canister 342 and in the socket 326 so long as the relationship between the longitudinal distances mentioned above remain the same.

These configurations ensure that the smoke evacuation system 300 will not be activated until the seal has been created so that filtered gas may not exit the canister outlet 352 until a closed path in communication with the airflow path 308 has been established. These configurations may prevent leakage of filtered gas exiting the canister assembly 342 at the canister outlet 352. These configurations may also ensure that the smoke evacuation system 300 does not begin drawing smoke through the filter 306 until the filter canister assembly 342 is inserted fully and properly into the socket 326.

Figure 12:
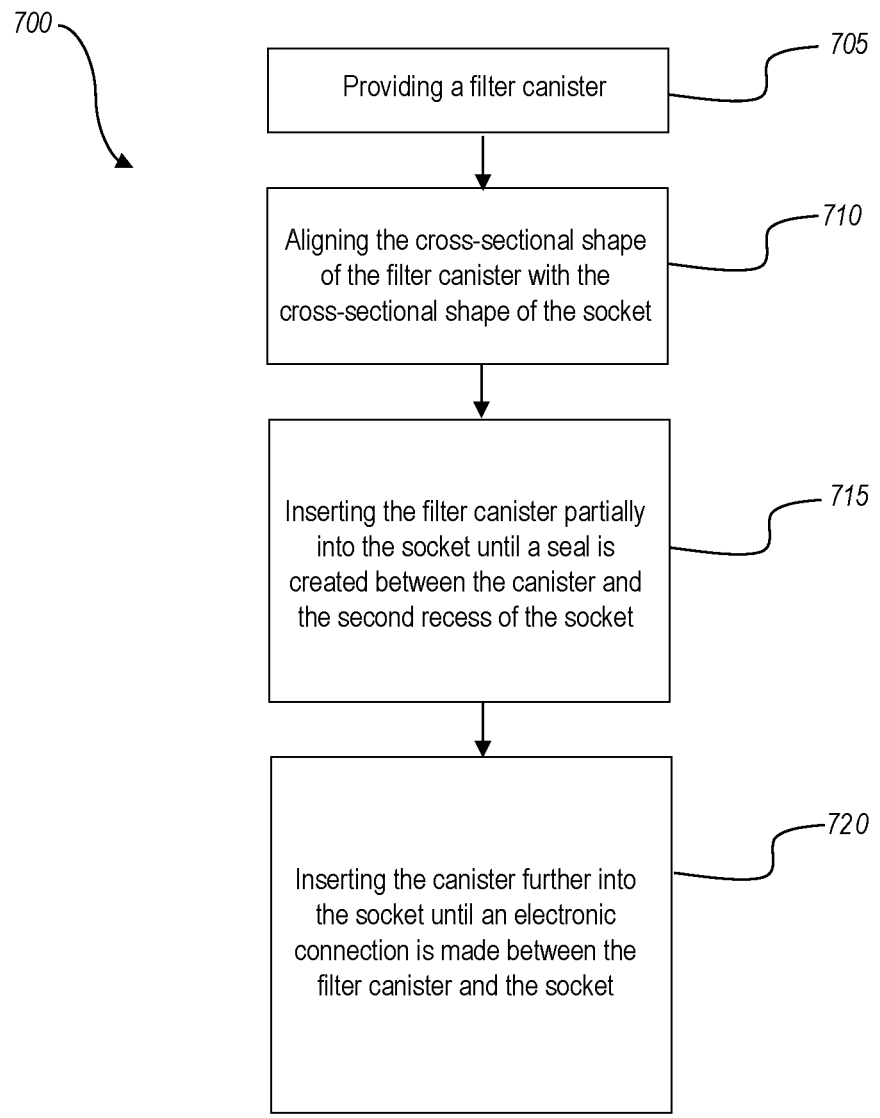
FIG. 12 illustrates a flow chart describing a method for connecting a canister to a smoke evacuation system.

FIG. 12 illustrates a method for connecting a filter canister to a smoke evacuation system 370. In a first step 372, a filter canister is provided. The filter canister may include a body disposed between first and second ends, a connection nipple disposed at the second end, a seal disposed around the connection nipple, a key notch, a cross-sectional shape, and a first electronic connector.

A second step 374 may include aligning the cross-sectional shape of the filter canister with a cross-sectional shape of the socket. The socket may comprise a first recess configured to receive the body of the filter canister, a second recess configured to receive the connection nipple, a transition surface connecting the first and second recesses, and a second electronic connector.

A third step 376 may include inserting the filter canister partially into the socket until the seal creates an airtight boundary between the connection nipple of the filter canister and the second recess of the socket. A fourth step 378 may include inserting the filter canister further into the socket until the second end of the filter canister makes contact with the transition surface of the socket and until the first and second electronic connectors come into contact with one another.

The method of inserting the filter canister described herein creates an airtight boundary between the connection nipple of the canister and the second recess of the socket before the electronic connection is made. In this way, the electronic memory, which may be configured to activate the smoke evacuation system, will not be connected until a sealed path that leads from the connection nipple to the airflow path of the smoke evacuation system has been established. This method may thus prevent filtered gas from leaking out of the filter canister before it is fully installed into the socket of the smoke evacuation system.

Noise and Vibration Management

Figure 13:
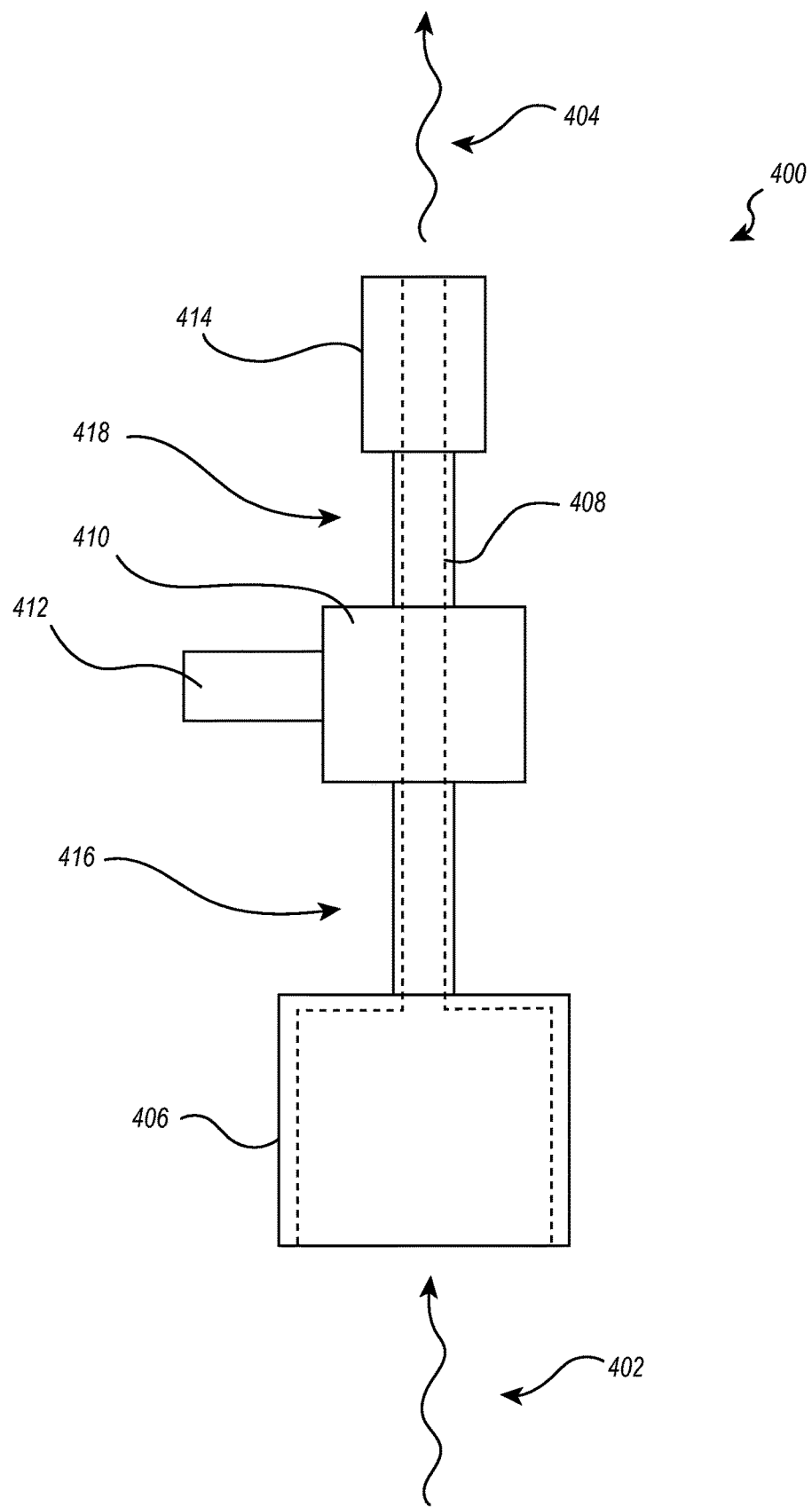
FIG. 13 illustrates a schematic of an embodiment of a smoke evacuation system.

FIG. 13 illustrates a schematic of an embodiment of a smoke evacuation system 400. The smoke evacuation system 400 may include a filter 406 and an airflow path 408. The airflow path 408 may comprise a pump 410 disposed in-line with the airflow path 408 producing a pressure difference within the airflow path 408 by mechanical action. This pressure difference may cause movement of a gas through the airflow path 408.

The airflow path 408 may be at least partially comprised of a tube or other conduit that substantially contains and/or isolates the air moving through the airflow path 408 from air outside the airflow path. For example, the first zone 416 of the airflow path 408 may comprise a tube through which the airflow path 408 extends between the filter 406 and the pump 410. The second zone 418 of the airflow path 408 may also comprise a tube through which the airflow path 408 extends between the pump 410 and the exhaust mechanism 414. The airflow path 408 also extends through the filter 406, pump 410, and exhaust mechanism 414 so that a continuous airflow path 408 extends through the smoke evacuation system 400.

The gas drawn through the airflow path 408 may be smoke 402, or the filtered air remaining after the smoke 402 has passed through the filter 406. A motor 412 drives the pump 410. The smoke evacuation system 400 may also include an exhaust mechanism 414 that may also be disposed in-line with the airflow path 408. The airflow path 408 may extend from the inlet port 245 to the outlet port 250 and pass through the filter 406, pump 410 and exhaust mechanism 414.

Pumps

The pump 410 may cause a suction of smoke 402 that has traveled through the vacuum tube 112 illustrated in FIG. 1 to the filter illustrated in FIG. 13. The smoke 402 may be drawn to the filter 406 via a suction created by the pump 410 as discussed above. The pump 410 may create a pressure difference between a first zone 416 and a second zone 418 of the airflow path 408. This pressure difference causes the smoke 402 to travel into the filter 406, which is disposed at an inlet of the airflow path 408, through the airflow path 408, and out the exhaust mechanism 414, which is disposed at an outlet of the airflow path 408. The filter 406 may extract potentially harmful, foul, or otherwise unwanted particulates from the smoke 402.

The pump 410 may be disposed in-line with the airflow path 408, meaning the gas flowing through the system enters the pump 410 at one end and exits the pump 410 at the other end. The pump 410 may provide a sealed positive displacement airflow path. The pump 410 may produce the sealed positive displacement airflow path by trapping (sealing) a first volume of gas and decreasing that volume to a second smaller volume as the gas moves through the pump 410. Decreasing the volume of the trapped gas increases the pressure of the gas. The second pressurized volume of gas may then be released from the pump at a pump outlet. The pump releases the pressurized outlet gas into the airflow path 408 and on towards the exhaust mechanism 414. More details regarding various embodiments of pumps that may provide a sealed positive displacement airflow path are described herein.

The pump 410 may have more than one operating pressure. The pump 410 may operate at various operating pressures while maintaining a similar flow rate through the airflow path 408. For example, the pump 410 may operate at a first operating pressure resulting in a first flow rate of gas through the airflow path 408. The pump 410 may also operate at a second operating pressure resulting in a second flow rate. The first and second flow rates of gas through the airflow path 408 may be the same or substantially similar regardless of the difference in the first and second operating pressures of the pump 410. For example, if blockage or clogging occurs in the airflow path 408, causing a higher pressure within the path 408, the pump 410 may operate at that higher pressure while still maintaining a constant flow rate of air/gas through the airflow path 408.

The terms "pump" and "sealed positive displacement pump" as used herein may refer to mechanisms that may transfer or cause movement of a gas by mechanical action and substantially increase the pressure of that gas as the gas is moved. For instance, as used herein, a pump may refer to any number of different blowers or compressors. Fans, on the other hand, are not considered "pumps" for purposes of this disclosure. Fans may only operate at a pressure ratio of about 1:1. This pressure ratio does not provide a substantial increase in pressure of the gas being moved.

Figures 14, 15:
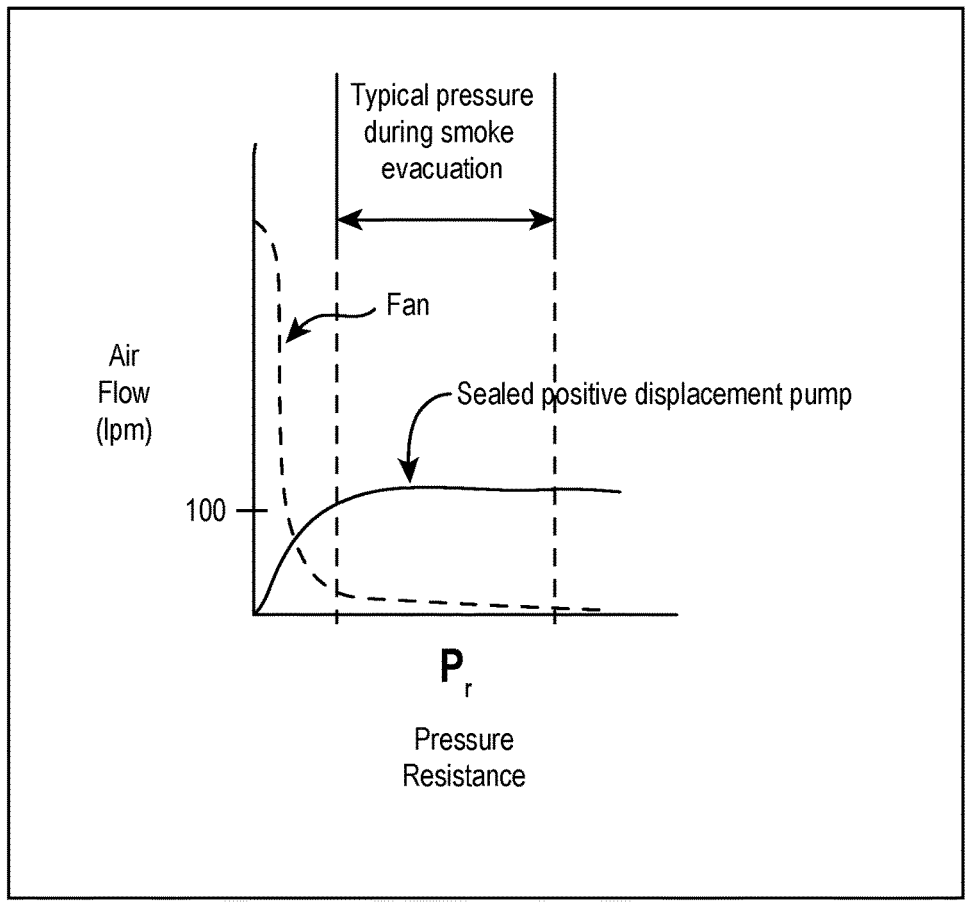
FIG. 14 illustrates resistance pressure vs. air flow for a sealed positive displacement pump and a fan.
FIG. 15 illustrates a table comparing various specifications of a fan, blower, and compressor.

Fans and pumps differ in many respects. A fan may include rotating blades that create a current or flow of gas from one side of the fan to the other. Fans typically operate at a pressure ratio of about 1:1 and move a relatively high volume of air. Typical fans used in smoke evacuation systems may have an operational pressure between atmospheric pressure to about 1.5 psig. The volumetric airflow capacity of a fan decreases dramatically when blockages increase a pressure resistance inside the airflow path 408, as shown in FIG. 14. A sealed positive displacement pump, as described above, is affected less by such blockages and performs well against high resistance pressures, as seen in FIG. 14.

Fans may create suction that draws air through the smoke evacuation system, but they are typically very noisy. The noise can be distracting to practitioners performing surgery. Fans used in typical systems can create sufficient suction but struggle to maintain consistent suction when resistance pressures increase in the system due to airflow obstructions or clogging. Fans are prone to create weak and inconsistent airflow rates through the system.

Blowers differ from fans in that they operate at a higher pressure ratio (e.g., between about 1:1 to 1:2). Essentially, a blower is a high-speed and/or high-volume fan. For example, a blower may be a centrifugal fan that uses rotating impellers to increase the speed and volume of a gas passing through it. Blowers typically have an operational pressure between 1.5 and 1.72 psig and transfer a very high volume of gas relative to fans and compressors.

Compressors are pumps that move relatively low volumes of gas with much higher pressure ratios than fans and blowers. A typical pressure ratio for a compressor, such as those described in various embodiments herein, may be greater than about 2:1. Compressors may operate at a pressure of greater than about 2.72 psig. The various compressors described herein, particularly embodiments that include positive displacement compressors, may be advantageous for a number of reasons. Positive displacement pumps may be much quieter than typical fans used in smoke evacuation systems. Positive displacement pumps also operate well against resistance pressures due to blockages in the airflow path 408 of the smoke evacuation system 400.

Blockages may include unwanted particulate build-up or other clogging due to objects from the ambient air being sucked into the airflow path 408. FIG. 14 illustrates the relationship between pressure resistance and airflow for a positive displacement pump vs. a typical fan. As shown, a sealed positive displacement pump may maintain a relatively steady airflow regardless of the pressure resistance in the system due to clogging. In contrast, the airflow capability of a fan decreases dramatically as the pressure resistance rises. In practice, this indicates that sealed positive displacement pumps, such as the various embodiments described herein, may still create a suction through the smoke evacuation system 400 even when the system clogs or becomes blocked. This is typically not the case if a fan is used.

FIG. 15 is a table showing the pressure increase, operational pressure, pressure ratio, and air volume transferred by a fan, blower, and compressor for comparison. As shown, compressors are able to produce a pressure ratio of greater than 2:1 between a low-pressure gas entering the pump 410 from a first zone 416 of the airflow path 408 and a pressurized gas exiting the pump 410 into a second zone 418 of the airflow path 408.

FIG. 15 also shows the relative air volume moved by the fans, blowers, and compressors. Compressors move the lowest volume of air relative to fans and blowers, and fans move the highest volume of air when air flow path conditions are equivalent. FIG. 15 also shows that compressors operate at a pressure ratio of greater than 2:1, as opposed to fans and blowers that operate at pressure ratios closer to 1:1. This means that air/gas exiting a compressor is typically pressurized at twice the pressure of the air/gas entering the compressor at a compressor inlet.

The various embodiments of the smoke evacuation system, as described herein, may include one or more various types of pumps. The various pumps may be incorporated into the system in order to reduce noise and vibrations, which can be irritating to users and damaging to the system. For example, typical fans used in current systems may be very noisy and cause significant vibrations. These vibrations can cause the system to travel along a surface where it is placed, thus requiring a secure connection to that surface. This secure connection diminishes the portability of the system and increases the difficulty of installation. Vibrations can also be damaging to internal components of the system, which may not be designed to withstand such vibrations.

The following description includes various embodiments of a smoke evacuation system, including various types of pumps, vibration absorption mechanisms, and motor control methods aimed at reducing the noise and vibration of the system in order to solve these problems.

Figure 16A:
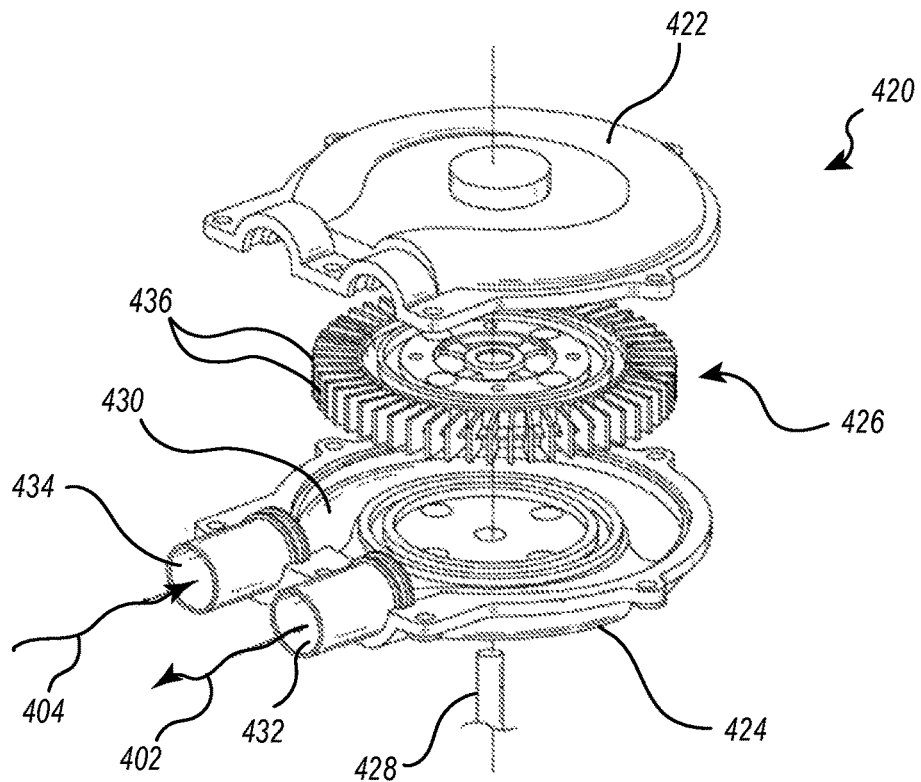
FIG. 16A illustrates an exploded view of a hybrid regenerative blower.
Figure 16B:
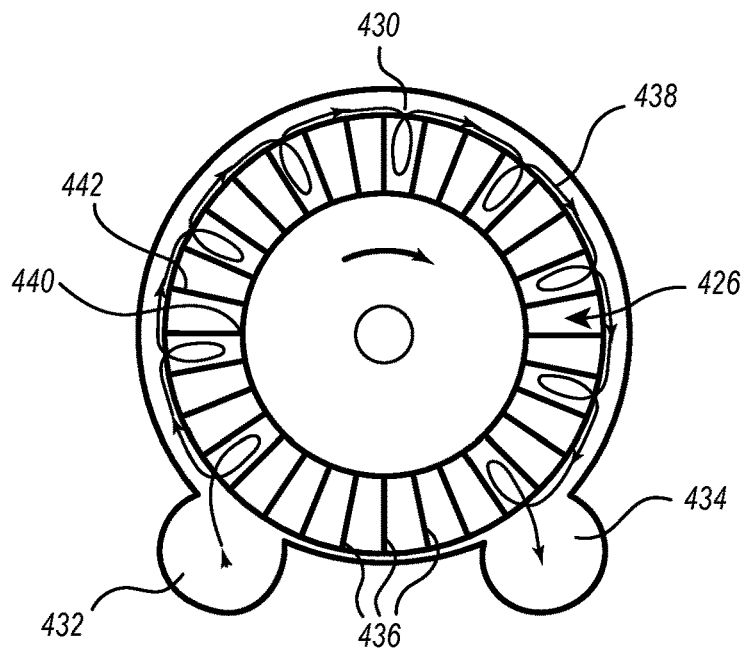
FIG. 16B illustrates a cross-sectional view of the hybrid regenerative blower illustrated in FIG. 16A.

In one embodiment of a smoke evacuation system 400, the pump 410 shown in FIG. 13 may be a blower 420, as illustrated in FIGS. 16A-16B. FIG. 16A illustrates an exploded view of blower 420. The blower 420 may be a hybrid regenerative blower with impeller features that compress the gas 402 passing there through. The blower 420 may include a top cover 422, a bottom cover 424, and an impeller assembly 426. A rotary shaft 428 may be secured to the center of the impeller assembly 426 and cause the impeller assembly 426 to rotate. A motor 412 that may engage the rotary shaft 428 is not illustrated in FIG. 16A, but is shown in FIG. 13.

The top cover 422 may be secured to the bottom cover 424 to create a sealed circulation path 430 having an inlet 432 and an outlet 434. The circulation path 430 may also be referred to as an airflow path 430 of the blower. The impeller assembly 426 may be disposed between the top cover 422 and bottom cover 424 so that the impeller blades 436 reside within the sealed circulation path 430. A motor drives the impeller assembly 426 to rotate about the rotary shaft 428 so that the impeller blades 436 travel in a circular path through the sealed circulation path 430. This circular motion of the impeller blades 436 creates a suction so that a gas 402 is drawn into the inlet 432, travels around the sealed circulation path 430, and exits the blower 420 out of the outlet 434.

FIG. 16B illustrates the flow path 438 of a gas 402 flowing through the sealed circulation path 430 of the blower 420. FIG. 16B illustrates a cross-sectional view of the blower 420 showing impeller assembly 426 inside sealed circulation path 430. The impeller assembly 426 is driven clockwise in this embodiment. As the impeller blades 436 rotate through the sealed circulation path 430, centrifugal force moves gas molecules from the blade root 440 to its tip 442. The gas molecules then leave the blade tip 442 and enter the portion of the sealed circulation path 430 not occupied by the impeller blades 436. The gas molecules are then drawn back down a succeeding impeller blade 436 in repeated fashion.

This repeated flow path 438 of the gas provides a quasi-staging effect that may increase a pressure differential capability of the blower 420. This type of regenerative blower 420 passes the gas through many compression cycles as the gas molecules pass up and down various impeller blades 436 with each revolution of the impeller assembly 426. Thus, a gas exiting the outlet 434 may have a higher pressure than the gas entering at the inlet 432. The speed of the rotating impeller assembly 426 is proportional to the pressure differential of the gas. For example, a higher rotational speed of the impeller assembly 426 increases the pressure differential between the gas at the inlet 432 compared to the gas exiting at the outlet 434. A lower rotational speed results in a lower pressure differential.

The number of impeller blades 436 may be odd so as to limit resonance, which can create noise and vibrations. An odd number of blades 436 reduces the chance of elastic frequencies from the blades 436 becoming tuned to a resonant frequency of the rotary shaft 428. Natural frequencies of the top and bottom covers 422, 424 are also offset from the frequencies of the blades 436 and rotary shaft 428 to limit noise and vibrations of the blower 420 due to the harmonics of the blower 420.

Figure 17A:
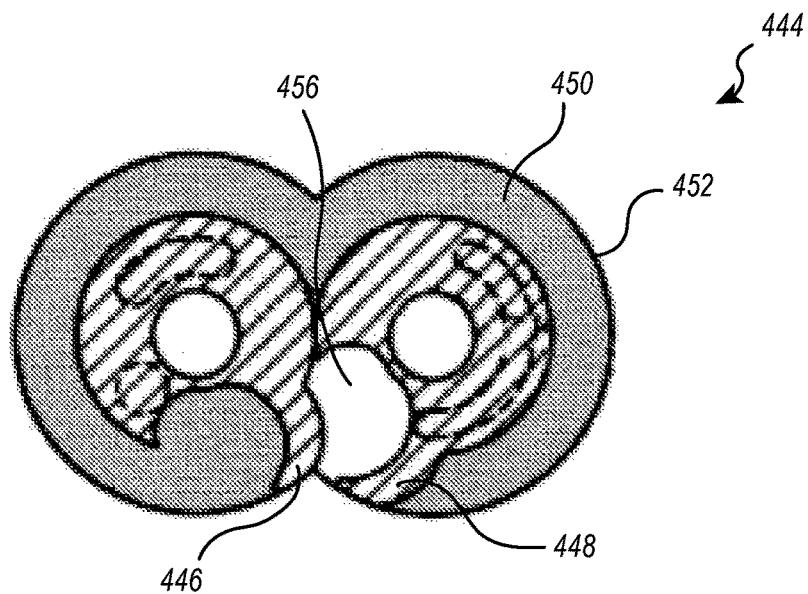
FIGS. 17A through 17C illustrate cross-sectional views of various stages of a claw pump.
Figure 17B:
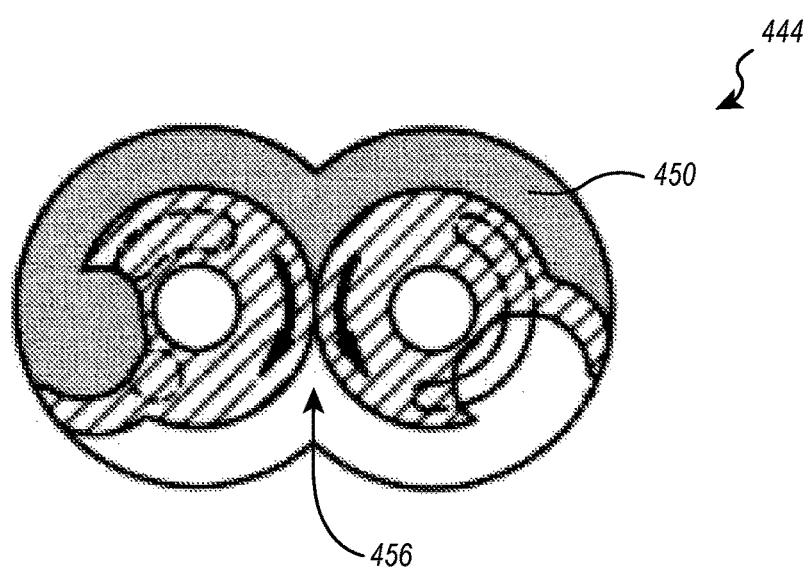
Figure 17C:
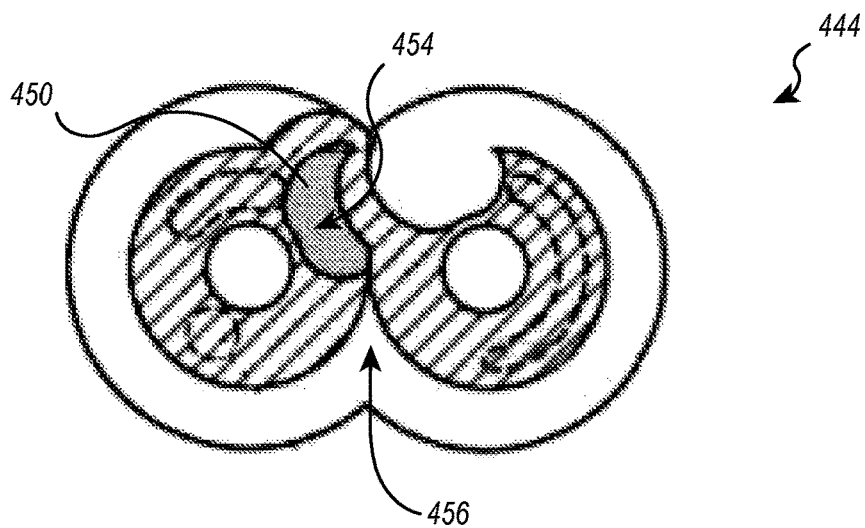

In one embodiment of a smoke evacuation system 400, the pump 410 shown in FIG. 13 may be a claw pump 444. Various cross-sectional views of the claw pump 444 are illustrated in FIGS. 17A-17C. The claw pump 444 may be a cooperative dual drive shaft claw pump. FIGS. 17A-17C illustrate a top cross-sectional view of the claw pump 444 in three different stages of rotation. The claw pump 444 is a positive displacement pump that compresses gas by decreasing the volume of an initial volume of gas that enters the pump.

The claw pump 444 may have first and second counter-rotating rotary elements, or claws 446, 448 disposed within a single circulation path of the pump 444. For example, the first claw 446 may rotate clockwise and the second claw 448 may rotate counter-clockwise, as indicated by the arrows in FIG. 17B. FIG. 17A shows an initial state of the claw pump 444 where a gas 450 resides in a sealed space between the claws 446, 448 and the pump housing 452. The gas 450 is illustrated in gray. As the claws 446, 448 rotate, the volume of the sealed space in which the gas 450 resides decreases due to the geometry of the claws 446, 448. FIG. 17C illustrates the gas 450 in a compressed state, where the volume of the sealed space in which the gas 450 resides has been reduced due to the rotation of the claws 446, 448.

Decreasing the volume of the gas 450 pressurizes the gas. The inlet and outlet ports of the claw pump 444 are not shown in detail because of the top cross-sectional view of FIGS. 17A-17C. An inlet 456 may, for example, be disposed below the claw pump 450 an outlet 454 may be disposed above the claw pump 444 so that the compressed volume of gas 450 shown in FIG. 17C may enter and exit via the inlet 456 and outlet 454 perpendicular to the viewing plane. In other words, the inlet 456 and outlet 454 may be configured so that the inlet 456 is disposed below the viewing plane and the outlet 454 is disposed above the viewing plane, or vice versa, so that the gas travels through the claw pump 444 perpendicular to the viewing plane.

Embodiments of the smoke evacuation system 400 that may include a cooperative dual drive shaft claw pump 444 such as the one illustrated in FIGS. 17A-C may enjoy reduced noise and vibrations. Pumps with single shaft rotary elements may suffer from vibrations due to slight imbalances of components that rotate around a central drive shaft. In the cooperative dual drive shaft claw pump 444 illustrated, the two rotating claws 446, 448 rotate in opposite directions and may balance each other out. This balance may minimize vibrations.

Figure 18A:
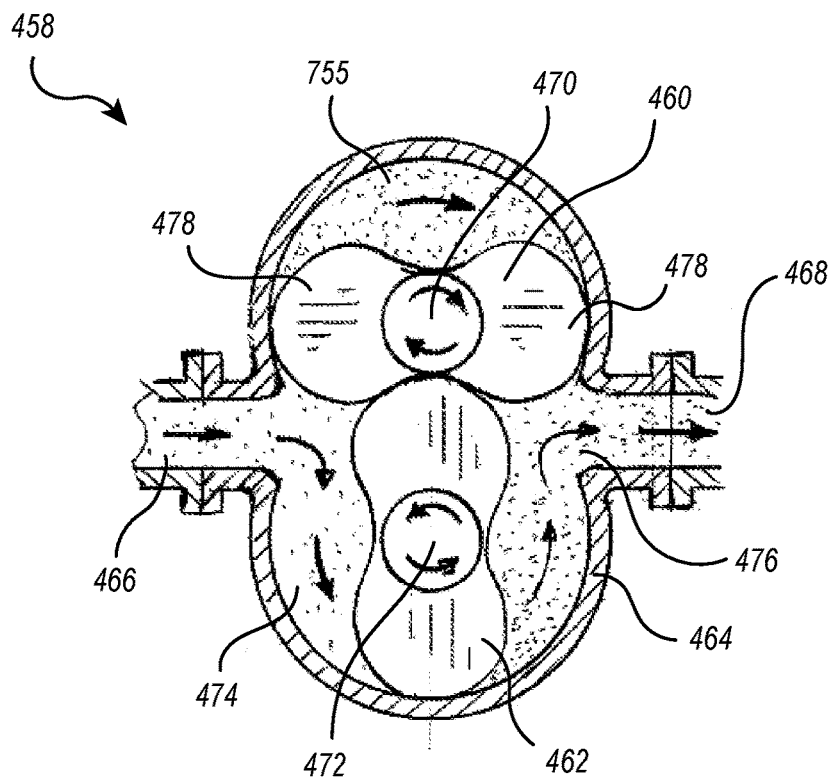
FIG. 18A illustrates one embodiment of a lobe compressor having two lobes.

In one embodiment, the pump 410 of the smoke evacuation system 400 may also be a lobe compressor 458. FIG. 18A illustrates a cross-sectional view of a lobe compressor 458 including two counter-rotating rotary elements 460, 462. Each rotary element 460, 462 may have two or more lobes 478. The lobe compressor 700 functions similarly to the claw pump 444 described herein, in that the two rotary elements 460, 462 rotate in opposite directions, as indicated by the arrows marked on the two rotary shafts 470, 472, in order to create a sealed positive displacement airflow path through the compressor 458.

The rotation of the rotary elements 460, 462 draws in a low-pressure gas 474 through an inlet 466 and moves the gas 474 through the compressor 458 to an outlet 468. As the gas 474 moves through the compressor 458, as indicated by the arrows, the volume of the gas 474 decreases, which pressurizes the gas. The pressurized gas 476 then exits the compressor 458 via the outlet 468.

Figure 18B:
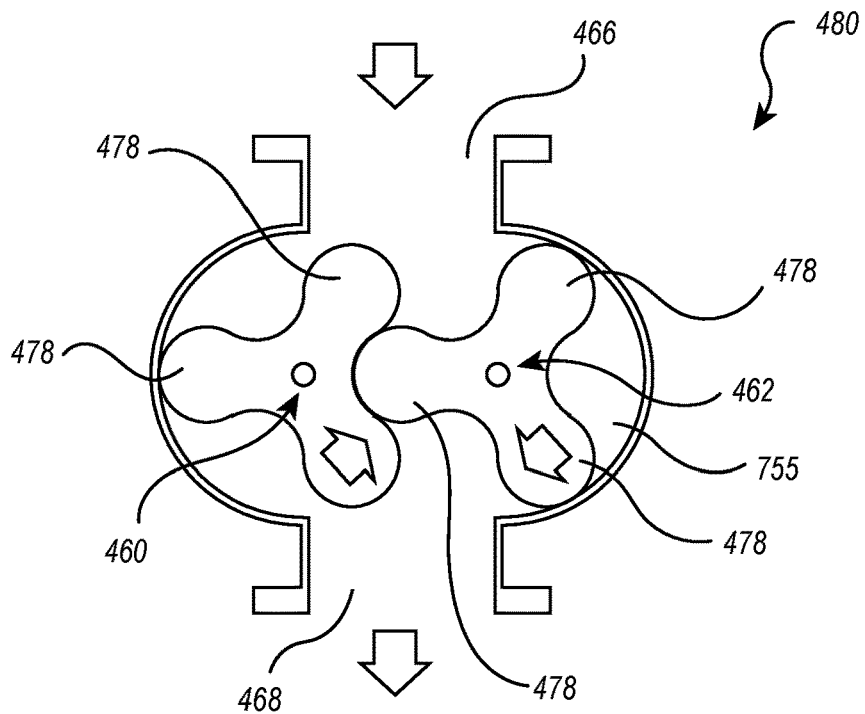
FIG. 18B illustrates one embodiment of a lobe compressor having three lobes.

Other embodiments of the smoke evacuation system 400 may include lobe compressors 700 having more than two lobes 478 on each rotary element 460, 462. For example, FIG. 18B illustrates a lobe compressor 480 that comprises two rotary elements 460, 462 having three lobes 478 each. In this embodiment, a low-pressure gas is drawn into the inlet 466, driven through the compressor 480 via the rotating lobes 478, after which the volume of the inlet gas is reduced and pressurized before it exits out the outlet 468 of the compressor 480.

Figure 18C:
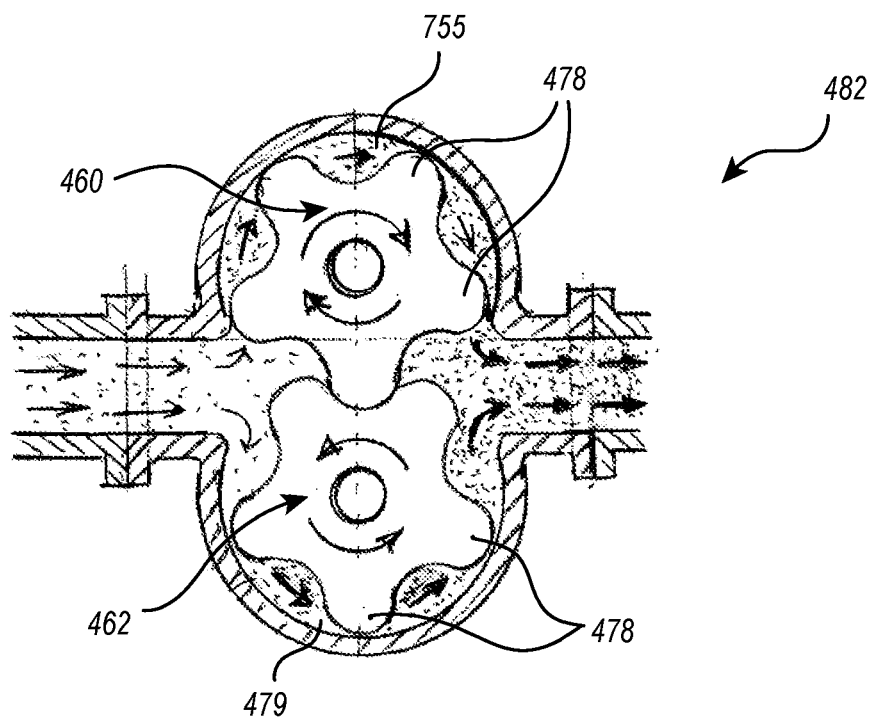
FIG. 18C illustrates one embodiment of a lobe compressor having five lobes.

FIG. 18C illustrates yet another embodiment of a lobe compressor 482 that operates similar to the other lobe compressors described herein. The lobe compressor 482 illustrated in FIG. 18C includes two rotary elements 460, 462 that have five lobes each. Other embodiments may include lobe compressors with rotary elements that have four lobes, or more than five lobes.

In the various embodiments of lobe compressors illustrated in FIGS. 18A-7C, the two rotary elements maintain consistent contact with each other while rotating. For instance, each lobe 478 of one rotary element extends between two lobes of the other rotary element so that contact is maintained as the rotary elements rotate. Thus, air may not escape from between the lobes. Instead, the air is trapped within sealed compartments as the air moves through the lobe compressors.

Other embodiments of a smoke evacuation system 400 may include multiple rotary elements that cooperatively counter-rotate to produce a sealed circulation path that traps and compresses gas by positive displacement action. These other pumps may include, but are not limited to, two stage rotary vane pumps and dual screw eccentric pumps. The various counter rotating dual drive shaft pumps with multiple rotary elements described herein may provide a pressure differential of at least 1.5 psig between a low-pressure inlet gas entering the pump 410 from a first zone 416 of the airflow path 408 and a high-pressure outlet gas exiting the pump 410 into a second zone 418 of the airflow path 408. Other embodiments may include similar pumps that produce a pressure differential of between 1 and 2 psig. Yet other embodiments may produce a pressure differential of greater than 2 psig.

The various counter rotating dual drive shaft pumps with multiple rotary elements may also reduce vibration and noise within the smoke evacuation system 400 for the same reasons as discussed above in reference to the claw pump 444. The two rotary elements rotate in opposite directions and balance each other out. This balance may cancel out vibrations and resulting noise.

In one embodiment of the smoke evacuation system 400, the pump 410 may be a scroll compressor. Scroll compressors are positive displacement compressors. The various embodiments of a scroll compressor described herein may achieve all the advantages of the pumps described above, including but not limited to the same compression ratios, operating pressures, vibration reduction, and noise reduction of the smoke evacuation system 400.

Figure 19:
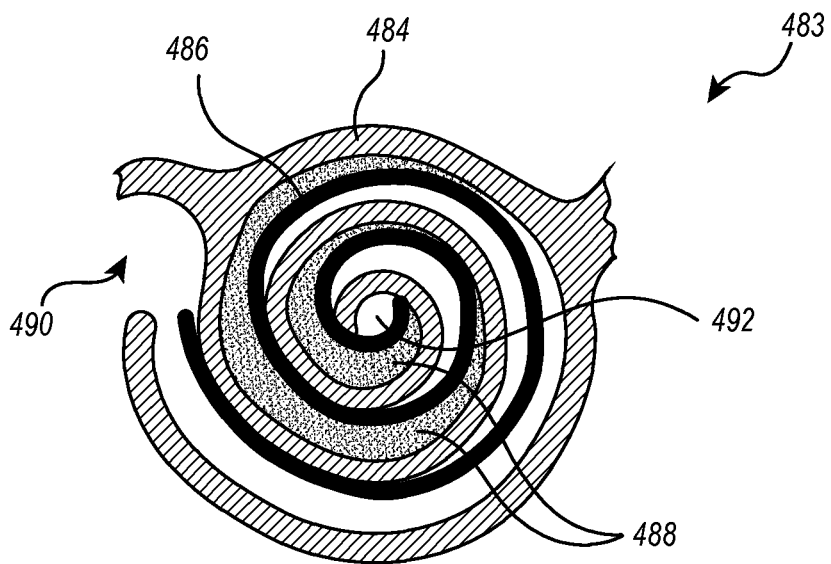
FIG. 19 illustrates a cross-sectional view of on embodiment of a scroll compressor.

FIG. 19 illustrates a cross-sectional view of a scroll compressor 800. The scroll compressor may include a stator scroll 484 and a moving scroll 486. The stator scroll 484 is fixed in position while the moving scroll 486 orbits eccentrically without rotating. The moving scroll 486 may orbit eccentrically such that the moving scroll 486 does not rotate about its own central longitudinal axis, but the central longitudinal axis of the moving scroll 486 would orbit about a central longitudinal axis of the stator scroll 484. The central longitudinal axes of the stator and moving scrolls 484, 486 extend perpendicular to the viewing plane of the scrolls 484, 486. The stator scroll 484 and the moving scroll 486 may be interleaved with each other to form discreet sealed compression chambers 488.

A gas may enter the scroll compressor 483 at an inlet 490. As the moving scroll 486 orbits, the inlet gas is first trapped in a compression chamber 488. The compression chamber 488 moves a discreet volume of gas along the spiral contour of the scrolls 484, 486 toward the center of the scroll compressor 483. The compression chamber 488, or sealed space in which the gas resides, decreases in volume as the gas moves toward the center of the stator scroll 484. This decrease in volume increases the pressure of the gas inside the compression chamber 488. The gas inside the sealed compression chamber 488 is trapped while the volume decreases, thus pressurizing the gas. Once the pressurized gas reaches the center of the scroll compressor 483 it is released through an outlet 492.

Figure 20:
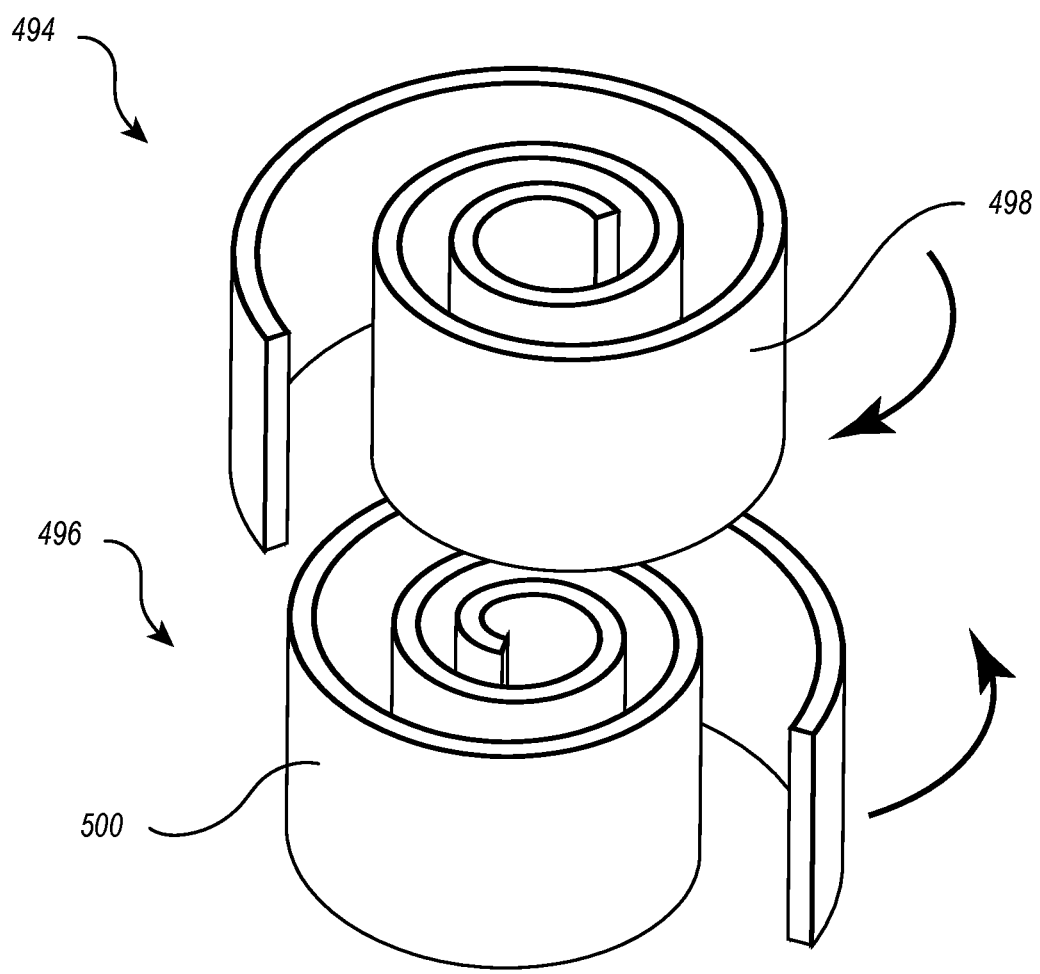
FIG. 20 illustrates one embodiment of a dual, in-line scroll compressor.

Two or more scroll compressors may be disposed in series in order to counterbalance vibrations that may be caused by the orbiting of the moving scroll 486. FIG. 20 illustrates a perspective view of two scroll compressors 494, 496 disposed in series. Only the moving scrolls 498, 500 are shown for illustrative purposes. The first moving scroll 498 may be oriented at 180-degrees from the second moving scroll 500. The first moving scroll 498 of the first scroll pump 494 may orbit in an opposite direction of the second moving scroll 500 of the second scroll pump 496. For example, the first moving scroll 498 may orbit counterclockwise and the second moving scroll 500 may orbit clockwise. Other embodiments may include first and second scroll pumps 494, 496 that are oriented opposite of the scrolls illustrated.

The two scroll pumps 494, 496 may be disposed in series within a sealed airflow path 408. In such a configuration, compressed gas exiting the first scroll pump 494 at an outlet of the first scroll pump 494 may enter an inlet of the second scroll pump 496 to be further compressed. A single scroll pump, such as those described above, orbits eccentrically and therefore inherently shifts its weight around while orbiting to produce vibrations. The opposite orbiting movement of the two scrolls 498, 500 in series, illustrated in FIG. 20, may counterbalance one another in order to limit vibrations in the system 400.

Alternatively, another dual scroll pump embodiment may include two scroll pumps 494, 496 aligned parallel to one another so that parallel flow paths pass through each scroll pump 494, 496. Each scroll pump 494, 496 may have an inlet from a common airflow path 408 and an outlet communicating with a common airflow path 408. Dual scroll pumps 494, 496 aligned parallel in this manner may provide twice as much airflow through the system 400 than other embodiments described herein.

Figure 21A:
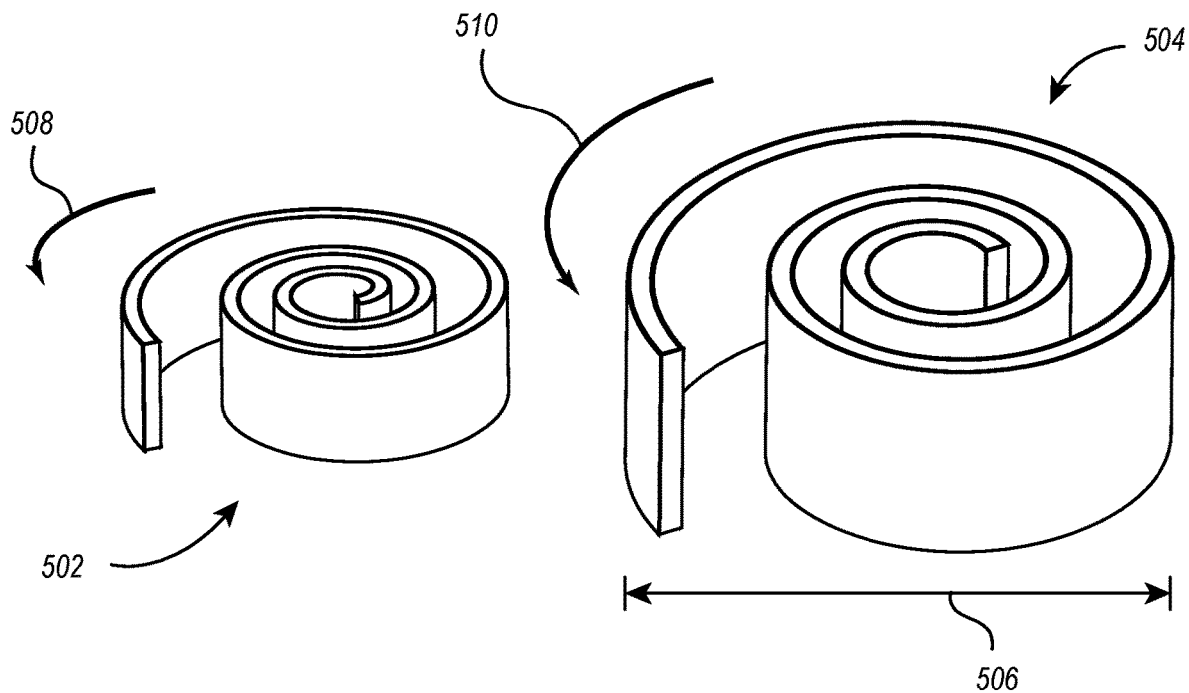
FIG. 21A illustrates one embodiment of a high flow and a low flow scroll.

In one embodiment of the smoke evacuation system 400, the pump 410 may comprise two scroll pumps of different sizes. FIG. 21A illustrates a perspective view of first and second scroll pumps 502, 504. For the sake of simplicity in illustration, stator scrolls of the scroll pumps 502, 504 are not shown. Rather, only the moving scrolls 502, 504 are shown for illustrative purposes. The first scroll 502 may be a low flow-capacity scroll that orbits at a relatively low revolutions-per-minute ("RPM") compared to the other pumps described herein. The second scroll 504 may be a high flow-capacity scroll that also orbits at a relatively low RPM. The high flow scroll 504 may have a higher flow-capacity than the low flow-capacity scroll 502 even when the two are orbiting at the same RPM due to a larger diameter 506 compared to a diameter of the low flow-capacity scroll 502.

The low-flow scroll 502 and the high flow scroll 504 may be disposed in series, as described previously in reference to the dual in-line scroll pump illustrated in FIG. 20. The two scrolls 502, 504 may also be disposed next to each other as illustrated in FIG. 21A. Arrows 508 and 510 indicate the orbiting direction of the low flow and high flow scrolls 502, 504, respectively. FIG. 21A illustrates both scrolls orbiting in a counter-clockwise direction. Other embodiments may include scrolls that orbit clockwise. Yet other embodiments may include scrolls that orbit in opposite directions to one another.

Figure 21B:
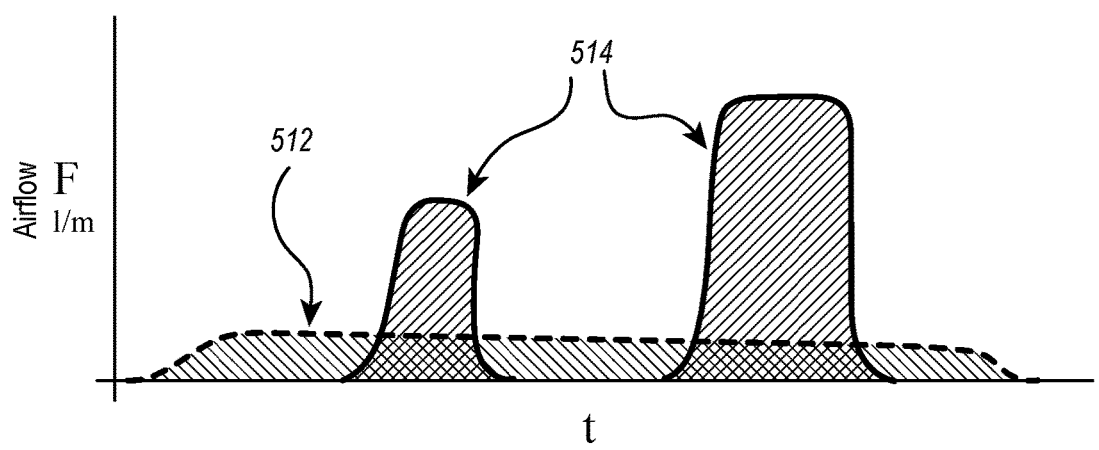
FIG. 21B illustrates the relationship of time vs. airflow for both the low flow scroll and the high flow scroll illustrated in FIG. 21A.

Pairing a low flow scroll 502 with a high flow scroll 504 as described above has a number of advantages. The configuration illustrated in FIG. 21A may allow for variable selectable flow rates without increasing the RPM of the scrolls. For example, as illustrated in FIG. 21B, the low flow scroll 502 may produce a constant low-level airflow 512 over time. The high flow scroll 504 may provide higher flows over time. The high flow scroll 504 may be selectively turned on and off to provide discrete higher flows 514 when needed. Such a need may arise, for example, to overcome a temporarily increased pressure resistance (e.g., due to clogging) within the airflow path 408 of the smoke evacuation system 400.

Thus, variable flow rates can be accomplished while maintaining a low RPM of the orbiting scrolls. Maintaining low RPMs of the scrolls may decrease vibrations and noise of the pump 410.

Vibration Absorption Mechanisms

Components of typical smoke evacuation systems, such as pumps and motors, may create unwanted or even damaging vibrations. Vibrations can damage components of the system or shorten their useful lifespan. Vibrations can even cause components of the system to move across the surfaces on which they rest, requiring that they be fixed to the surface. This decreases the portability of the system and increases the difficulty of installation. Vibration absorption mechanisms may be incorporated into the smoke evacuation system 400 to further limit vibrations. These absorption mechanisms can be used in conjunction with the various pumps described herein, or they may be incorporated separately into various other embodiments of the system 400.

Figure 22:
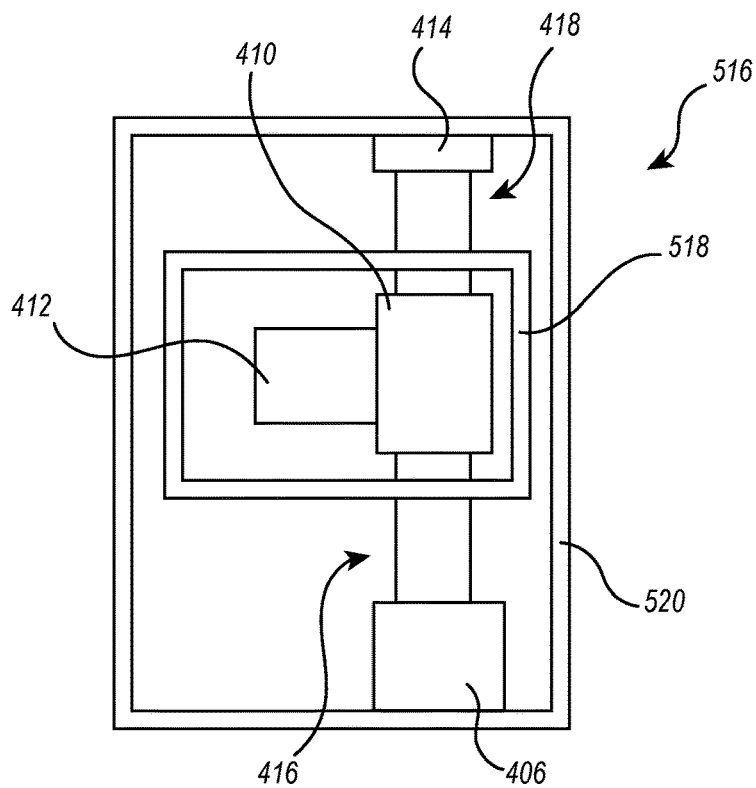
FIG. 22 illustrates an embodiment of a smoke evacuation system including inner and outer housings.

FIG. 22 illustrates in schematic form an embodiment of a smoke evacuation system 516 that includes an inner housing 518 and an outer housing 520. The inner housing 518 may house the motor 412 and pump 410 of the smoke evacuation system 516. In some embodiments, the inner housing 518 may house various other components of the smoke evacuation system 516. For example, the inner housing 518 may house the motor 412, pump 410, and exhaust mechanism 414. Also, for example, the inner housing 518 may only house the pump 410 or the motor 412. In the illustrated embodiment of FIG. 22, the inner housing 518 also includes portions of the first zone 416 and second zone 418 of the airflow path 408 (See FIG. 13).

The first zone 416 of the airflow path 408 may be an inlet to the pump 410 that may pass through the inner housing 518. Likewise, the second zone 418 of the airflow path 408 may be an outlet from the pump that may pass through the inner housing 518 as well. Other embodiments of a smoke evacuation system may include an inner housing 518 that houses all or none of the first and second zones 416, 418 of the airflow path 408.

FIG. 22 illustrates a cross-sectional view of smoke evacuation system 516 in order to show the configurations of the inner and outer housings 518, 520. In some embodiments, the inner housing 518 may completely encapsulate various components of the system 516, such as the pump 410 and the motor 412, thus totally isolating them from other components of the system 516, such as the filter 406 and exhaust mechanism 414. In other embodiments, the inner housing 518 may only partially surround or encapsulate these or other components.

The outer housing 520 may house other components of the smoke evacuation system 516 that are not housed within the inner housing 518. For example, the embodiment illustrated in FIG. 22 shows outer housing 520 that houses the filter 406, exhaust mechanism 414, and portions of the first and second zones 416, 418 of the airflow path 408. The outer housing 520 may also house the entire system, including the inner housing 518 and components therein.

FIG. 22 illustrates a cross-sectional view of a smoke evacuation system 516 in order to show the configurations of the inner and outer housings 518, 520. In some embodiments, the outer housing 520 may completely encapsulate various components of the system 516, such as the filter 406 and the exhaust mechanism 414, thus totally isolating them from an exterior environment surrounding the system 516. The outer housing 520 may also encapsulate the inner housing 518. The outer housing 520 may completely encapsulate components of the smoke evacuation system 516 not encapsulated by the inner housing 518, such as the filter 406 and exhaust mechanism 414. In other embodiments, the outer housing 520 may only partially surround or encapsulate these or other components.

Figure 23:
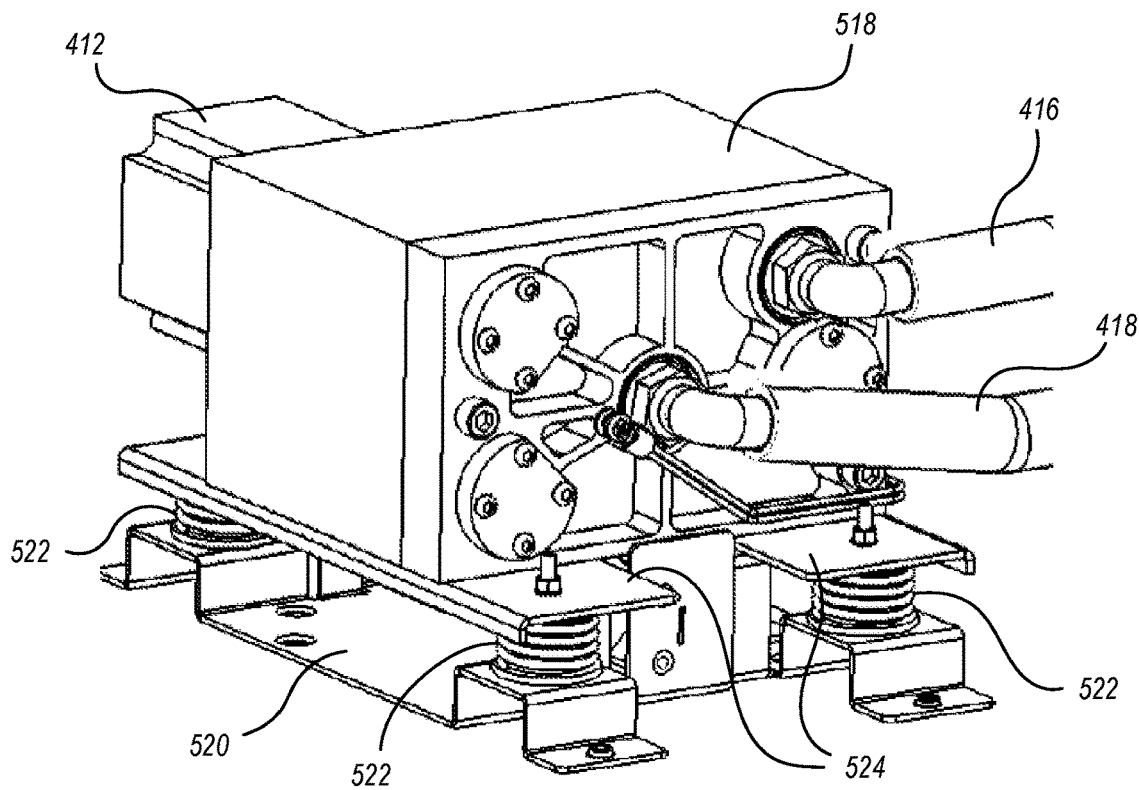
FIG. 23 illustrates on embodiment of vibration absorption mechanisms disposed between inner and outer housings.

Vibration absorption mechanisms may be disposed, and serve as interfaces, between the inner and outer housings 518, 520. FIG. 23 illustrates an inner housing 518 interfacing with an outer housing 520 via various vibration absorption mechanisms 522. Only a portion of the outer housing 520 is shown for illustrative purposes. Various components of a smoke evacuation system 400 are also shown, including first and second zones 416, 418 of the airflow path 408, which may serve as an inlet and outlet of the pump disposed within inner housing 518. The filter 406 (illustrated in FIG. 22), motor 412, and first and second zones 416, 418 of the airflow path 408 may be disposed within the outer housing 520 but outside the inner housing 518. The pump 410 may be enclosed inside the inner housing 518 and therefore not shown in FIG. 23.

In the embodiment illustrated in FIG. 23, vibration absorption mechanisms 522 may comprise springs disposed between inner and outer housings 518, 520. The pump and/or motor enclosed/housed within the inner housing 518 may create vibrations that result in unwanted movement or noise of the system. The vibration absorption mechanisms 522 may absorb these vibrations so that a substantial portion of the vibrations are not transferred to the outer housing 520.

For example, the springs 522 illustrated in FIG. 23 may compress, stretch, or laterally flex due to vertical or horizontal vibrational forces acting on the springs 522. These forces may be a result of the inner housing 518 vibrating up and down, or laterally. These movements caused by the vibrating motor and/or pump within the inner housing 518 may be transferred into the springs 522. As the springs 522 compress, stretch, or laterally flex, the spring may absorb a substantial portion of the vibrations. Thus, the vibrations may not be substantially transferred from the inner housing 518 to the outer housing 520.

FIG. 23 illustrates an embodiment wherein four vibration absorption mechanisms 522 are disposed between the inner housing 518 and the outer housing 520. Other embodiments may include more or less than four vibration absorption mechanisms 522 disposed between the inner housing 518 and the outer housing 520. The location of the vibration absorption mechanisms 522 may also vary in other embodiments. For example, a vibration absorption mechanism 522 may be disposed at the bottom center of the inner housing 518, rather than just at the bottom four corners of the inner housing 518 as illustrated.

In the embodiment illustrated in FIG. 23, a number of plates 524 may be secured to or integrally formed with the inner housing 518 and the vibration absorption mechanisms 522 may be secured directly or indirectly to the plates 524. Other embodiments may or may not include plates 524. For example, other embodiments may have vibration absorption mechanisms 522 that are secured directly to the inner housing 518. Other embodiments may include more or less than two plates 524 secured to both the inner housing 518 and vibration absorption mechanism 522 as illustrated in FIG. 23.

FIG. 24A shows an inner housing 518 secured to an outer housing 520 via plates 524 and vibration absorption mechanisms 526. The vibration absorption mechanisms 526 of the embodiment illustrated in FIG. 24A may be ring isolators 526. Similar to the springs 522 disposed between the plates 524 and outer housing 520 illustrated in FIG. 23, the ring isolators 526 may absorb vibrations from the pump 410 and/or motor 412 housed within the inner housing 518 so that a substantial portion of those vibrations are not transferred to the outer housing 520.

FIG. 24B illustrates how the ring isolators 526 may be secured to the housings 518, 520 and/or plates 524. The ring isolators 526 may be configured in a circular ring shape and be disposed between the plate 524 and outer housing 520 so that the ring isolator 526 acts as a barrier between the two, as illustrated in FIGS. 24B and 24C. Two or more securing mechanisms 528 may secure the plate 524 and outer housing 520 to the ring isolator 526 on opposing sides of the ring isolator 526 as shown. The securing mechanisms 528 illustrated in FIGS. 24B and 24C comprise a nut and bolt assembly. Other embodiments may include other securing mechanisms 528. For example, other embodiments may include securing mechanisms 528 that comprise nails, screws, adhesives, clips, hooks, and the like.

FIG. 24C illustrates how a ring isolator 526 may absorb vibrations. The ring isolator may be comprised of a flexible material such as an elastomer. For example, one embodiment of the ring isolator 526 may be made of silicone. Other embodiments may include ring isolators 526 that comprise other elastomeric materials, such as rubber. The ring isolator 526 may flex when acted upon by a force, such as the forces created by vibrations 530. FIG. 24C illustrates vibrations 530 pushing down on the plate 524. These vibrations 530 push down on the plate 524, which pushes down on the ring isolator 526, which may cause the ring isolator 526 to flex in such a way so as to compress the ring isolator 526. The compressed ring isolator 526 may absorb the movement of the plate 524 due to the vibrations 530 without transferring a substantial portion of that movement into the outer housing 520.

Vibrations 530 may be oscillatory movements that create forces that may push downward, pull upward, or pull sideways on the plate 524. As will be appreciated, the ring isolator 526 may absorb all of these potential movements of the plate 524 by deforming and/or flexing in all different directions. For example, the ring isolator 526 may expand and stretch taller, or shift side to side in response to various vibrational forces. In this way, ring isolators 526 may absorb the vibrations 530 of the inner housing 518 so the vibrations 530 are not substantially transferred to the outer housing 520.

FIG. 25A illustrates an embodiment where the vibration absorption mechanism comprises an elastomeric sheet 532. The elastomeric sheet 532 may be disposed between the plates 524 and outer housing 520 similar to the springs 522 and ring isolators 526 described herein. The elastomeric sheet 532 may be a single sheet covering an entire area between the first housing 518 and the second housing 520 as shown in FIG. 25A. Other embodiments may include multiple sheets 532. For example, in one embodiment, the sheet 532 may comprise four separate sections disposed at the four bottom corners of the inner housing 518 and/or plates 524, similar to where the ring isolators 526 are disposed according the embodiment illustrated in FIG. 24A. Other embodiments may include two separate sheets 532, each connecting two corners of the inner housing 518 and/or plates 524 to the outer housing 520.

FIG. 25B shows one way in which the elastomeric sheet 532 may be secured between the plate 524 and the outer housing 520. In the illustrated embodiment, two nuts molded into the sheet 532 provide a fixture through which two screws/bolts may be threaded from above the plate 524 and below the outer housing 520. Other embodiments may include other securing mechanisms, such as nails, hooks, adhesives, and so forth. Once secured, the sheet 532 may absorb vibrations from the inner housing 518 due to the pump 410 or motor 412 and substantially prevent those vibrations from being transferred to the outer housing 520.

In addition to the various vibration absorption mechanisms described herein, additional vibration absorption mechanisms may be employed in conjunction with those described in other embodiments. FIG. 26 shows a tube configuration that may enhance the vibration absorption capabilities of various tubes. More specifically, FIG. 26 shows bent tubes 536, 537 that may absorb vibrations due to their bent configuration. The tubes 536, 537 may be inlet and/or outlet tubes to the pump 410 residing within the inner housing 518. The motor 412 may be disposed outside the inner housing 518 and engage the pump 410 through the housing 518. The motor 412 and/or pump 412 may create vibrations in the system that may travel into the inner housing 518 and through the tubes 536, 537.

The tubes 536, 537 may include a U-shaped portion 538 at one or more locations along the length of the tubes 536, 537. The U-shaped portions 538 of the tubes 536, 537 may allow the tubes 536, 537 to flex in response to vibrations to a greater degree than straight tubes having no U-shaped portions 538. The U-shaped portions 538 of the tubes 537 also may increase the total length of the tubes 536, 537 to increase the amount of tube material available to absorb and dampen vibrations. In the embodiment shown in FIG. 26, each tube 536, 537 has one U-shaped portion 538. Other embodiments may include more than one U-shaped portion 538. Some embodiments may include tubes 536, 537 bent into other shapes, such as S-shaped portions or the like.

The U-shaped portions 538 of the tubes 536, 537 may be made of material that is the same or similar to the rest of the tubes 536, 537. Some embodiments may include U-shaped portions 538 that are made of a different material than the rest of the tubes 536, 537. For example, some embodiments may include U-shaped portions 538 that are made of an elastomeric material. A U-shaped portion 538 made of an elastomeric material, for example rubber, may absorb vibrations to a greater degree than more rigid materials such as plastics and the like.

Three different configurations of tubes 540 configured to absorb vibrations are illustrated in FIGS. 27A through 27C. FIG. 27A illustrates a tube 540 having a flexible portion 542. The flexible portion 542 may be made of an elastomeric material such as silicone, rubber, or the like. FIG. 27B illustrates a tube 540 that includes a U-shaped portion 544 similar to those U-shaped portions 538 illustrated in FIG. 26. The U-shaped portion 544 may be made of material similar to the rest of the tube 540 or it may be made of elastomeric material such as silicone, rubber, or the like. FIG. 27C illustrates a tube 540 that includes 90-degree bent portions 546, in order to accomplish the same vibration absorption capacity of the tubes 540 described above. Again, the bent portions 546 may be made of material similar to the rest of the tube 540 or may be made of elastomeric material such as silicone, rubber, or the like.

In addition to the absorption mechanisms described above, which may be disposed between the inner housing 518 and outer housing 520, additional absorption mechanisms may be disposed on an outside surface of the outer housing 520. The smoke evacuation system 400 may be placed on a support surface, such as a table or countertop when in use. Vibration of the outer housing, due to the operation of internal components of the system 400 such as the motor 412 and/or pump 410, may cause the entire system 400 to bounce/travel along the support surface.

Additional vibration absorption mechanisms may be disposed on a bottom outside surface of the outer housing 520 to act as an interface between the smoke evacuation system 400 and the support surface on which the outer housing 520 is placed in order to reduce this effect. The vibration absorption mechanisms may act to absorb the vibrations so the vibrations are not substantially transferred to the support surface. The vibrations absorption mechanisms may also provide greater friction between the outer housing 520 and a support surface to reduce travel along the surface due to vibrations.

Figure 28A:
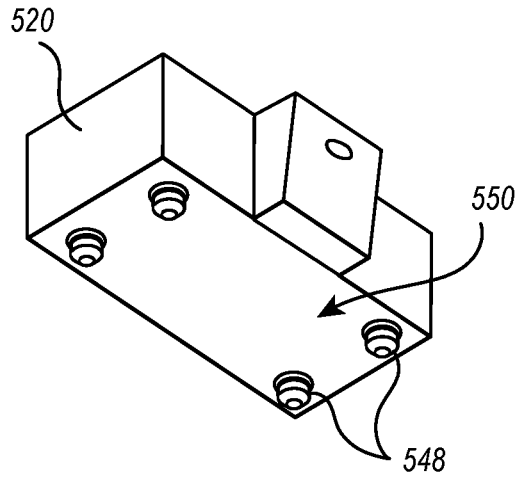
FIG. 28A illustrates one embodiment of a vibration absorption mechanism.

FIG. 28A shows an outer housing 520 that includes a number of feet 548. These feet 548 are vibration absorption mechanisms. The feet 548 are disposed on a bottom surface 550 of the outer housing 520 and may act as an interface between the outer housing 520 and a support surface on which the outer housing 520 is placed. The embodiment illustrated in FIG. 28A includes four feet 548 disposed on the bottom surface 550. Other embodiments may include more or less than four feet 548 that may be arranged in any number of configurations. For example, one embodiment may include only three feet 548. Other embodiments may include five or more feet 548 with some of the feet 548 disposed near the center of the bottom surface 550 as well as the corners.

Figure 28B:
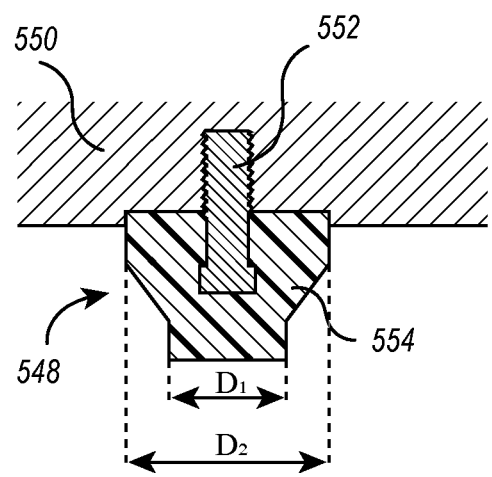
FIG. 28B illustrates a cross-sectional view of one of the vibration absorption mechanisms illustrated in FIG. 28A.

FIG. 28B illustrates a cross-sectional view of one of the feet 548 illustrated in FIG. 28A. The foot 548 may be comprised of a flexible matrix 554 secured to the bottom surface 550 via a rigid or semi-rigid bolt 552. The bolt 552 may be threaded or otherwise secured to the bottom surface 550. The bolt 552 may protrude beyond the bottom surface 550 and the flexible matrix 554 may be molded around the protrusion of the bolt 552.

The flexible matrix 554 of the foot 548 may have a first diameter $D_1$ and a second diameter $D_2$. The first diameter $D_1$ and the second diameter $D_2$ may vary in size. The first diameter $D_1$ may be smaller than the second diameter $D_2$. A contact pressure between the foot 548 and a support surface may increase as the diameter of the foot 548 decreases. Also, certain diameters may absorb a given range of vibrational frequencies better than others. It may therefore be advantageous to vary the diameter of the foot 548 as shown in FIG. 17B.

For example, $D_1$ may absorb a first frequency of vibrations, or first range of frequencies, and $D_2$ may absorb a second frequency of vibrations, or second range of frequencies. Therefore, having a foot 548, such as the foot 548 illustrated in FIG. 17C, with various diameters $D_1$, $D_2$ may enable the foot 548 to substantially absorb both the first and second frequencies, or ranges thereof. One will appreciate that other embodiments may include feet with any number and combination of different diameters to meet the specific range of frequencies being absorbed.

FIG. 17C shows another embodiment of a foot 548 that includes a first diameter $D_1$ that is smaller than a second diameter $D_2$. In this embodiment, the edge profile 556 of the foot 548 is straight so that the foot 548 substantially resembled an inverse cone. Other embodiments may include edge profiles 556 that result in various other shapes.

It will be appreciated that the feet 548 may be secured to the bottom surface 550 in a variety of ways. For example, in one embodiment, the feet 548 may be secured via hooks, nails, adhesives, or the like, without the need for a bolt 552 as shown in FIG. 28B. The feet 548, including other embodiments of feet described herein, may be made of an elastomeric material, such as rubber, silicone, or the like. The elastomeric material of the flexible matrix 554 may absorb vibrations from the outer housing 520 and provide added friction between the bottom surface 550 of the outer housing 520 and a support surface on which the outer housing 520 is placed.

Figure 29A:
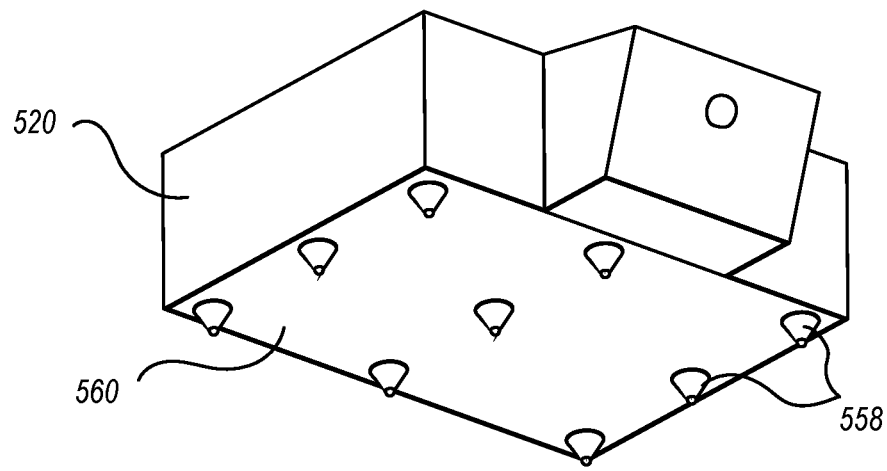
FIG. 29A illustrates one embodiment of a vibration absorption mechanism.

FIG. 29A illustrates a number of feet 558 disposed on the bottom surface 560 of an outer housing 520. In this embodiment, nine feet 558 serve as an interface between the bottom surface 560 and a support surface. Increasing the number of feet 558 may increase the vibration absorption capacity of the system. It may also increase the friction between the bottom surface 560 of the outer housing 520 and a support surface to minimize vibrational travel. Other embodiments may include more than nine feet 558 disposed on the bottom surface 560 in order to increase friction and vibration absorption capacity.

Figure 29B:
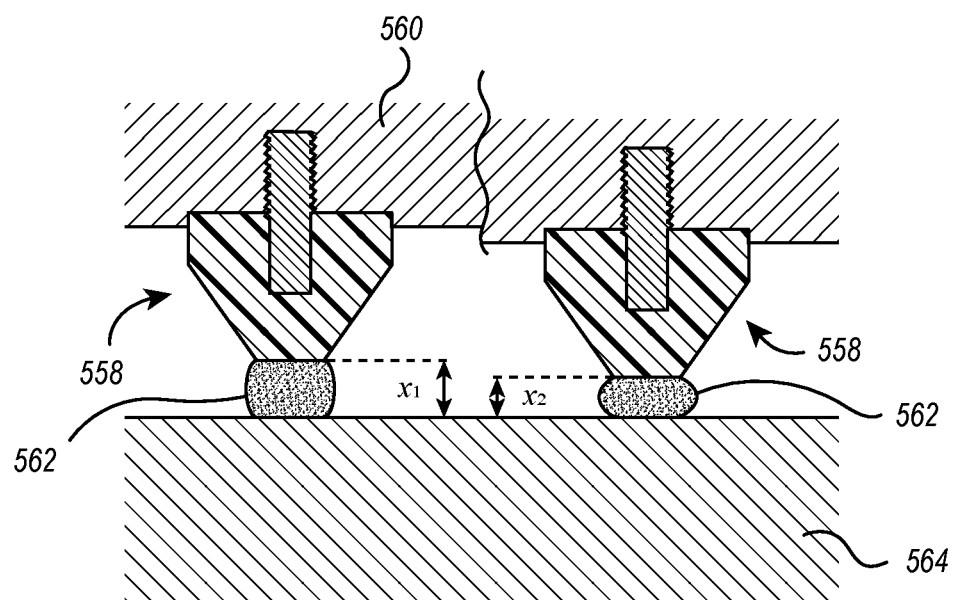
FIG. 29B illustrates a cross-sectional view of the vibration absorption mechanisms illustrated in FIG. 29A.

FIG. 29B illustrates a cross-sectional view of two of the feet 558 shown in FIG. 29A. There may be slight variations in the bottom surface 560 of the outer housing 520 and/or the support surface 564 that cause the surfaces 560, 564 to be uneven. This may result in inconsistent contact between some of the feet 558 and the support surface 564. Flexible spacers 562 may be disposed on the feet 558 to compensate for uneven surfaces 560, 564 so that all the feet 558 may be in contact with the support surface 564 despite unevenness.

As shown in FIG. 29B, the spacers 562 may compress from a first thickness $X_1$ to a second thickness $X_2$. The spacers 562 may be made of an elastomeric material, such as silicone or rubber, so that the thickness X of the spacer 562 may vary depending on the unevenness of the support surface 564 on which the outer housing 520 is placed. In this way, all of the feet 558 may be in contact with the support surface 564 in order to increase vibration absorption capability and friction between the bottom surface 560 and the support surface 564. The spacers 562 may also prevent the outer housing 520 from rocking due to a space or gap between the feet and the support surface.

Figure 28C:
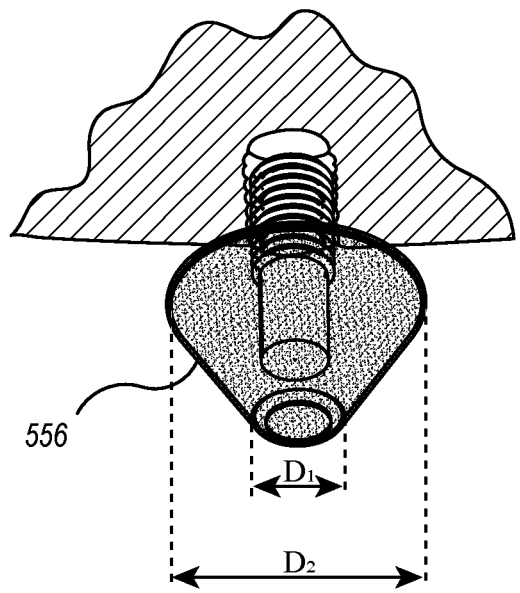
FIG. 28C illustrates one embodiment of a vibration absorption mechanism.
Figure 30A:
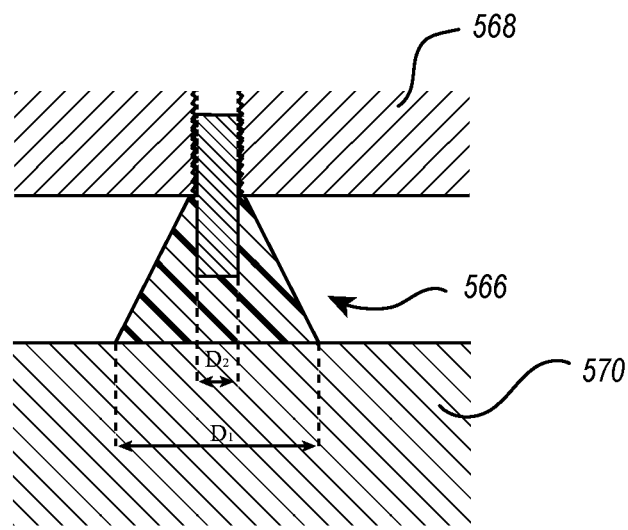
FIG. 30A illustrates a cross-sectional view of one embodiment of a vibration absorption mechanism.
Figure 30B:
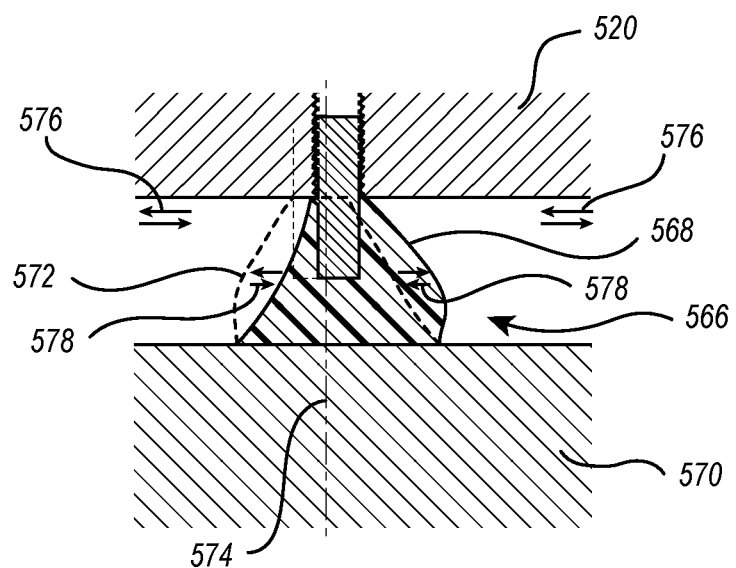
FIG. 30B illustrates the vibration absorption mechanism illustrated in FIG. 30A, but undergoing deformation due to vibrations.

FIG. 30A shows a cross-sectional view of one embodiment of a foot 566 for absorbing vibrations. This embodiment is similar to the embodiment illustrated in FIG. 28C, except here the first diameter $D_1$ is greater than the second diameter $D_2$. FIG. 30B illustrates how the foot 566, which may be comprised of an elastomeric material, may deform due to vibrations in the outer housing 520. As shown, vibrational movements of the outer housing 520, illustrated by arrows 576, are transferred to the foot 566. The foot 566 may laterally deform, as illustrated by arrows 578, from a first shape 572 to a second shape 568. This lateral deformation and/or change in shape of the foot 566 may occur while the interface 574 between the foot 566 and the support surface remains substantially constant. In this way, the foot 566 may absorb vibrations without substantially transferring them to the support surface 570 or traveling across the support surface 570.

The various embodiments of vibration absorption mechanisms described herein, including vibration absorption mechanisms disposed between inner and outer housings, flexible tubing, U-shaped tubing, and feet disposed on a bottom surface of the outer housing, may be employed singly or together in a multitude of combinations. These embodiments may also be included within various embodiments of a smoke evacuation system that includes various types of pumps, blowers, and/or compressors. The vibration absorption mechanisms described herein, combined with pumps that reduce vibrations and noise, may provide a substantial decrease in vibrations and noise inherent in typical smoke evacuation systems.

Motors and Methods of Control

The smoke evacuation system 400 illustrated in FIG. 13 includes motor 412 engaging the pump 410. The motor may rotate a rotary shaft of the various pumps 410 described herein. In one embodiment, the motor 412 may be a permanent magnet synchronous motor. Other embodiments may include a brushless DC motor. Brushless motors may have large starting torques from a fully stopped condition for use with the various pumps described herein. Brushless motors may also have less noise, greater dynamic response, and better speed-vs.-torque characteristics than brushed motors.

The pump 410 may create a pressure differential between a gas entering the pump 410 and a gas exiting the pump 410, as described above. This pressure differential, or compression ratio of the pump 410 may result in a high starting torque of the motor 412 in order to initiate the motor 412 rotating the pump 410.

Motor control methods may be employed to reduce the vibrations and increase motor efficiency and lifespan. Unwanted debris from the outside environment may inadvertently enter the airflow path 408 and cause clogging and/or blockages. These blockages within the system can cause pump and airflow path resistance pressures to rise as airflow is impeded. In order to maintain necessary airflow while blockages are present, pumps and/or motors may need more power and/or speed in order to compensate. Increased speed and/or power may diminish the efficiency of the motor and pump as well as decrease their lifespan. Various control methods of a smoke evacuation system, particularly methods of motor regulation, as described herein, may maintain airflow rates, increase motor efficiency, and preserve the lifespan of the motor and/or pump, especially when blockages and/or clogging of the system occurs.

Figure 31:
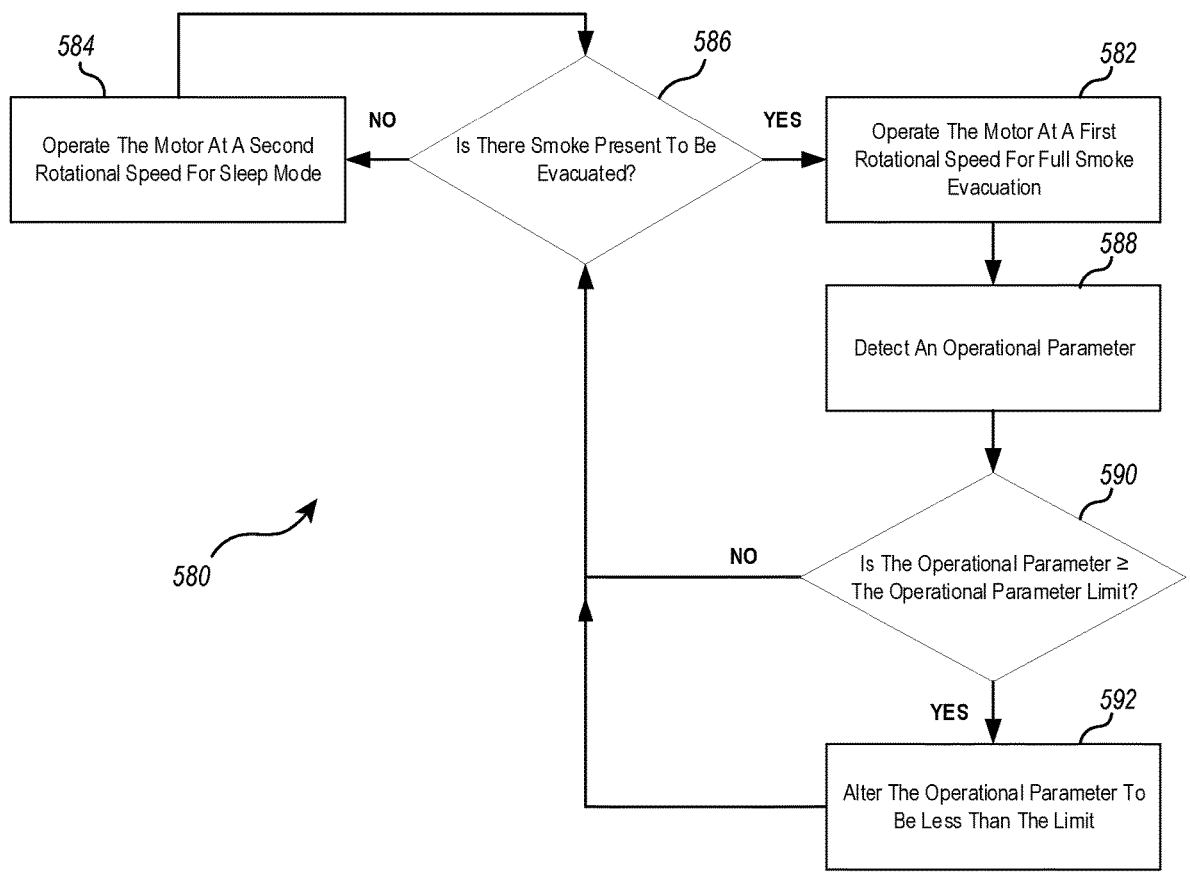
FIG. 31 illustrates a flowchart showing a method of reducing noise and vibration of a smoke evacuation system.

A method 580 for regulating the motor to reduce noise and vibration in a smoke evacuation system is shown in FIG. 31. In a first step 586, the system may sense or detect whether smoke is present to be evacuated or not. This detection may be done automatically when the practitioner begins cutting a patient during electrosurgery, or a separate smoke sensor may be employed to detect smoke present at cutting site. If smoke is present to be evacuated, then a next step 582 of the method may be to regulate the motor so that the rotational speed of the motor results in full smoke evacuation. If no smoke is present to be evacuated, then the next step may be to regulate the motor to operate at a rotational speed so that the motor is in sleep mode 584.

In one embodiment, a method of regulating the motor may include varying a supply of electrical current to the motor. For instance, the method 580 may include supplying a first amount of current to the motor to cause the motor to operate at a first performance level. Alternatively, a second amount of current may be supplied to the motor to cause the motor to operate at a second performance level. The supply of current may be accomplished by varying a pulse width modulation (PWM) duty cycle of an electrical input to the motor. In other embodiments, the current may be varied by adjusting the frequency of the current supplied to the motor. The motor may be engaged with a rotary mechanism, such as the compressors and blowers described above, so that reducing the duty cycle or frequency of a current input to the motor decreases the rotational speed of the rotary mechanism.

In one embodiment, a regulation of the motor may depend on an initial condition, such as the rotational speed of the rotary mechanism. For example, once the system is running, the regulation of the motor may operate the motor at a constant speed that equals the initial rotational speed of the motor. In one embodiment, the first performance level of the motor may result in a first rotational speed of a rotary shaft of the motor engaging a rotary mechanism. The first performance level therefore, may result in a faster rotation of the rotary mechanism. This first performance level, and corresponding rotation speed of the rotary mechanism, may be the speed needed for normal suction of a gas through the airflow path. A second performance level may be slower than the first so that the second performance level causes the rotary mechanism to operate at a speed lower than the first level.

The first performance level may be employed when there is no smoke produced by the electrosurgical instrument, but it is advantageous to keep the smoke evacuation system active. For example, a practitioner performing electro-surgery may temporarily have no need to suck smoke into the system to be filtered because the practitioner is not currently cutting the flesh of the patient and producing smoke. Instead of completely turning off the smoke evacuation system every time smoke is not being produced, and suction is temporarily not needed, the motor may switch to the second, slower performance level.

When the practitioner begins cutting again with the electrosurgical instrument, producing unwanted smoke, the motor may be switched back to the first, higher performance level, thus creating a higher vacuum pressure necessary to suck smoke into the system to be filtered. This lower second performance level may be thought of as a sleep mode. In sleep mode, the motor may still run, but not to its full or usual strength/rotational speed. The sleep mode may preserve the lifespan of the motor, and/or rotary mechanism with which it is engaged, by reducing the stress and wear caused by running the motor at full capacity at all times.

The second, lower performance level of the motor may be more advantageous than turning the motor completely off when suction is not needed, and switching the motor on when suction is needed. This is because a practitioner may need to use the suction only intermittently during long periods of surgery. Turning a motor on from a completely turned-off state requires high start-up torques in order to overcome the standstill inertia of the motor. Repeatedly turning the motor on from a completely off mode in this manner is inefficient and may decrease the lifespan of the motor. Alternatively, employing a sleep mode as described above, with a first and second performance level, allows the motor to remain on during intermittent non-use of the system during surgery, so that activation of the first performance level when suction is needed can be done without the higher torques needed to overcome standstill inertia.

In one embodiment, a method of motor control may be employed to limit substantial overheating of the motor. The motor may overheat if a blockage in the airflow path of the smoke evacuation system causes an overworking of the motor and/or rotary mechanism as they attempt to compensate for the blockage and maintain a constant airflow rate. Therefore, in the method 580 for regulating the motor, a further step may include detecting an operational parameter. The operational parameter may be, but is not limited to, the temperature of the motor and/or rotary mechanism and/or the pressure in the airflow path of the smoke evacuation system.

In one embodiment, the next step 590 may be to compare the detected operational parameter to an operational parameter limit. This parameter limit may be preset. If the detected operational parameter is greater than or equal to the operational parameter limit, the next step 592 of the method may include altering the operational parameter to be less than the operational parameter limit. In one embodiment, the method may include setting a temperature limit and sensing a temperature of the motor and/or rotary mechanism. When the temperature of the motor and/or the rotary mechanism is equal to or greater than the temperature limit, the motor may be shut off or its performance level reduced.

In one embodiment, the method may include defining a pressure limit and sensing a pressure within the circulation path of the rotary mechanism and/or the airflow path of the smoke evacuation system. A pressure inside the airflow path or rotary mechanism may increase when blockage occurs inside the airflow path as described above. In order to prevent the motor from overextending itself to overcome these higher pressures, the motor may be shut off or its performance level reduced, as described above, when the sensed pressure is equal to or greater than the set pressure limit. In one embodiment, the method may include disengaging the motor from the rotary mechanism. The motor may disengage from the rotary mechanism via a clutch.

In one embodiment, the method may include manipulating one or more orifices disposed near the motor within the airflow path of the smoke evacuation system. This method may also include defining a pressure limit and sensing a pressure within the airflow path as described above. When the sensed pressure is equal to or greater than the pressure limit, the one or more orifices may be opened to allow air to flow from inside the otherwise closed airflow path of the system to the surrounding environment, or vice versa. Opening the one or more orifices may reduce the pressure within the system, thus preventing the motor and/or rotary mechanism from attempting to compensate for the higher pressure.

The various methods of regulating the motor and or smoke evacuation system described herein may be employed in conjunction with any of the embodiments of a smoke evacuation system described above. These methods may also be employed independent of the various other embodiments.

Smoke Evacuation System Fluid Traps

In some embodiments, a smoke evacuation system includes a fluid trap that directs smoke from a vacuum hose and into a filter and removes and collects at least a portion of the fluid content from the smoke. In some embodiments, the fluid trap includes an inlet port with an inlet body extending into an interior chamber of the fluid trap and oriented to initially direct incoming smoke into a bottom, interior chamber of the fluid trap. The fluid trap additionally includes an exhaust port for directing smoke from the interior chamber of the fluid trap to an area outside the fluid trap (e.g., into a filter associated with the smoke evacuation system). In some embodiments, the exhaust port is sized and shaped to mechanically couple to a smoke filter and can additionally, or alternatively, be sized and shaped to prevent the fluid trap from spilling its contents when, for example, the fluid trap is placed on a surface contacting the exhaust-port-side of the fluid trap.

In some embodiments, the fluid trap is sized and shaped to prevent spillage of stored fluid when the fluid trap is detached from the smoke evacuation system and positioned on a surface in any of a variety of different orientations. In some embodiments, the fluid trap includes a protrusion in a sidewall that increase the volume of the fluid reservoir of the fluid trap and which may additionally, or alternatively, prevent collected fluid from spilling when the fluid trap is positioned on a surface. Fluid traps disclosed herein can, in some embodiments, include a plurality of baffles or condensation surfaces to promote retention and/or extraction of fluid from smoke.

One or more embodiments beneficially enable identification of the relative or absolute fluid volume within the fluid trap, and in some embodiments, fluid traps can include visual or auditory indicators of the fluid level within the fluid trap. In some embodiments, the fluid trap can include a drain valve for quickly and/or easily accessing the contents of fluid trap and which can further enable emptying or draining the contents of the fluid trap. Beneficially, the fluid traps disclosed herein reduce the amount of fluid entering the filter or other components of smoke evacuation devices and safely retain such fluids collected by preventing or reducing the likelihood an inadvertent spill can occur. By reducing the total fluid content of the smoke and removing bulk liquid from the smoke, the usable life of mechanically coupled filters can be increased. Additionally, or alternatively, the reduced fluid content within the smoke can protect the electrical components within or associated with the smoke evacuation device.

Figure 32:
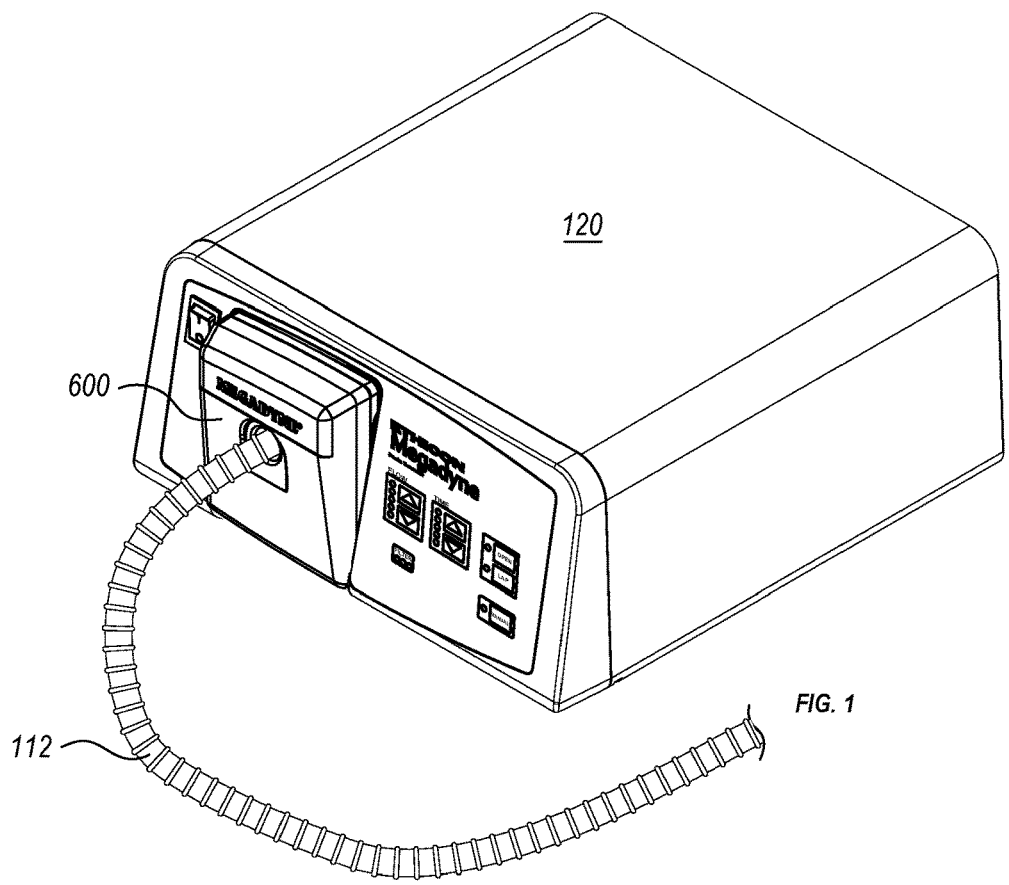
FIG. 32 illustrates a smoke evacuation system associated with an exemplary fluid trap.

Illustrated in FIG. 32 is the smoke evacuation system 120 of FIG. 1, and as shown, the smoke evacuation system 120 is coupled to a vacuum hose 112. The smoke evacuation system 120 is configured to produce suction and thereby draw smoke from the distal end of the vacuum hose 112 into the smoke evacuation system 120 for processing. Instead of the vacuum hose 112 being connected to the smoke evacuation system 120 through a smoke filter end cap (as shown in FIG. 1), the smoke evacuation system 120 of FIG. 32 is connected to the vacuum hose 112 through a fluid trap 600.

In some embodiments, the fluid trap 600 is a first smoke processing point that extracts and retains at least a portion of the fluid from the smoke before relaying the partially processed smoke to the smoke evacuation system 120 for further processing and filtration. The smoke evacuation system 120 beneficially enables smoke to be processed, filtered, or otherwise cleaned, reducing or eliminating unpleasant odors or other problems associated with smoke generation in the surgical theater (or other operating environment), and by extracting fluid from the smoke before it is processed by the smoke evacuation system 120, the fluid trap, among other things, increases the efficiency of the smoke evacuation system and increases the life of filters associated therewith.

Figure 33:
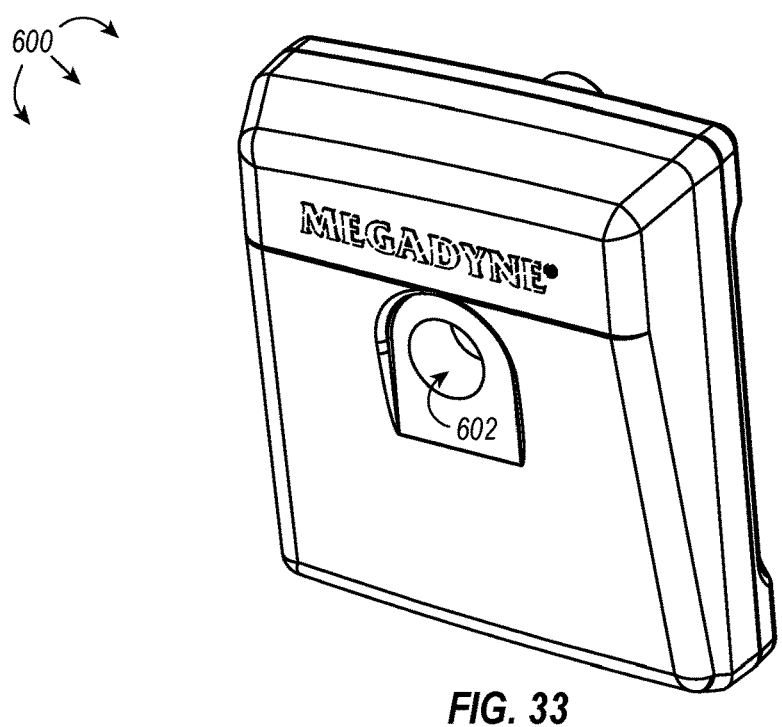
FIG. 33 illustrates a front perspective view of an exemplary fluid trap.
Figure 34:
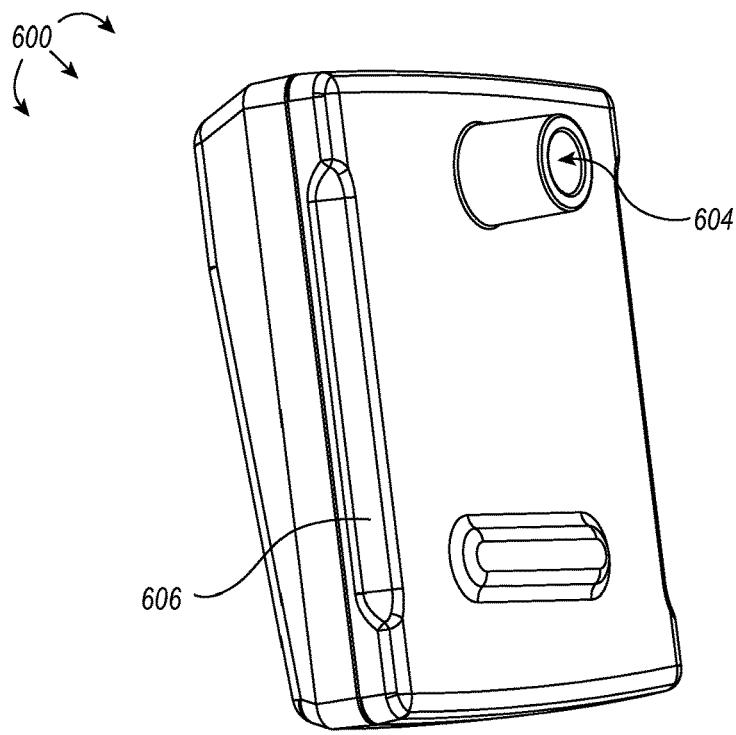
FIG. 34 illustrates a rear perspective view of the exemplary fluid trap of FIG. 33.
Figure 35:
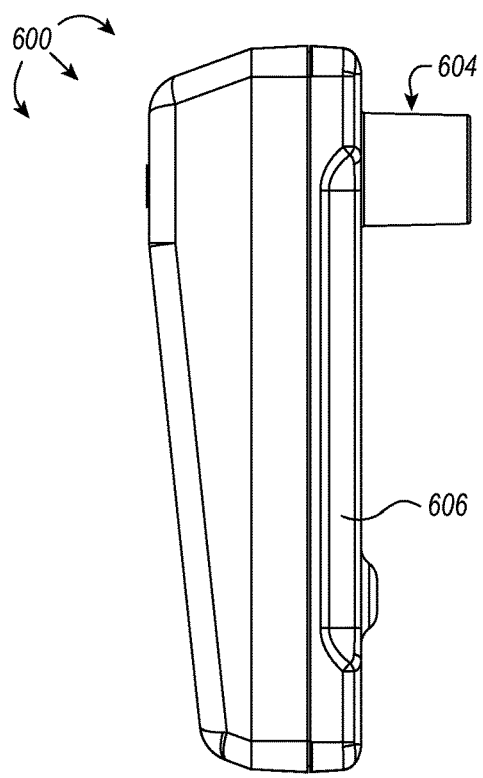
FIG. 35 illustrates a side view of the exemplary fluid trap of FIG. 33.

Referring now to FIGS. 33-35, illustrated are various views of a fluid trap 600 that is detached from or has yet to be associated with a smoke evacuation system, such as the smoke evacuation system 120 of FIG. 32. FIG. 33 illustrates a front perspective view of the fluid trap 600, and as shown, the fluid trap 600 includes an inlet port 602 that is defined by the front cover or surface of fluid trap 600. In some embodiments, the inlet port 602 is configured to releasably receive a vacuum hose. For example, an end of a vacuum hose can be inserted at least partially within the inlet port 602 and form an interference fit therewith. The interference fit can, in some embodiments, be a fluid tight and/or airtight fit so that substantially all of the smoke passing through the vacuum hose is transferred into the fluid trap 600. In some embodiments, other mechanisms of coupling or joining the hose with the inlet are employed such as, for example, a latch-based compression fitting, an O-ring, threadedly coupling the hose with the inlet, or other coupling mechanism known in the art.

A fluid tight and/or airtight fit between the vacuum hose and the fluid trap 600 can beneficially prevent fluids or other contents within the smoke from leaking at or near the junction of these two components. In some embodiments, the vacuum hose can be associated with the inlet port through an intermediate coupling device (e.g., an O-ring, adaptor, etc.) to further ensure an airtight and/or fluid tight connection between the vacuum hose and the fluid trap.

As shown in the rear perspective view of the fluid trap 600 illustrated in FIG. 34, the fluid trap 600 additionally includes an exhaust port 604 extending away from a rear cover or surface of the fluid trap 600. The exhaust port 604 defines an open channel between an interior chamber of the fluid trap 600 and the exterior environment. In some embodiments, the exhaust port 604 is sized and shaped to tightly associate with a smoke evacuation system or components thereof. For example, exhaust port 604 can be sized and shaped to associate with and communicate at least partially processed smoke from the fluid trap 600 to a smoke filter housed within smoke evacuation system 120. In some embodiments, the exhaust port extends away from a front, top, or side surface of the fluid trap.

In some embodiments, the exhaust port 604 includes or is spaced apart from the smoke evacuation system by a membrane (not shown). The membrane can act to prevent water or other liquid collected in the fluid trap from passing through the exhaust port and into the smoke evacuation system while permitting air, water vapor and/or evaporate to freely pass. For example, a high flow rate microporous polytetrafluoroethylene (PTFE) can be positioned downstream of the exhaust port and upstream of the smoke evacuation system components (e.g., a vacuum pump inlet) to protect the smoke evacuation system from damage and/or contamination.

Referring back to FIG. 34, fluid trap 600 can additionally include a gripping region 606 to assist a user in handling the fluid trap and/or connecting it with a vacuum hose and/or smoke evacuation system. The gripping region 606 is depicted as being an elongate recess. However, it should be appreciated that the gripping region 606, in some embodiments, can include a plurality of recesses or grooves, any of which can be sized and shaped to accommodate a user's digits or to otherwise provide a gripping surface. In some embodiments, the gripping regions are protrusions, rings, or tassels instead of recesses.

Referring now to FIG. 35, illustrated is a side view of the fluid trap 600 depicted in FIGS. 33 and 34. As shown, the front cover or surface of the fluid trap 600 is tapered from a wider upper region to a narrower lower region when viewing the fluid trap 600 in an upright position. In some embodiments, the front cover or surface does not taper, but rather, it maintains substantially uniform dimensions between the upper and lower regions of the fluid trap 600.

As also shown in FIG. 35, the exhaust port 604 is positioned proximate the upper end of the rear cover or surface of fluid trap 600 when the fluid trap 600 is viewed in an upright position. The inlet port 602 can be positioned substantially within the center of the fluid trap 600, as shown in the vertical cross-section of the fluid trap 600 depicted in FIG. 36, or it can be positioned higher or lower along the front surface. In some embodiments, the inlet port is positioned laterally off-center and/or proximate an outer edge of the front cover or surface. The respective positioning of the exhaust port 604 can mimic the lateral and/or vertical positioning of the inlet port, but in some embodiments, the exhaust port 604 remains in the position shown in FIGS. 32-36 so that its placement does not functionally impair the fluid trap 600 from associating with the smoke evacuation system 120 (or components thereof).

Figure 36:
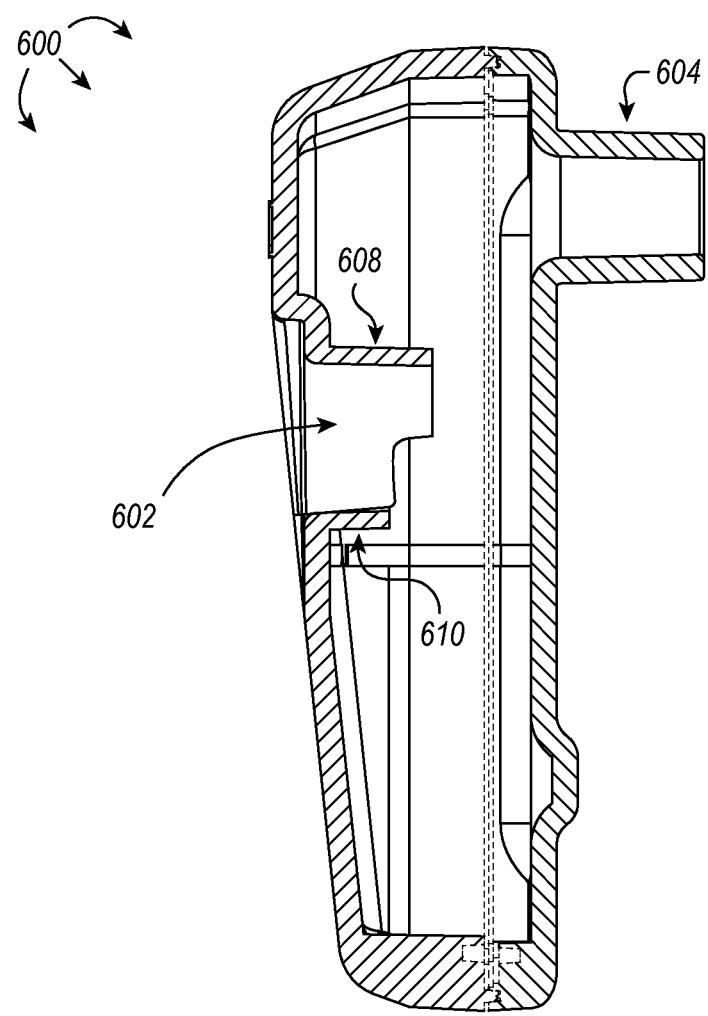
FIG. 36 illustrates a vertical cross-section of the exemplary fluid trap depicted in FIG. 35.

With continued reference to FIG. 36, the inlet port 602 is defined by a notched cylindrical body that extends into the interior chamber of the fluid trap 600. The notched cylindrical shape of the inlet port 602 is defined by an upper sidewall 608 and a lower sidewall 610. The upper sidewall 608 extends into the interior chamber of the fluid trap 600 farther than the shorter, lower sidewall 610 such that a cross-sectional slice transecting the longitudinal axis of the inlet port 602 yields a circle (or similar arcuate shape) where the cross-section includes both the upper and lower sidewalls 608, 610, and a cross-sectional slice transecting the longitudinal axis of the inlet port 602 yields a semi-circle where the cross-section includes only that portion of the upper sidewall 608 that extends beyond the lower sidewall 610.

As also shown in FIG. 36, the exhaust port 604 is positioned above the inlet port 602. In some embodiments, the exhaust port 604 is positioned lower on the rear cover of the fluid trap 600 than what is illustrated in FIGS. 34-36. In such embodiments, the exhaust port 604 is preferentially positioned above an associated inlet a port 602. As used herein, the relative positioning of the exhaust port being "above" the inlet port or the inlet port being positioned "below" the exhaust port is intended to preferentially include embodiments where any portion of the openings defined by the inlet port and exhaust port, respectively, are in different horizontal planes. Additionally, in some embodiments, the exhaust port is understood to be "above" the inlet port when the exhaust port is more proximate an upper edge or surface of the fluid trap than the inlet port and/or the inlet port is more proximate a lower edge or surface of the fluid trap than the exhaust port. Additionally, the exhaust port can be "above" the inlet port if a portion of the respective openings (e.g., less than 50%, less than 40%, less than 30%, less than 20%, less than 10%, less than 5%, etc.) coexist within the same horizontal plane (or sets of horizontal planes) but there is at least one horizontal plane that includes an upper surface of the exhaust port that does not include any portion of the inlet port.

In some embodiments, the relative positioning of the inlet port 602 and the exhaust port 604 promote extraction and retention of fluid from the smoke as it passes into the fluid trap 600. In some embodiments, the notched cylindrical shape of the inlet port 602 can beneficially act to initially direct smoke and the accompanying airflow towards a fluid reservoir of the fluid trap 600 or otherwise directionally away from the exhaust port. Such an exemplary airflow is depicted in FIG. 37.

As shown, smoke enters the fluid trap 600 through inlet port 602 (illustrated by arrow A) and exits the fluid trap through exhaust port 604 (illustrated by arrow E). At least partially due to the geometry of the inlet port (e.g., a longer, upper sidewall 608 and a shorter, lower sidewall 610), the smoke entering the inlet port 602 is initially directed downward into the fluid reservoir of the fluid trap 600 (illustrated by arrows B). As smoke continues to be pulled into the fluid trap 600 along arrows A and B, the smoke that was initially directed downward tumbles and is directed laterally away from its source to travel in an opposite but parallel path towards the upper portion of the fluid trap 600 and out of the exhaust port 604 (illustrated by arrows D and E).

Figure 37:
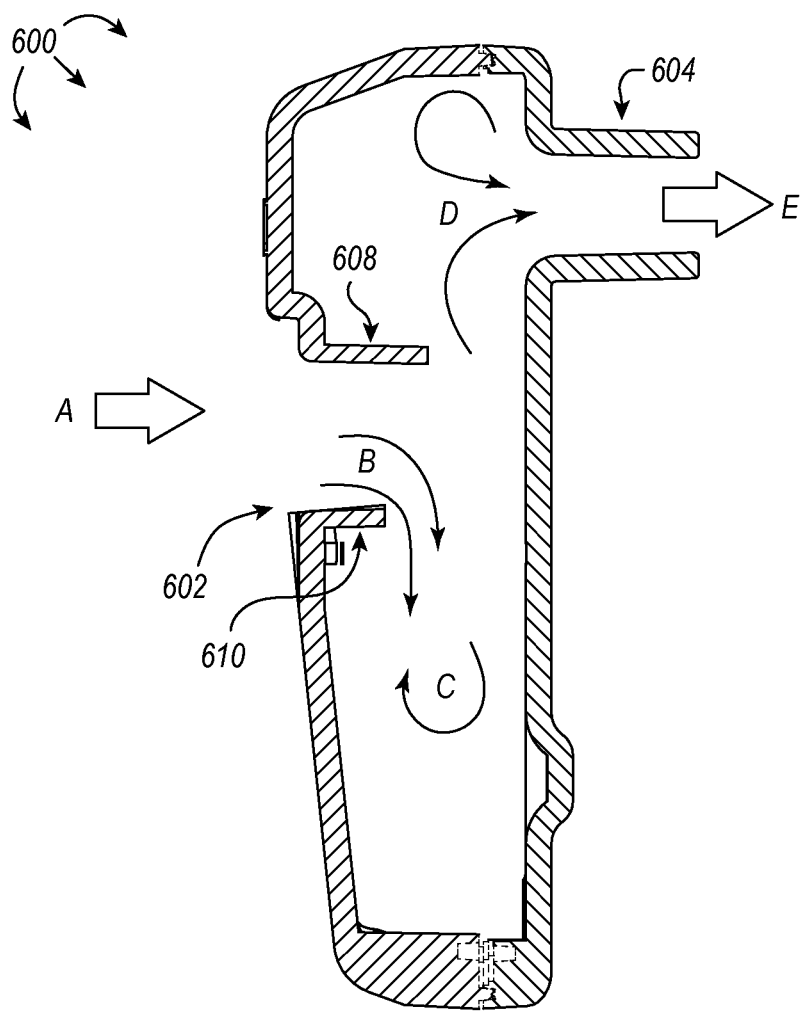
FIG. 37 illustrates a simplified vertical cross-section of the exemplary fluid trap depicted in FIG. 35 and an embodiment of air flow through therethrough.
Figure 41:
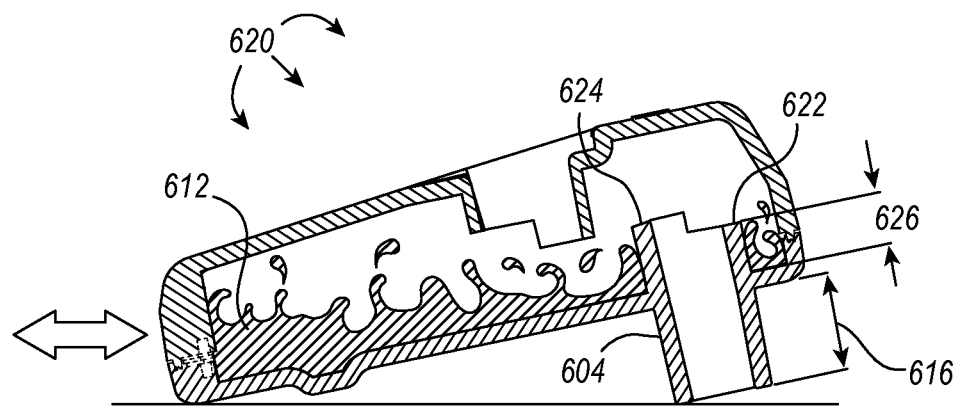
FIG. 41 illustrates a simplified vertical cross-section of another exemplary fluid trap having fluid collected therein that is positioned on a surface inlet-side up with the fluid shown as being agitated.

In some embodiments, the directional flow of air/smoke through the fluid trap 600 (as illustrated in FIG. 37, for example) enables fluids within the smoke to be extracted and retained within the lower portion of the fluid trap 600. Further, the relative positioning of the exhaust port 604 with respect to the inlet port 602 discourages liquid from inadvertently being carried through the exhaust port 604 by the flow of smoke while not substantially hindering airflow into and out of the fluid trap 600. Additionally, the configuration of the inlet and exhaust ports 602, 604 and/or the size and shape of the fluid trap, itself, can enable the fluid trap 600 to be spill resistant.

For example, in an upright position, fluid 612 that is extracted from smoke is retained within the bottom portion of the fluid trap 600, as shown, for example, in FIG. 38. If the fluid trap 600 falls or is moved or its orientation changed from an upright position such that it becomes oriented on a surface inlet port side down, as shown in FIG. 39, the fluid trap 600 can still retain the fluid 612 within the interior chamber owing to its size and shape. For example, the upper sidewall 608 and the lower sidewall 610 of the inlet port 602 protrude deep enough into the interior chamber of the fluid trap 602 to create a front cover volume that is bounded by the surface area of the interior surface of the front cover and the sidewalls 608, 610 of the inlet port 602.

It should be appreciated that although the fluid 612 in FIG. 39 appears to be separated into two distinct portions, FIG. 39 illustrates a cross-sectional view of the fluid trap 600. As described above, the inlet port 602 can be defined by a notched cylindrical sidewall (or cylindrical sidewall) that does not transact the entire front cover or surface. Accordingly, when the fluid trap 600 is positioned on a surface with the inlet side down, as shown in FIG. 39, fluid 612 can pass around the intrusive sidewalls of inlet 602 and be distributed along the interior surface of the cover. Accordingly, in some embodiments, the front cover of the fluid trap is dimensioned such that the volume of the front cover is equal to or greater than the maximum fluid volume of the fluid reservoir. The volume of the front cover can, for example, be calculated as the product of the surface area of the front cover and the average depth of the front cover with respect to the lowest intrusive sidewall of the inlet port. In some embodiments, the maximum volume of the fluid reservoir is determined by the volume of the front cover. As used herein, a "fluid reservoir" includes a subset of the interior chamber of the fluid trap, particularly the interior volume of the fluid trap defined by the interior sidewalls of the fluid trap below the inlet port.

In some embodiments, the fluid trap 600 can be considered full when the volume of fluid 612 contained therein rises as high as the terminal end of the lower sidewall 610 when the fluid trap is positioned on a surface with the inlet side down (i.e., at a maximum front cover volume). In some embodiments, the fluid trap 600 can be considered full when the volume of fluid 612 contained therein rises a particular distance below the terminal end of the lower sidewall 610 when positioned on the surface with the inlet side down. In some embodiments, the foregoing particular distance is about 1/16", 1/8", about 1/4", about 3/8", about 1/2", about 5/8", about 3/4", about 7/8", or about 1".

In some embodiments, the fluid trap 600 is additionally spill resistant owing at least partially to its size and shape when oriented on a surface with the exhaust port side down, as shown in FIG. 40. The sidewalls defining the exhaust port 604 extend a length 616 away from the rear surface of the fluid trap 600 such that the exhaust port acts like a kickstand to stably support the fluid trap 600 in an inclined position, directing the fluid 612 away from the exhaust port 604. As shown in FIG. 40, the fluid 612 is retained within the fluid reservoir of the fluid trap 600 and at least partially along the rear cover of the fluid trap. The fluid 612 is retained within the fluid trap 600 when the fluid trap is oriented exhaust port 604 side down because, in some embodiments, the rear cover volume is greater than the volume of fluid 612 contained therein. The rear cover volume can, in some embodiments, be calculated as the volume of the interior chamber defined by the interior sidewalls of the fluid trap that is bounded by a line tangent to a lowest interior-facing sidewall of the exhaust port and parallel with the surface upon which the exhaust port lies. In some embodiments, the line parallel with the surface upon which the exhaust port lies is a line normal to the force of gravity.

In some embodiments, the volume of the rear cover is expanded by a protrusion or protruding sidewall 618. The protruding sidewall 618 can be sized proportionally with the length 616 of the exhaust port 604, or it can have defined dimensions regardless of the length 616 of the exhaust port 604. For example, in embodiments where the protruding sidewall 618 is sized proportionally with the length 616 of the exhaust port 604, as the length 616 of the exhaust port 604 decreases, the angle of incline experienced by the fluid trap 600 can similarly decrease. A decreased incline causes a decreased rear cover volume. By increasing the width or depth of the protrusion 618, the protrusion 618 effectively increases the rear cover volume. Alternatively, as the length 616 of the exhaust port 604 increases, the angle of incline experienced by the fluid trap 600 can similarly increase. The increased incline causes an increase in the rear cover volume. The protrusion 618 can be proportionally shrunk or removed as the rear cover volume increases to prevent fluid 612 from spilling out of the exhaust port 604.

It should be appreciated that in some embodiments, the fluid reservoir volume can additionally be increased by the same protrusion 618 shown in at least FIGS. 38-40 (or a different protrusion). For example, an increase in the size of the protrusion 618 can proportionally increase the fluid reservoir volume, and a decrease in the size of the protrusion 618 can proportionally decrease the fluid reservoir volume. Additionally, although the protrusion 618 is shown in at least FIGS. 38-40 as being located on the rear cover, a protrusion may additionally, or alternatively, be located on the front cover.

In some embodiments, the fluid trap 600 can be considered full when the volume of fluid 612 contained therein rises as high as but not into the exhaust port 604 when the fluid trap is positioned on a surface with the exhaust port 604 side down (i.e., at a maximum rear cover volume).

As described above with respect to at least FIGS. 38-40, embodiments of the present disclosure include fluid traps that are spill resistant. In such embodiments, the maximum volume of fluid that can be extracted and retained while maintaining the fluid trap's spill resistant feature is dependent upon the volume of the fluid reservoir of the fluid trap, the volume of the front cover, and the volume of the rear cover. In some embodiments, the maximum volume is the lesser of the fluid reservoir volume, the front cover volume, and the rear cover volume. For example, in some embodiments, the front cover volume is less than the fluid reservoir volume and the rear cover volume. Accordingly, the maximum volume for the foregoing exemplary fluid trap is at most the front cover volume.

Figure 44:
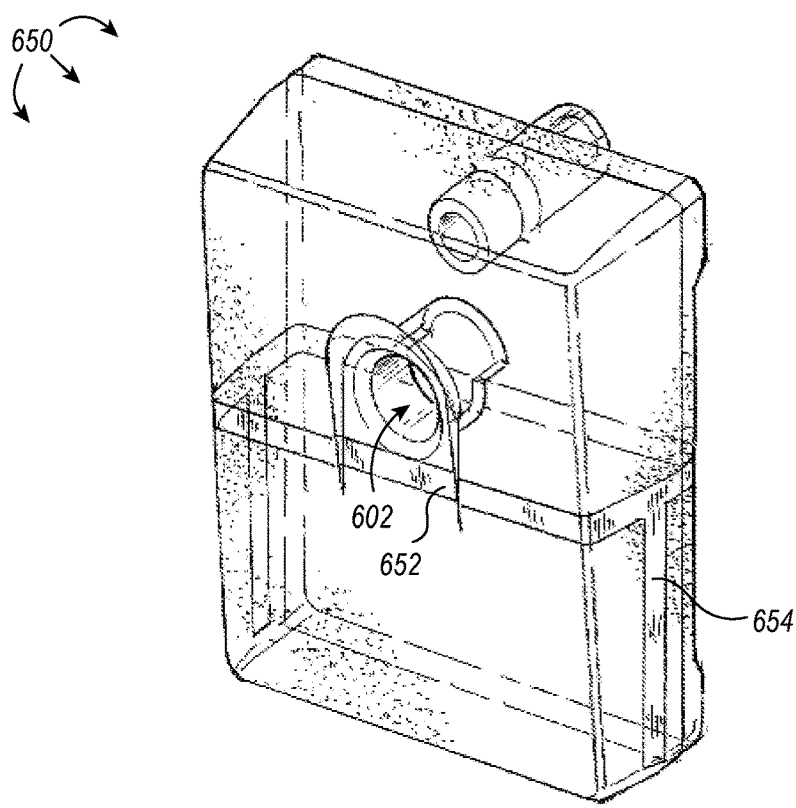
FIG. 44 illustrates a perspective view of a fluid trap with transparent viewing windows.

Referring now to FIG. 44, the exhaust port 604 can be adapted to include upper and lower sidewalls 622, 624 that extend into the interior chamber of the fluid trap 620. The upper and lower sidewalls 622, 624 can similarly form a notched cylinder (as described above with respect to upper and lower sidewalls 608, 610 of the inlet port 602). Alternatively, the upper and lower sidewalls of the exhaust port can define a cylindrical channel. Regardless, by extending upper and lower sidewalls 622, 624 of the exhaust port 604 into the interior chamber of the fluid trap 620, the fluid trap 620 becomes more resistant to spilling or at least reduces the likelihood that splashes or sloshing of the fluid 612 inside the fluid trap 620 results in spillage when the fluid trap 620 is positioned on a surface inlet side up—even when agitated. In some embodiments, extending upper and lower sidewalls 622, 624 into the interior chamber of the fluid trap 620 may also allow for a shorter exterior length 616 of the exhaust port 604 without appreciably risking spilling liquid 612. In some embodiments, the length 626 of the upper sidewall 622, which is shorter than the lower sidewall 624 in some embodiments, can be proportional to the length 616 of the exhaust port 604. For example, the length 626 of the upper sidewall 622 can increase to compensate for a decreased length 616 of the exhaust port 604. Similarly, as the length 616 of the exhaust port 604 increases, the length 626 of the upper sidewall 622 can decrease.

In some embodiments, the exhaust port 604 protrudes into the interior chamber of the fluid trap 620, as illustrated in FIG. 44. This can, in some embodiments, decrease the likelihood that fluid can freely or accidentally transit between the inlet 602 and the exhaust 604. In some embodiments, having the exhaust port protrude into the interior chamber of the fluid trap increases the rear cover volume. Additionally, or alternatively, the exhaust port 604 protrudes into the interior chamber of the fluid trap 620 with the lower sidewall 624 being longer than the upper sidewall 622 so as to further manipulate the airflow through the fluid trap 620. As it should be appreciated, the configuration of sidewalls having a staggered length, as shown in FIG. 44, can increase the flow rate of air or smoke proximate the upper sidewall 622 (similar to the flow described above for inlet port 602).

Figure 42:
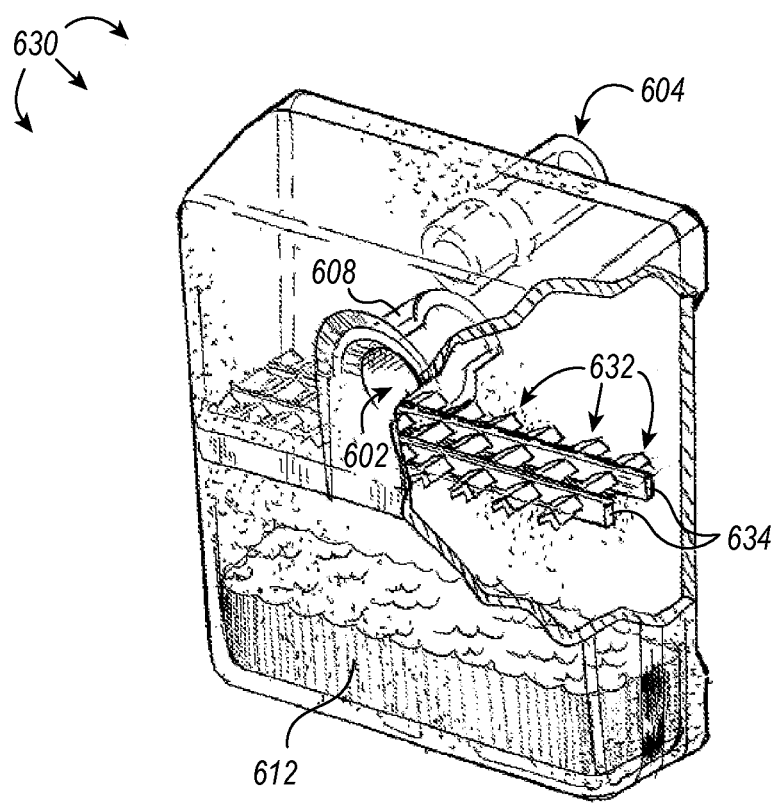
FIG. 42 illustrates a partial cross section, perspective view of a fluid trap having baffles.

In some embodiments, it may be advantageous to include physical barriers within the fluid trap to reduce the likelihood that splashes or sloshing of the fluid inside the fluid trap results in spillage. Referring now to FIG. 42, illustrated is a partial cross-section, perspective view of a fluid trap 630 having a plurality of baffles 632 disposed within an interior chamber thereof. The plurality of baffles 632 can be disposed along baffle securing members 634, as shown in FIG. 42. The baffle securing member 634 can attach to one or more interior surfaces of the fluid trap 630 and act to hold the plurality of baffles 632 stationary. In some embodiments, the baffles, themselves, are attached to one or more interior surfaces of the fluid trap, and the baffles securing members can be optionally omitted.

As illustrated by FIG. 42, smoke can enter inlet port 602 and be similarly directed downward owing to the shorter, lower sidewall 610 and the longer, upper sidewall 608 that form a notched cylindrical projection (as discussed above with respect to at least FIG. 37). Accordingly, liquid within the smoke can be directed to the fluid reservoir of the fluid trap 630 along angled baffles 632. Once the liquid 612 passes beneath the baffles 632, the angled arrangement of the baffles 634 acts to catch upward moving splashes or droplets and redirect them down towards the fluid reservoir. In such a manner, the plurality of baffles can minimize fluid motion during handling of the fluid trap 630. In some embodiments, the angled baffles 634 can additionally act as condensation surfaces to promote the condensation of liquid vapor in the smoke, which is similarly directed towards the interior chamber of the fluid trap 630 after condensing into droplets (not shown). In some embodiments, the baffles are made of absorptive material and can act to wick fluid from the smoke.

Figure 43:
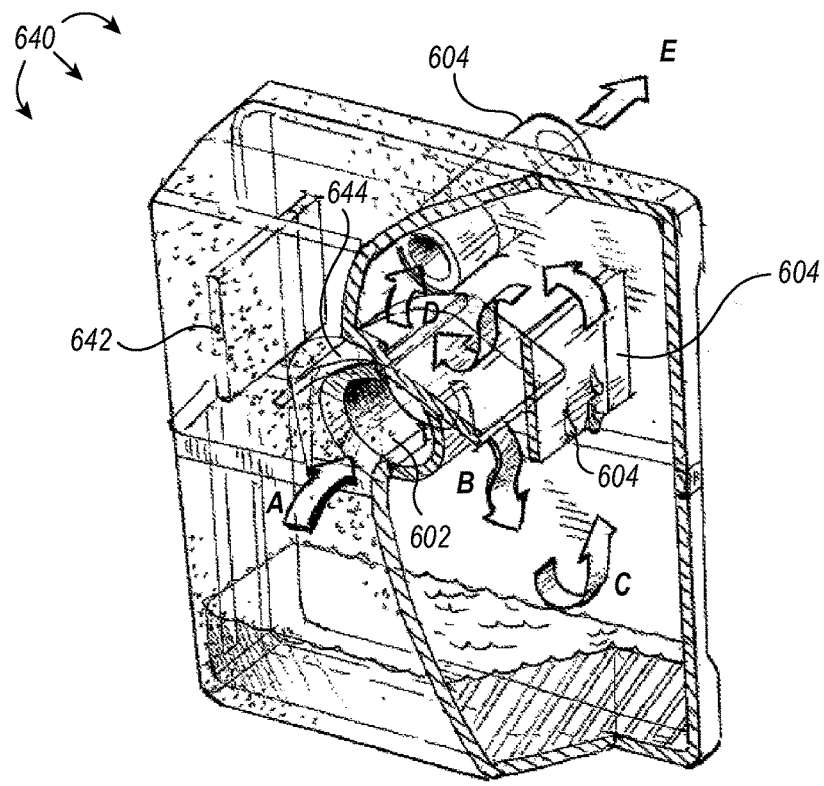
FIG. 43 illustrates a partial cross section, perspective view of a fluid trap having a plurality of interior condensation surfaces.

In some embodiments, additional measures can be taken to reduce and/or control aerosols and small droplet fluids that are moving at higher velocities by, for example, removing them from the airflow path. Referring now to FIG. 43, illustrated is a fluid trap 640 that includes a splash canopy 644 positioned within the collection chamber of the fluid trap 640, above the inlet port 602 and providing a physical barrier between the exhaust port 604 and the inlet port 602. As shown in FIG. 43, the splash canopy 644 spans the interior sidewall of the front cover to the interior sidewall of the rear cover and extends laterally across and past the width of the inlet port 602. In some embodiments, the splash canopy is attached to the sidewall of the rear cover, extends over the upper sidewall of the inlet port and towards the interior sidewall of the front cover but does not attach thereto.

The splash canopy 644 is also illustrated as having a downwardly concave arcuate shape. Additionally, or alternatively, the splash canopy can be planar and/or extend over the width of the inlet port. In some embodiments, the contour and position of the splash canopy 644 can advantageously act to direct incoming airflow (shown by arrow A) and any splashing fluid downward toward the bottom, interior chamber of the fluid trap 640 (shown by arrow B). Similar to the airflow described above with respect to FIG. 37, the downwardly directed air can flow laterally and upward (shown by arrow C) where it passes over and around a vertically oriented splash wall 642. As shown in FIG. 43, the splash wall 642 can span the distance between the interior sidewall of the front cover to the interior sidewall of the rear cover and can extend vertically a distance from at least the lower terminal edge of the splash canopy 644 (or lower) to the bottom of the exhaust port 604.

In some embodiments, the vertical distance spanned by the splash wall 642 can be different. For example, the splash wall can begin at a point coplanar to the bottom of the inlet port and extend vertically upward, terminating in at a point coplanar with the top of the splash canopy, the bottom of the exhaust port, or the top of the exhaust port. Additionally, as shown in FIG. 43, the splash wall 642 can be spaced apart from the splash canopy 644. However, in some embodiments, the splash canopy and the splash wall are connected to form a W-shaped or U-shaped splash wall that partially surrounds the exhaust port 604.

In some embodiments, the splash canopy 644 and/or the splash wall 642 can include or be made of a fibrous fluid wicking material (e.g., glass borosilicate or similar) which can enable the splash canopy 644 and/or splash wall 642 to remove aerosols and small droplet fluids from the inbound smoke. In some embodiments, the splash walls 642 and/or the splash canopy 644 can act as condensation promoting surfaces where aerosols and small droplets of fluids can condense and accumulate into droplets 646 that fall into the bottom, interior chamber.

In some embodiments, the fluid trap contains a plurality of splash walls and/or splash canopies, which can be tiered, stacked, or aligned in series. In some embodiments the splash walls and splash canopies are made of or include heat conductive materials that promote condensation.

In some embodiments, it may be advantageous to monitor the total volume of fluid collected within the fluid trap. As shown in FIG. 44, a fluid trap 650 can include a horizontal viewing window 652 and/or a vertical viewing window 654. The viewing windows 652, 654 can be an integral part of the fluid trap sidewalls. As shown in FIG. 4, the horizontal viewing window 652 can wrap circumferentially around fluid trap 650 at a position below the inlet port 602. The positioning of the horizontal window may, in some embodiments, indicate a maximum fill line for the fluid reservoir 650. Alternatively, a plurality of horizontal viewing windows can be positioned along the fluid trap (e.g., in tiers) so the volume of fluid within the fluid trap can be progressively monitored and/or observed. Additionally, or alternatively, the vertical viewing window 654 can join with one or more horizontal viewing windows at at least one point and extend to the bottom of the fluid trap 650, as illustrated in FIG. 4.

Although illustrated as being positioned on a side of the fluid trap 650, it should be appreciated that the vertical viewing window 654 may be positioned on a front surface and/or rear surface of the fluid trap 650. In some embodiments, placing the horizontal and/or vertical viewing windows on the front surface can beneficially enable a user to quickly identify the volume level of fluid contained within the fluid trap without disassociating or otherwise removing the fluid trap from the smoke evacuation system. In some embodiments, the viewing windows are made of a transparent and/or translucent material that allow a user to readily view the contents of the fluid trap through the viewing window. For example, the viewing window may include glass or plastic, or in some embodiments, the viewing window may include frosted glass or plastic to better indicate dark blood within the fluid trap.

Figure 45:
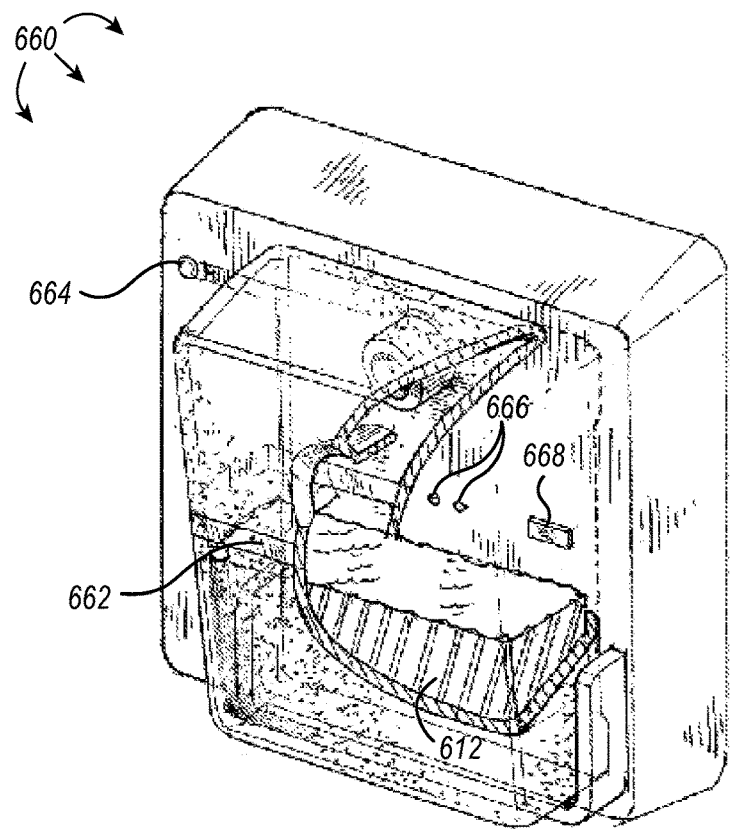
FIG. 45 illustrates a partial cross section, perspective view of a fluid trap having a fill detector and indicator light.

In some embodiments, a visual indicator coupled to a sensor can additionally, or alternatively, indicate the amount or volume of fluid within the fluid trap. For example, as shown in FIG. 45, the fluid trap 660 includes a horizontal viewing window 662 that indicates a maximum fill line for the fluid trap 660. The fluid trap 660 additionally includes an optical emitter and detector pair 666 positioned at or adjacently below the maximum fill line. The emitter and detector pair 666 can beneficially identify via optics whether fluid 612 within the fluid trap 660 has risen to a level at or above the emitter and detector pair 666. Upon determining that fluid 612 is at or above the level of the emitter and detector pair 666, an electrical signal can be sent to activate a status light 664 that indicates the fluid trap 660 is full.

Additionally, or alternatively, the fluid trap 660 can include an ultrasonic detector 668 that identifies a change in signal and causes an electrical signal to be sent to activate the status light 664, indicating the fluid trap 660 is full. For example, an identified change in signal can include the ultrasonic signal being consistently received at the ultrasonic detector 668 more quickly than previously observed. As an additional example, an identified change in signal can include the ultrasonic signal being received at the ultrasonic detector 668 within a threshold time that is indicative of the ultrasonic waves passing through a liquid medium.

Figure 46:
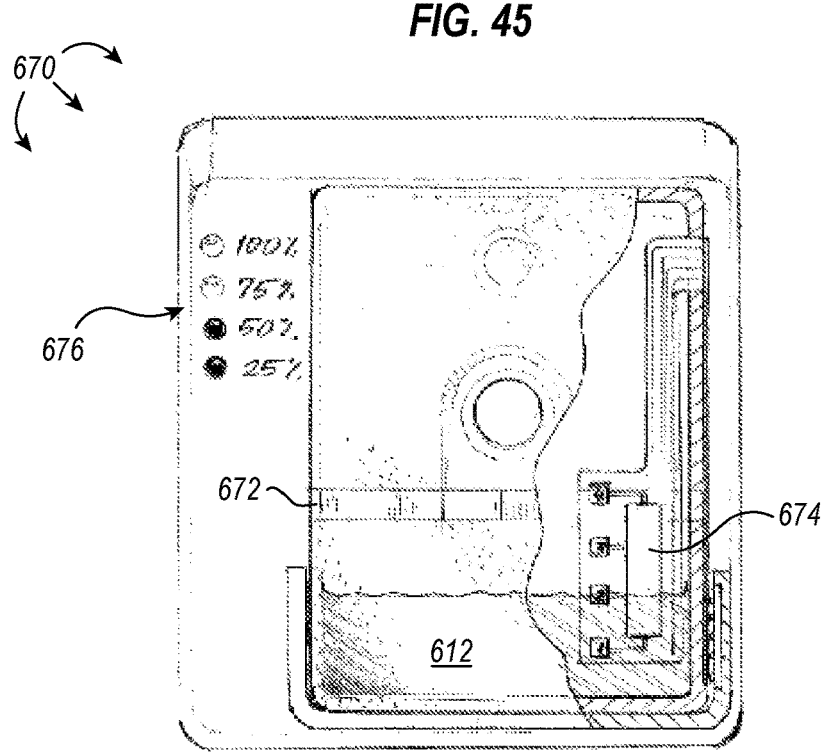
FIG. 46 illustrates a partial cross section, front view of a fluid trap having a graded fill sensor and indicator light.

In some embodiments, the volume of fluid within a fluid trap can be progressively monitored and/or indicated electronically, as shown, for example, in FIG. 46. The fluid trap 670 of FIG. 46 includes a resistive strip 674 having a plurality of nodes that are sequentially activated upon detection of liquid at the node. Each node of the resistive strip 674 can correspond to one or more status lights 676 such that upon activation of each node on the resistive strip, the corresponding status light is activated. For example, as shown in FIG. 46, the fluid level 612 is activating nodes 1 and 2, and the corresponding status lights—25% and 50% respectively—are turned on. In some embodiments, one of the nodes on the resistive strip can correspond to an audio signal or alarm that provides an audible cue—in addition to or separate from the visual cue(s) provided by the status light(s)—that the fluid trap is full and needs to be replaced or drained.

Although the embodiment of FIG. 45 is illustrated as having a single optical emitter and detector pair and a single ultrasonic detector, it should be appreciated that in some embodiments, a fluid trap can include a plurality of optical emitter and detector pairs and/or a plurality of ultrasonic detectors—and in any combination—to achieve an analogous progressive status light activation corresponding to the amount of fluid within the fluid trap like that depicted and described in FIG. 46.

Figure 47:
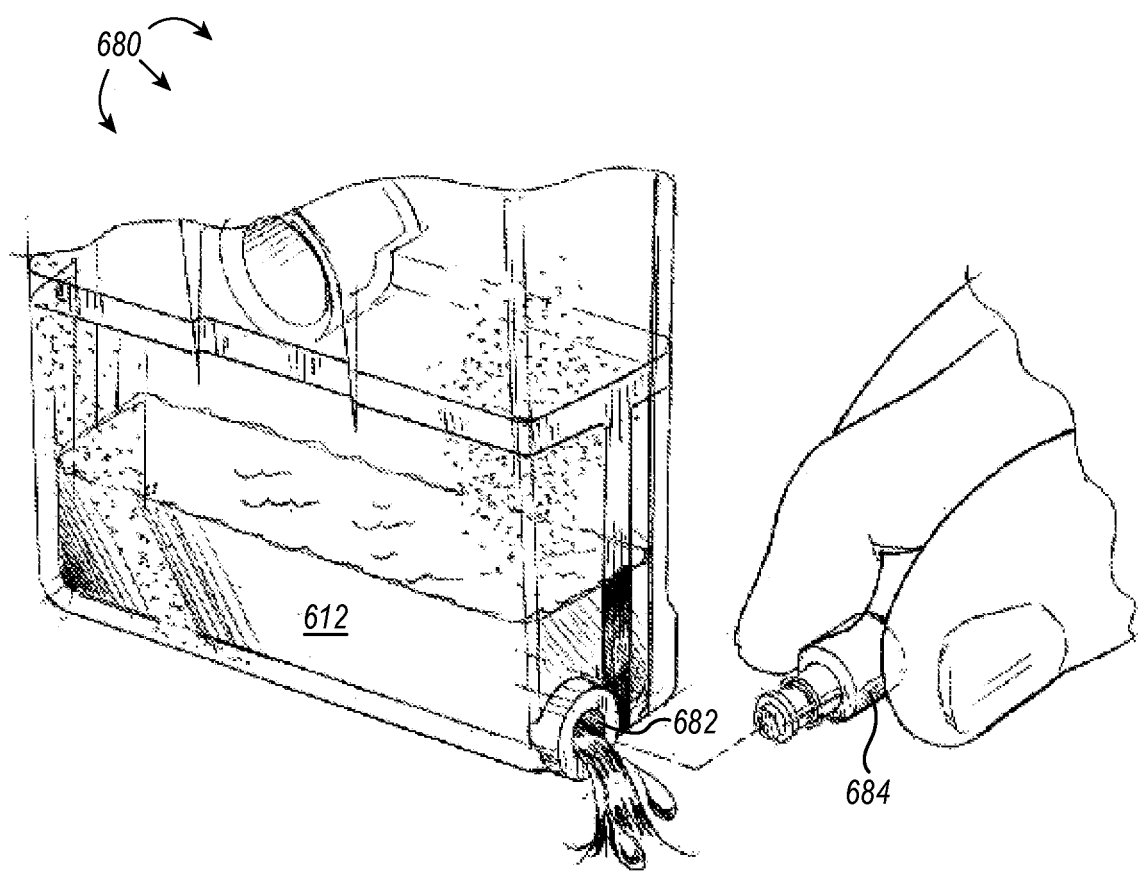
FIG. 47 illustrates a partial perspective view of a fluid trap with a drain valve.

In some embodiments, upon an indication that the fluid trap is full, the fluid trap is discarded. Alternatively, the fluid can be drained from the fluid trap for continued use. For example, as shown in FIG. 47, a fluid trap 680 can include a drain 682 for draining fluid 612 from the fluid trap 680. The drain 682 can be associated with a removable drain plug 684, as shown in FIG. 47, or alternatively, the drain can include a lever or valve for opening and/or closing the drain. The drain 682 may be positioned at a lower side edge of the fluid trap 660, or in some embodiments, the drain may be positioned on the lower front face of the fluid trap. In some embodiments, it is advantageous for the drain to be located near the bottom of the fluid trap so that opening the drain (e.g., by removing a drain plug or opening a drain valve) causes immediate drainage of fluid from the fluid trap. In other embodiments, however, it may be advantageous to position the drain near the top of the fluid trap so that opening the drain does not immediately cause fluid to be expelled. Instead, a user can pour the fluid at a Se rate that is more easily controlled by the user.

Filter Medium Compression Systems

In some embodiments, after at least a portion of a fluid has been removed from the smoke using fluid traps (as described above), the partially processed smoke can be further filtered within the smoke evacuation system 120 (as illustrated, for example, in FIG. 32). Alternatively, in some embodiments, smoke is transferred directly from the vacuum hose 112 into the smoke evacuation system 120 (as shown, for example, in FIG. 1). Regardless of whether the smoke is preprocessed at a fluid trap or directly transferred to the smoke evacuation system 120 from vacuum hose 112, a smoke filter (e.g., smoke filter 700 illustrated in FIG. 48) can be used to remove particulate matter and gaseous pollutants from the smoke.

However, it can be difficult to process and/or filter smoke, as it can contain particulate matter of various sizes, volatile organic compounds, water vapor, and potentially other noxious chemicals and compounds. Traditionally, particulate matter can be removed from smoke using particulate filters, which have a wide range of airflow resistance and efficiency. For example, coarse media filters, which broadly include low air resistant filters such as fiberglass, polyester, and pleated filters, can be used to remove the majority of large particulate matter (e.g., greater than 10 µm). In some instances, coarse media filters can be used to remove at least 85% of large particulate matter (e.g., greater than 10 µm) and between 50%-95% of small particulate matter (e.g., between 1-3 µm). Some coarse media filters can remove greater than 95% of small particulate matter.

High efficiency particulate air (HEPA) filters and ultra-low penetration air (ULPA) filters can be used for filtering fine particulate matter. HEPA filters, for example, are defined by the U.S. Department of Energy as filters capable of removing at least 99.97% of airborne particulate matter up to 0.3 µm in diameter. HEPA filters typically have a minimal airflow resistance compared to the higher efficiency ULPA filters. Although ULPA filters are typically associated with higher airflow resistance, ULPA filters are generally more efficient at filtering fine particulate matter. Most ULPA filters can remove at least 99.9995% of airborne particulate matter up to 0.12 am in diameter.

Particulate filters are, for the most part, not very effective at removing other contaminants, particularly those gaseous pollutants found within smoke like volatile organic compounds. Sorbent-based filters can remove a number of gaseous pollutants from air and smoke, including volatile organic compounds, by chemically cross-linking the gaseous pollutant to the surface of the sorbent, and because adsorption is dependent upon the surface area of the sorbent, activated carbon is an ideal sorbent. Activated carbon is highly microporous and offers a significant amount of surface area per unit volume.

Filters employing sorbents like activated carbon require surface exposure of the air or smoke to be filtered with the sorbent in order for adsorption to occur. As it can be appreciated, therefore, the amount of surface area exposed to the air or smoke to be filtered is generally proportional to the amount or efficiency of filtration, and it is desirable to limit any gaps or routes through a sorbent-based filter that minimize surface area exposure thereto.

Figure 48:
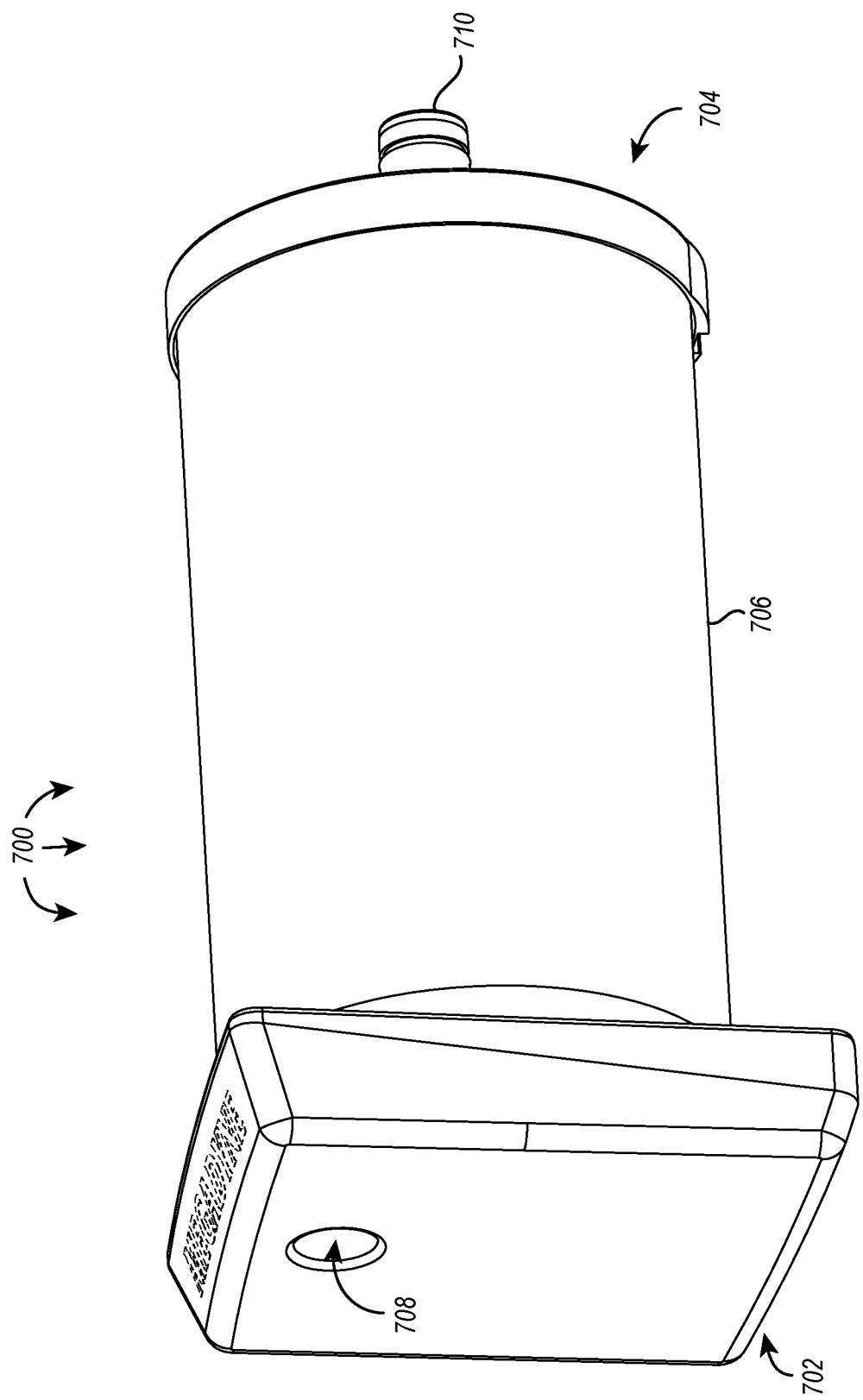
FIG. 48 illustrates an exemplary smoke filter for use with a smoke evacuation system.

Referring now to FIG. 48, illustrated is a smoke filter 700, which can be used with smoke evacuation systems disclosed herein. The smoke filter 700 includes a front cap 702 and a back cap 704 and a filter body 706 disposed of therebetween. As shown, the front cap 702 can include a filter inlet 708, which in some embodiments, receives smoke directly from a vacuum hose or other smoke source, or alternatively, the smoke inlet may associate with a fluid trap exhaust port to communicate partially processed smoke into the smoke filter 700. In some embodiments, the front cap 702 is replaced by a fluid trap that communicates smoke directly from the smoke source, and after removing at least a portion of the fluid therefrom, passes the partially processed smoke into the filter body 706 for further processing.

Regardless of the source, once smoke enters the filter 700, it is filtered by components housed within the filter body 706, and exits the filter 700 through the filter exhaust 710 defined by the back cap 704. As shown in FIG. 48, the filter body 706 of smoke filter 700 is cylindrical. It should be appreciated, however, that the size and/or shape of the filter body can be different. For example, the filter body can be a rectangular solid or other polygonal solid. Similarly, the front cap 702 and back cap 704 are shown as having arcuate cross-sections complementary to the shape of the filter body 706 where the front and back caps 702, 704 are coupled to the filter body 706, and the cross-sectional geometry of the front and back caps can be changed to match the shape of the filter body. In some embodiments, the filter exhaust 710 is sized and shaped to communicate with the smoke evacuation system, and the shape and/or placement of the filter exhaust 710 can remain unchanged, regardless of the size and shape the front cap 702 and/or filter body 706.

Figure 49:
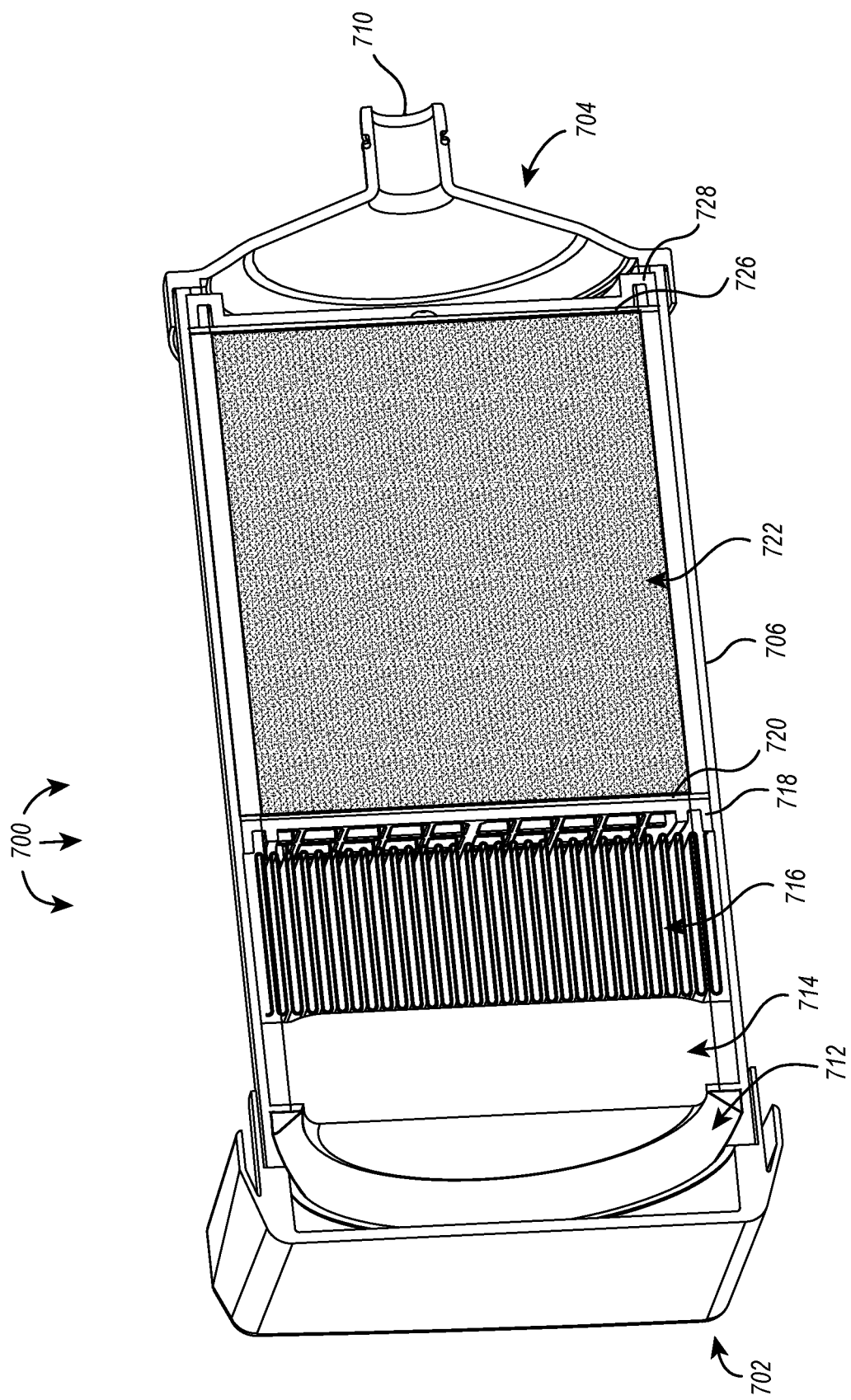
FIG. 49 illustrates a cross-section along the longitudinal axis of the exemplary smoke filter of FIG. 48, revealing various components therein.

When the filter 700 is associated with a smoke evacuation system, suction generated at the smoke evacuation system can be communicated to the filter 700 through the filter exhaust 710 to pull smoke through each of the internal filtering components of the filter 700. An exemplary embodiment of filtering components contained within smoke filter 700 is illustrated in FIG. 49. As shown, smoke entering the smoke filter 700 is initially drawn through a coarse media filter 714 followed by a fine particulate filter 716. The smoke is then drawn through a carbon reservoir 722 where gaseous contaminants such as volatile organic compounds are removed. The filtered smoke, which is now substantially free of particulate matter and gaseous contaminants, is drawn through the filter exhaust 710 and into the smoke evacuation system for further processing and/or elimination.

In some embodiments, the filter 700 can include a plurality of defined sections which can be cordoned off by one or more dams and/or dividers. As shown in FIG. 49, the smoke filter 700 can include a particulate filtration section that includes the coarse media filter 714 and the fine particular filter 716 flanked by dams 712, 718. The initial dam 712 of the particulate filtration section can be secured to an inner wall of the filter body 706 at a first end of the filter 700 proximate the front cap 702 and a first particulate filter (e.g., the coarse media filter 714) within the filter body 706. As shown in FIG. 49, the initial dam can be shaped as a gasket or O-ring and can act to prevent movement of downstream filters towards the first end or front cap 702 of the filter 700.

The particulate filtration section of the filter 700 can be defined at an intermediate position within the filter body 706 by intermediate dam 718, which prevents movement of the upstream particulate filters 714, 716 toward the back cap 704. As shown in FIG. 49, the intermediate dam 718 can be shaped as a perforated disc that allows filtered smoke to freely pass through the perforations while the non-perforated sections act as a physical barrier to prevent upstream filters from moving further downstream and/or distending in the direction of applied suction.

In some embodiments, the initial dam 712 and the intermediate dam 718 are spaced apart such that the particulate filters placed therebetween are secure. In some instances, the particulate filters being secured between the initial and intermediate dams 712, 718 results in a substantial lack of lateral mobility. For example, as shown in FIG. 49, the coarse media filter 714 and fine particular filter 716 are disposed between the initial dam 712 and intermediate dam 718 such that the filters 714, 716 cannot move laterally (e.g., directionally towards or away from dams 712, 718). The size and shape of the dams, particularly intermediate dam 718 can, in some embodiments, be chosen to further prevent distention of the filters in the direction of applied suction.

The coarse media filter 714 illustrated in FIG. 49 can include any low air resistant filter, such as fiberglass, polyester, and pleated filters, that remove the majority of particulate matter larger than 10 µm. In some embodiments, this includes filters that remove at least 85% of particulate matter larger than 10 µm, greater than 90% of particulate matter larger than 10 µm, greater than 95% of particular matter larger than 10 µm, greater than 99% of particular matter larger than 10 µm, greater than 99.9% particulate matter larger than 10 µm, or greater than 99.99% particulate matter larger than 10 µm.

Additionally, or alternatively, the coarse media filter 714 can include any low air resistant filter that removes the majority of particulate matter greater than 1 µm. In some embodiments, this includes filters that remove at least 85% particulate matter larger than 1 µm, greater than 90% of particulate matter larger than 1 µm, greater than 95% of particular matter larger than 1 µm, greater than 99% of particular matter larger than 1 µm, greater than 99.9% particulate matter larger than 1 µm, or greater than 99.99% particulate matter larger than 1 µm.

The fine particulate filter 716 illustrated in FIG. 49 can include any filter of higher efficiency than the coarse media filter 714. This includes, for example, filters that are capable of filtering a higher percentage of the same sized particles as the coarse media filter 714 and/or capable of filtering smaller sized particles than the coarse media filter 714. In some embodiments, the fine particulate filter 716 can include a HEPA filter or an ULPA filter. Additionally, or alternatively, the fine particulate filter 716 can be pleated (as shown in FIG. 49) to increase the surface area of the fine particulate filter. In some embodiments, the coarse media filter 714 include a pleated HEPA filter and the fine particulate filter 716 includes a pleated ULPA filter.

Subsequent to particulate filtration, smoke enters a downstream section of the filter 700 that includes a carbon reservoir 722. In some embodiments, the carbon reservoir 722 is flanked by the intermediate dam 718 and a terminal dam 728. The terminal dam 728 can, in some embodiments, have the same shape and/or properties described above with respect to the intermediate dam 718. The carbon reservoir 722 can additionally be bounded by porous dividers 720, 726 disposed between the intermediate and terminal dams 718, 728. In some embodiments, the porous dividers 720, 726 are rigid and/or inflexible and define a constant spatial volume for the carbon reservoir 722.

In some embodiments, the carbon reservoir includes additional sorbents that act cumulatively with or independently from the carbon particles to remove gaseous pollutants. The additional sorbents can include, for example, sorbents such as magnesium oxide and/or copper oxide, which can act to adsorb gaseous pollutants such as carbon monoxide, ethylene oxide, and/or ozone. In some embodiments, the additional sorbents are dispersed throughout the reservoir or are positioned in distinct layers above, below, or within the reservoir.

Referring now to FIGS. 50-55, illustrated are simplified cross-sectional illustrations of smoke filters which can be in many respects similar to the smoke filter 700 described above. Many of the internal components of the smoke filters illustrated in FIGS. 50-55, however, have been removed for ease of illustration and discussion. It should be appreciated that the smoke filters shown in FIGS. 50-55 can include any number or combination of filter components illustrated in FIG. 49 or otherwise known in the art.

Figure 50:
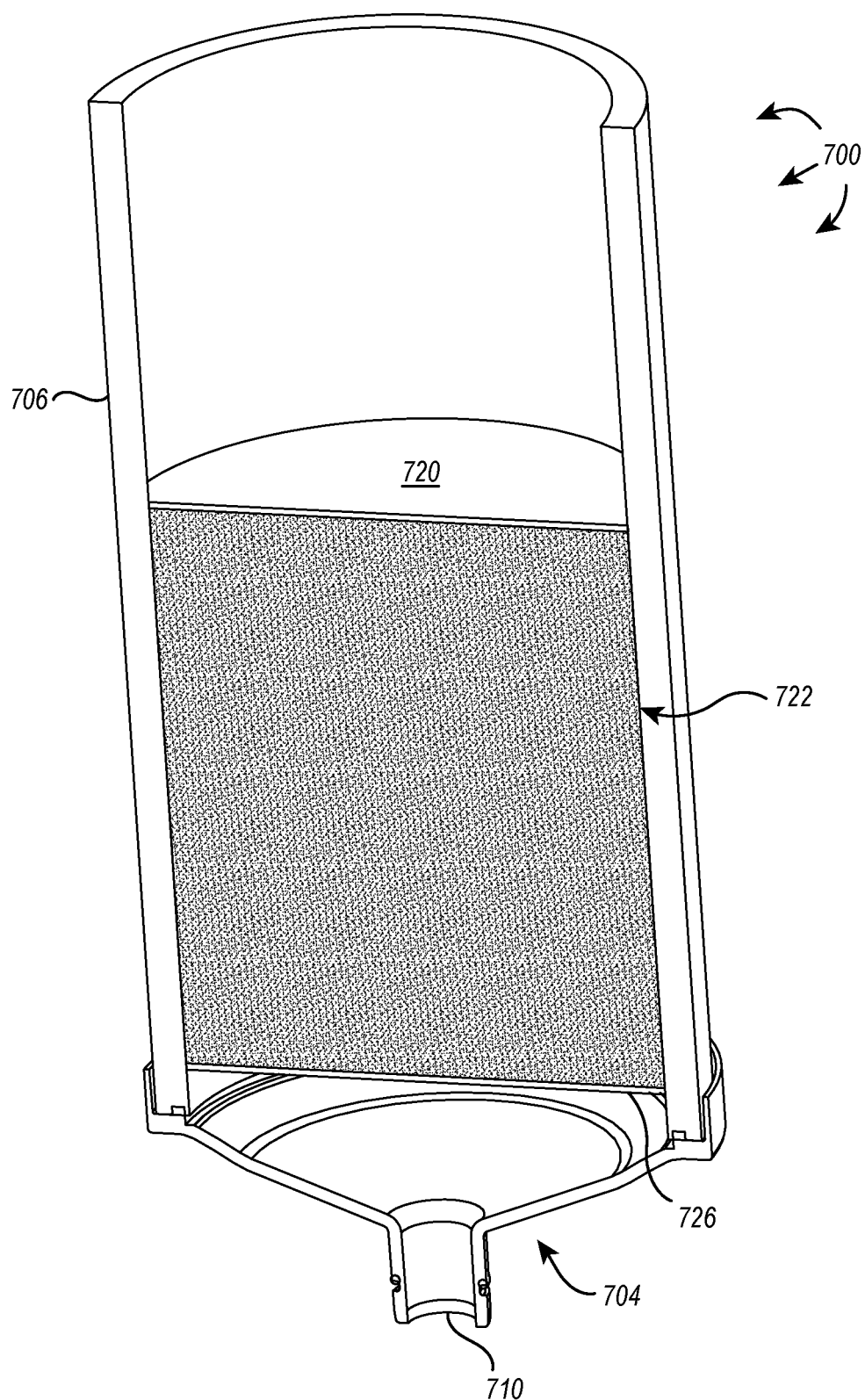
FIG. 50 illustrates a simplified view of the cross-section illustrated in FIG. 49 that emphasizes the carbon reservoir.

FIG. 50, for example, illustrates the smoke filter 700 with the carbon reservoir 722 bounded on opposite ends by porous dividers 720, 726. In some embodiments, the carbon reservoir 722 is compressed within the volume defined by the porous dividers 720, 726 when manufactured. Problematically however, the carbon reservoir 722 can settle to a smaller spatial volume over time, or when suction is applied through the carbon reservoir 722 from the filter exhaust 710, the carbon reservoir may be compacted to a smaller spatial volume. The settling or compacting of the carbon reservoir into a smaller spatial volume can create a gap within the reservoir that was previously occupied by carbon particles. In some embodiments, this can result in a nonuniform distribution of carbon particles within the reservoir, which can reduce the efficiency of adsorption and thereby reduce the effectiveness of the filter. In extreme instances, the carbon particles can settle to create a route through the reservoir that is devoid of carbon particles, allowing smoke to transit a portion or the entire length of the carbon reservoir without being adequately filtered.

Figure 51:
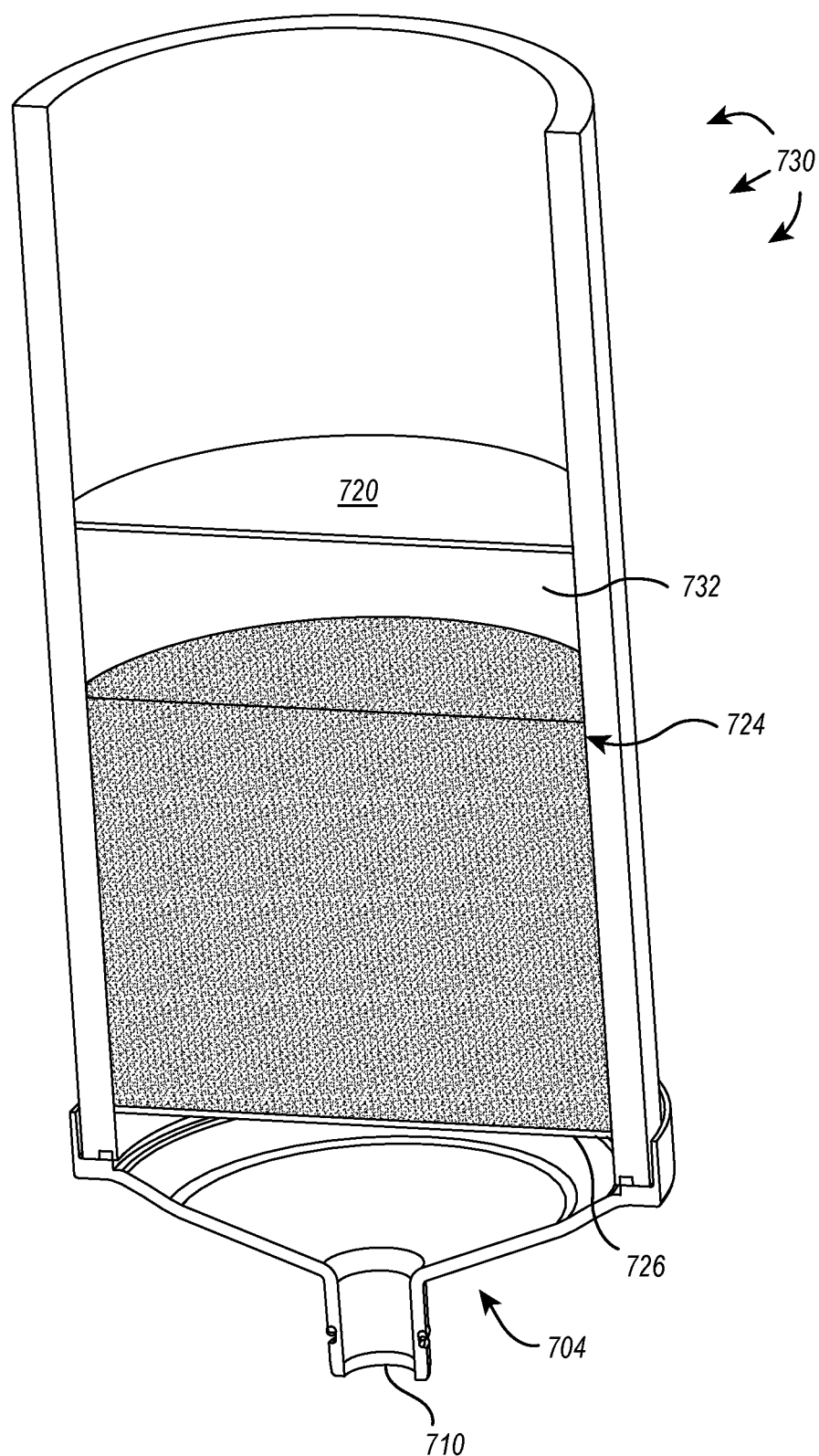
FIG. 51 illustrates the simplified view of FIG. 50 with a volumetric decrease in the carbon reservoir.

FIG. 51 illustrates a smoke filter 730 having a compacted carbon reservoir 724 that has settled over time or in response to pressure from suction communicated to the filter from a smoke evacuation system. As shown, a gap 732 is present between the compacted carbon reservoir 724 and an upstream divider 720. In some embodiments, the compacted carbon reservoir 724 filled the gap 732 before the carbon particles settled or were otherwise compacted. As shown in FIG. 51, the porous divider 720 does not move from its originally installed location as the carbon particles reorient because the porous divider 720 was fixed to the sidewalls of the smoke filter to define the carbon reservoir and/or to maintain the compressed state of the carbon reservoir.

In some embodiments, the porous divider can be replaced by a flexible porous barrier that enables the flexible porous barrier to maintain interaction with the carbon reservoir as it decreases in volume due to settling or a result of suction pressure. In doing so, the flexible porous barrier prevents gaps or channels from forming within the carbon reservoir that would otherwise decrease the efficiency or effectiveness of the carbon reservoir as a filter for gaseous contaminants.

Figure 52:
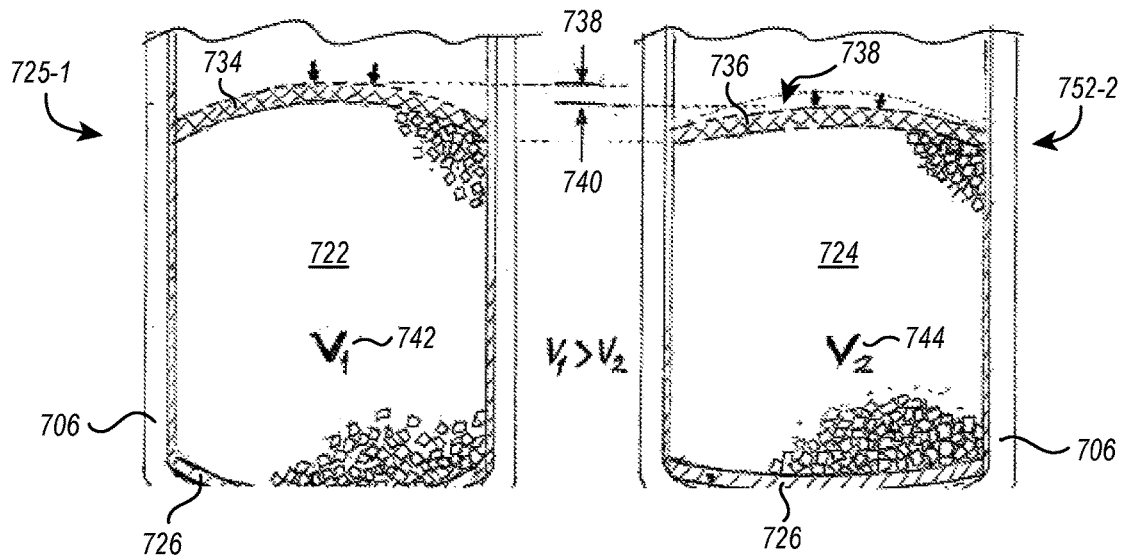
FIG. 52 illustrates cross-sections before and after a volumetric shift within a filter having a flexible porous barrier.

For example, as shown in FIG. 52, a smoke filter 725-1 includes a carbon reservoir 722 bounded on at least one end by a flexible porous barrier. The carbon reservoir 722 can be bounded on an opposing end by an inflexible porous divider 726, or in some embodiments, the carbon reservoir 722 can be bounded on an opposing end by a second flexible porous barrier (not shown). The carbon reservoir 722 is shown as occupying a first spatial volume 742—denoted $V_1$. Smoke filter 752-2 of FIG. 52 illustrates a compacted carbon reservoir 724 after settling of the carbon reservoir 722. The compacted carbon reservoir 724 now occupies a second spatial volume 744—denoted $V_2$—which is less than the first spatial volume 742. At the first spatial volume 742, the flexible porous barrier 734 is flexed and applying a compressive bias 738 against the carbon reservoir 722. As the carbon particles shift to form the compacted carbon reservoir 724, the flexed, flexible porous barrier 734 moves from a first position 739 to a second position 740 maintaining contact with the carbon particles to prevent gap formation. The partially relaxed, flexible porous barrier 736 can continue to apply a compressive bias 738 against the compacted carbon reservoir 724, and in some embodiments, the partially relaxed, flexible porous barrier 736 can move to a third position (or a plurality of subsequent positions) while continuing to apply a compressive bias against the carbon particles within the reservoir in preventing gap formation.

In some embodiments, the flexible porous barrier can flex outward, opposite the compressive bias in response to an unsettling force within the carbon reservoir. For example, the carbon particles may settle or become compacted through continuous pressure applied by suction from the smoke evacuation system. The associated flexible porous barrier may remain associated with the carbon particles as they settle, preventing gap formation (as described above). However, upon release of suction (e.g., turning the power off of the smoke evacuation system), the carbon particles may exert an outward force against the flexible porous barrier and causing it to flex toward its original position and/or return to its original position.

FIG. 52 illustrates the flexible porous barrier 734 applying a compressive bias 738 against the carbon reservoir 722 at a first side of the carbon reservoir. In some embodiments, the flexible porous barrier 734 is proximate the particulate filtration section of the smoke filter, or alternatively, the flexible porous barrier 734 is proximate the back cap. In yet other embodiments, the porous divider 726 of FIG. 52 is replaced with a second flexible porous barrier such that a flexible porous barrier defines two opposing ends of the carbon reservoir 722. It should be appreciated that regardless of the positioning or location of a flexible porous barrier with respect to the carbon reservoir, the carbon particles within the carbon reservoir may shift or settle at any position therein, and the compressive bias applied against the carbon reservoir can cause any gap or channel formed by the shifting particles to be successively filled by carbon particles disposed between the flexible porous barrier and the shifting particles.

Figure 53:
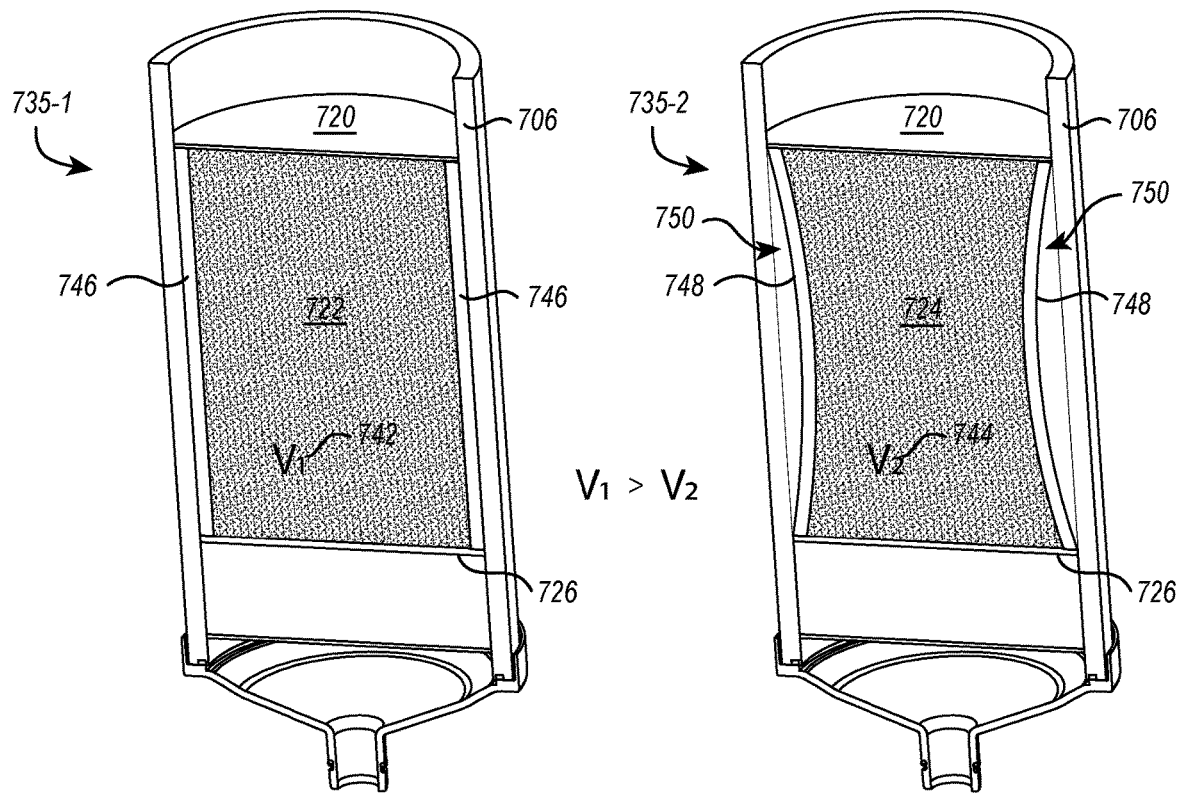
FIG. 53 illustrates cross-sections before and after a volumetric shift within another filter having a flexible porous barrier.

In some embodiments, and as illustrated in FIG. 53, a smoke filter 735-1 can include a flexible sleeve 746 that is flexed or otherwise applying an inward compressive bias against the carbon reservoir 722. Upon the carbon particles shifting from a first spatial volume 742 to a second spatial volume 744, the flexible sleeve 746 moves to a partially relaxed state, creating a gap 750 between the interior sidewall of the filter body 706 and the sleeve 748. Although FIG. 53 is illustrated as a cross-section, it should be appreciated that the sleeve 748 may, in some embodiments, wrap circumferentially around the carbon reservoir 722, 724.

Figure 54:
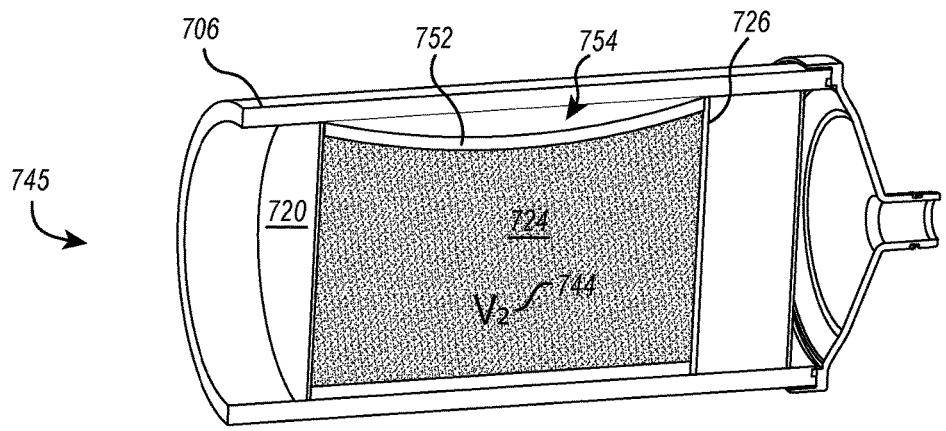
FIG. 54 illustrates a cross-section after a volumetric shift within a filter having a flexible porous barrier.

In some embodiments, and as illustrated in FIG. 54, a smoke filter 745 can include a flexible sleeve 752 that is positioned on one side and/or only partially around the carbon reservoir 724. In such an embodiment, the flexible sleeve 752 may be positioned such that when the smoke filter 745 is associated with the smoke evacuation device, the compressive bias exerted by the flexible sleeve 752 is against the carbon reservoir 724 in a direction parallel to the force of gravity. In some embodiments, the flexible sleeve 752 can be positioned about at least a portion of the carbon reservoir 724 irrespective of the directional force of gravity.

Figure 55:
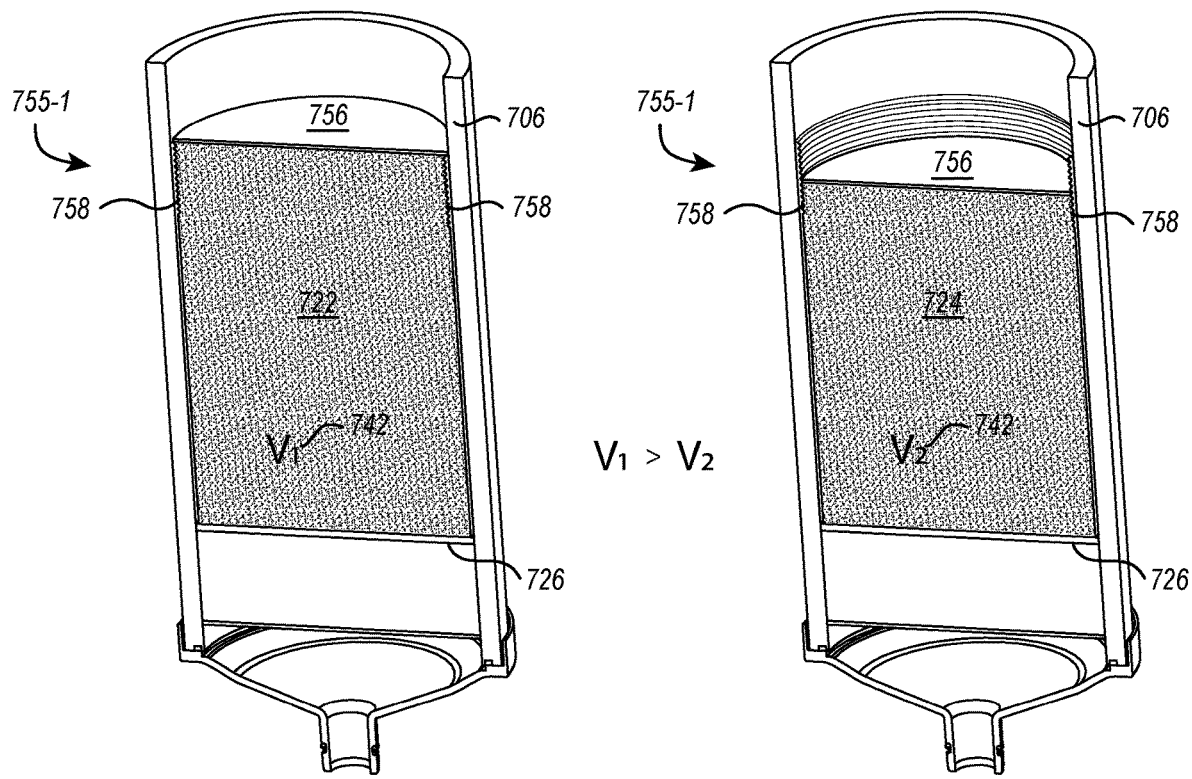
FIG. 55 illustrates cross-sections before and after a volumetric shift within a filter having a ratcheting porous barrier.

In some embodiments, a smoke filter 755-1 includes a rigid, porous barrier 756 associated with an outermost portion of the carbon reservoir 722 distal to the source of suction, as illustrated in FIG. 55. Upon shifting of carbon particles within the carbon reservoir 722 and moving from a first spatial volume 742 to a second spatial volume 744, the rigid, porous barrier ratchets down a plurality of ridges associated with the interior sidewall of the filter body 706, thereby decreasing the volume of the carbon reservoir. In some embodiments, the energy from moving the rigid, porous barrier 756 along the ridges 758 is at least partially obtained from a lack of pressure beneath the rigid, porous barrier 756—as a result of the particles shifting away from or being capable of shifting away from the barrier 756 to form a smaller, second spatial volume 744.

Additionally, or alternatively, the rigid, porous barrier 756 can be weighted more heavily such that the force of gravity causes the barrier 756 to automatically lower itself along the ridges 758 when there is sufficient space to do so. In some embodiments, the suction pressure can act to pull the barrier 756 along the ridges as there is sufficient space to do so. In some embodiments, an additional flexible member (not shown) is positioned between the barrier and another component of the filter (e.g., a dam or cap) and biases against the barrier, causing the barrier to maintain contact with the carbon particles within the reservoir as the spatial volume decreases. In some embodiments, the flexible member is a spring member that forces the barrier 756 to maintain contact with the carbon particles within the reservoir and lowers the barrier 756 along the ridges 758 when there is sufficient space to do so.

Embodiments described herein can provide a number of benefits. For example, during an electrosurgical procedure, a portion of the generated smoke can be captured and transited to a smoke evacuation system for processing and filtration. As the smoke may include particulates and gaseous pollutants, which can potentially be toxic if inhaled, decrease visibility, or at the very least be potentially odoriferous, it is advantageous to filter the smoke to a more purified state. The smoke filters described above can enable smoke to be adequately filtered.

Additionally, the smoke filters described above can prevent inefficiencies associated with gap formation when the charcoal reservoir is compacted from a starting volume to a smaller settled volume. For example, the carbon reservoir of smoke filter may compress to a smaller settled volume when under constant pressure of suction from the smoke evacuation device. This may cause gaps to form within the carbon reservoir, and smoke entering into the carbon reservoir to be filtered can pass around or through the gaps minimizing the surface area contact within the carbon reservoir. This reduced surface area contact can result in less adsorption of contaminants, and in some extreme instances, a channel may be formed partially or entirely around the carbon reservoir preventing filtration therethrough. In some embodiments, settling of the carbon particles within the reservoir may cause the carbon particles to fill a smaller spatial volume regardless of pressure. The addition of one or more flexible porous barriers and/or flexible sleeves can provide a compression bias against the particles within the carbon reservoir such that any decrease in volume causes the flexible porous barrier and/or flexible sleeve to contract inward, preventing gaps from forming.

By maintaining a solid carbon reservoir without gaps, the efficiency of the filter can be maintained or increased. Smoke being filtered through the carbon reservoir maintains contact with the surface area of carbon particles more consistently as it traverses the reservoir in beneficially increasing the efficiency of the filter.

Remote Activation

As explained in greater detail below, embodiments of electrosurgical systems according to the present disclosure enable efficient activation and dynamic capture of smoke generated during an electrosurgical procedure. For example, vacuum suction originating from the smoke evacuation device 120 can be activated and/or adjusted by a sensor that detects activation of RF current and turns on the vacuum suction in response to detecting activation of RF current and that monitors the RF current, adjusting the flow rate and/or temporal duration of vacuum suction based on the monitored RF current.

Current smoke evacuation devices are inefficient and unresponsive to user interaction with components of electrosurgical systems. For example, current smoke evacuation devices are typically turned on or activated before the electrosurgical procedure begins, and the smoke evacuation device is left running for the duration of the electrosurgical procedure. In doing so, any smoke generated during the procedure can be captured and collected from the surgical site and conveyed to the smoke evacuation device for filtering and processing. However, smoke is not continually generated, leaving the smoke evacuation device to convey and filter/process environmental air during non-smoke-generating periods.

In some instances, the smoke filter associated with the smoke evacuation device is monitored for a total number of hours used. That is, the total amount of time the smoke evacuation device is on and providing suction—and therefore pulling air through the smoke filter—is the determinative factor for calculating the life span of the smoke filter, regardless of how many hours the smoke filter was actually being used to filter smoke. Even if the smoke filter was processing relatively clean environmental air for 90% of its temporal life span and would otherwise be deemed clean/useable, many regulations and protocols require the smoke filter to be replaced after so many hours of use. These precautions are intended to guard against the use of clogged or dirty filters, but in practice, it typically results in a tremendous amount of product waste, increased costs, and other inefficiencies within electrosurgical systems.

Additionally, most smoke evacuation devices are not responsive to the variable amount of smoke that can be created throughout an electrosurgical procedure. For example, a great deal of smoke may be generated at various interspersed times during the procedure such as when first cutting tissue at the surgical site or during excision or repair of tissue, whereas at other times, there may be little or no smoke generated such as when the surgeon is performing small delicate incisions or when the surgeon is not using the electrosurgical instrument at all. Regardless of the smoke generation, the smoke evacuation device is likely to be providing constant suction.

In some embodiments, the amount of suction can be manually adjusted, but doing so may detract from the task at hand and can be burdensome to continually monitor and adjust. Further, it may be the case that by the time the user realizes that additional suction is required due to an increased production of smoke, it is likely too late. By the time the suction is adjusted, the smoke will have likely dissipated, making it difficult—if not impossible—to adequately capture and convey to the smoke evacuation device.

One or more embodiments disclosed herein beneficially enable the detection of electrical current within an electrosurgical system and initiate a corresponding activation or modulation of vacuum suction at the smoke evacuation device. Additionally, in some embodiments, a treatment power is derived from the detected current, and based on the derived treatment power, the smoke evacuation device is activated for a defined duration and/or at a defined smoke evacuation flow rate. In some embodiments, the derived treatment power is used to calculate an estimated smoke production, and the smoke evacuation device is activated for a defined duration and/or at a defined smoke evacuation flow rate based on the estimated smoke production.

In some embodiments, an RF current sensor is configured to operate in at least two modes—a first mode and a second mode—and includes a sensor body having at least a cable interfacing sidewall and a retaining member. The cable interfacing sidewall and the retaining member define a retention pocket configured to receive a cable communicating RF current. The RF current sensor additionally includes a sensor element for detecting RF current in the cable and a sensor cable in electrical communication with the sensor element. The sensor cable communicates one or more of an activation signal or a current signal derived from the detected RF current to the smoke evacuation device.

In some embodiments, a method for remote activation of a smoke evacuation device includes generating an RF current at a signal generator, communicating the RF current through a source cable to an electrosurgical instrument, detecting an activation of RF current with an RF current sensor communicatively coupled to a smoke evacuation device, communicating an activation signal from the RF current sensor to the smoke evacuation device in response to detecting the activation of RF current, receiving the activation signal at the smoke evacuation device, and activating a vacuum source for one or more of a defined period of time or to generate a defined smoke evacuation flow rate in response to receiving the activation signal.

In some embodiments, an electrosurgical system includes a signal generator producing an RF current, a source cable electrically coupled to the signal generator and to an electrosurgical instrument, the source cable communicating the RF current from the signal generator to the electrosurgical instrument, a smoke evacuation device that includes a vacuum hose positioned proximate the electrosurgical instrument and configured to evacuate smoke generated by the electrosurgical instrument, and an RF current sensor communicatively coupled to the smoke evacuation device, the RF current sensor activating the smoke evacuation device in response to identifying the RF current.

Such foregoing embodiments of the present disclosure along with additional, or alternative, embodiments described herein can provide a number of benefits. For example, during an electrosurgical procedure, an electrosurgical instrument can be activated for a variable amount of time and/or for variable durations, and this can directly affect the amount and timing of smoke generated during the electrosurgical procedure. Implementations of the present application beneficially enable an associated smoke evacuation device to be activated in response to activation of the electrosurgical instrument and concomitant smoke generation instead of being run constantly. This will reduce the overall time the smoke evacuation device is activated during individual procedures and thereby provide energy savings and increase the life of the smoke evacuation device and/or its components. For example, smoke filters associated with the smoke evacuation device can benefit from an increased life span and/or be more efficiently used by predominantly filtering smoke instead of passively filtering air from a constantly running smoke evacuation device.

In another example, the ability to detect current activation, intensity, and/or duration allows implementations of the present disclosure to adjust the flow rate to accommodate an estimated increase or decrease in smoke generation, thereby providing automatic, dynamic, and responsive smoke evacuation without burdensome oversight, monitoring, or manual adjustments. This can beneficially reduce any visibility reduction, odor, and other problems associated with smoke generation. In some instances, this can enable electrosurgical procedures that generate greater amounts of smoke to be performed or to be performed with less ancillary equipment (e.g., less additional independent vacuum hoses, fans, and other air management equipment) as it can dynamically respond to the smoke generated during the electrosurgical procedure.

Figure 56:
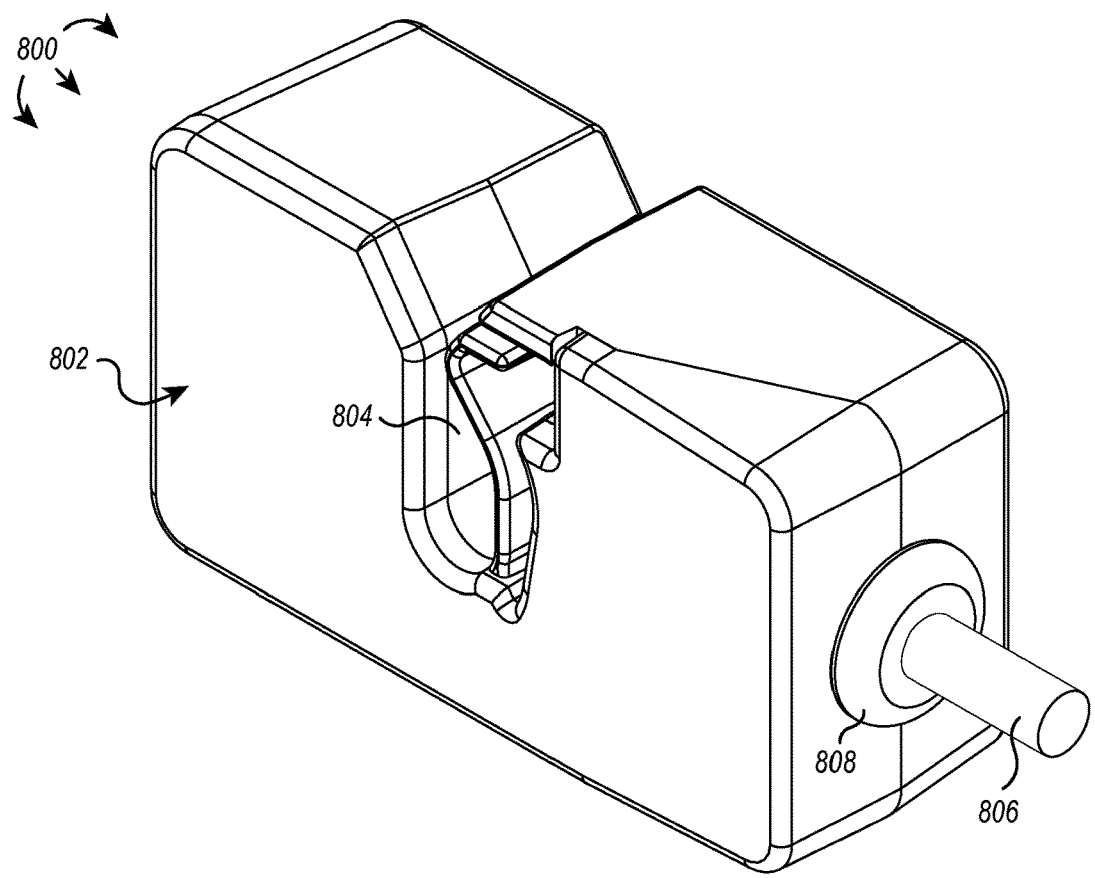
FIG. 56 illustrates a perspective view of an exemplary remote activation clip.
Figure 57:
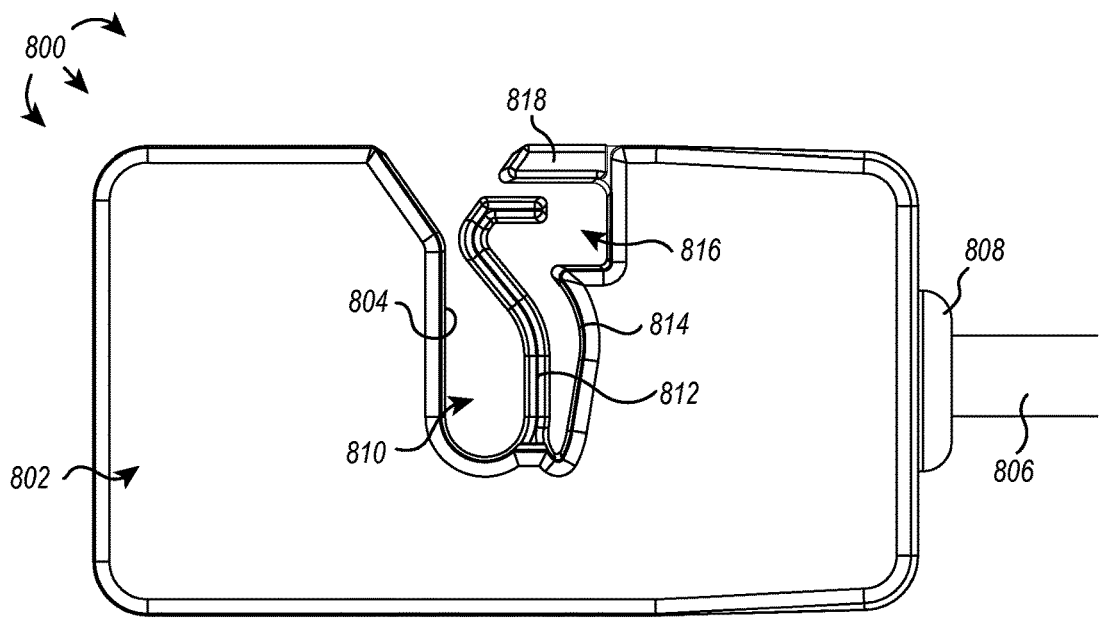
FIG. 57 illustrates an elevation view of the exemplary remote activation clip of FIG. 56.

Referring now to FIGS. 56 and 57, illustrated are perspective and elevation views, respectively, of an exemplary RF current sensor 800. As shown, the RF current sensor 800 includes a sensor body 802 defining most of the visible exterior surfaces of the RF current sensor 800. The RF sensor 800 is associated with a sensor cable 806 at a first end thereof and is retained in place or coupled to the RF sensor 800 by grommet 808. Although depicted as being disposed on a short side of the RF current sensor 800, in some embodiments, the grommet 808 and/or the sensor cable 806 can be disposed on/through any front, side, top, or bottom surface of the RF current sensor 800.

As perhaps best shown in FIG. 57, the sensor body 802 includes a cable interfacing sidewall 804 that at least partially defines a retention pocket 810. The retention pocket is also at least partially defined by the retaining member 812. The retaining member 812 is configured to flex or bend, and in some embodiments—and as illustrated in FIGS. 56 and 57—the RF current sensor 800 can be shaped to accommodate the bending or flexing of the retaining member 812. For example, the sensor body 802 includes a recess sidewall 814 that together with the retaining member 812 and protruding ridge 818 at least partially define a recess 816 into which the retaining member 812 can bend or flex.

The retaining member 812 is illustrated as having a substantially linear lower body that is substantially parallel with the opposing cable interfacing sidewall 804 followed by an arcuate upper body that initially creates a concavity directed towards the retention pocket 810 and narrowing the distance between the cable interfacing sidewall 804 and the retaining member 812. The narrowed distance can serve to prevent unintentional attachment of the RF current sensor 800 to other objects and can also serve to prevent the RF current sensor 800 from unintentionally detaching from an object (e.g., a cable) disposed within the retention pocket 810.

In some embodiments, the retaining member 812 can be biased or flexed towards the recess sidewall 814 and/or into the recess 816, widening the distance between the upper body of the retaining member 812 and the cable interfacing sidewall 804. By doing so, an object can be passed into the retention pocket 810, wherein upon release of the flexed retaining member 812, the object is secured within the retention pocket 810 (e.g., the retaining member 812 mechanically blocks egress of the object from the retention pocket 810).

Additionally, the protruding ridge 818 alone, or in combination with the stop member 815 running substantially parallel thereto, can act to prevent unintentional insertion of an object within the recess 816, which could prevent the retaining member 812 from flexing into the recess 816. Additionally, the length of the stop member 815 and/or the corresponding depth of the recess 816 can act to autoregulate the diameter of cable that can be inserted into the retention pocket 810. For example, a shorter stop member (assuming the same recess 816 depth) will allow the retaining member to flex more, widening the opening and allowing larger diameter cables to enter the retention pocket 810. On the other hand, a longer stop member (again assuming the same recess 816 depth) will prevent the retaining member from flexing and provide a narrower opening through which only smaller diameter cables can pass and enter the retention pocket 810. It should be appreciated that the depth of the corresponding recess 816 can similarly affect the diameter of cable that may enter the retention pocket 810. For example, a deeper recess (assuming the same stop member 815) will allow the retaining member to flex more, widening the opening and allowing larger diameter cables to enter the retention pocket 810 while a shallower recess (again assuming the same stop member 815) will prevent the retaining member from flexing and provide a narrower opening through which only smaller diameter cables can pass and enter the retention pocket 810.

In some embodiments, the stop member 815 and/or the recess 816 are sized to allow a source cable 110 or a return cable 118 to enter the retention pocket 810. Additionally, or alternatively, the stop member 815 and/or the recess 816 are sized to prevent admission of other cables into the retention pocket 810, such as a power cable for the generator 102 or a power cable for the smoke evacuation device 120 or to prevent admission of cable-like objects such as the vacuum hose 112.

The length and configuration of the retaining member 812 and stop member 815 with respect to other features of the RF current sensor 800 can provide additional benefits. For example, the retaining member 812 is contained within the six spatial planes that define the generally box-shaped RF current sensor 800 (e.g., as shown in FIG. 56). That is, the retaining member 812 does not extend or protrude in any direction outside of body of the RF current sensor 800, and this configuration beneficially protects the retaining member from catching on other cables, which could break the retaining member 812. This configuration also protects the retaining member 812 from impact damage if the RF current sensor 800 is dropped or stepped on. Further, because the retaining member 812 is not confluent with any of the six structural sidewalls that make up the box-like dimensions of the RF current sensor 800, it is protected from breakage resulting from a forceful extraction or insertion of a cable into the retention pocket. Additionally, the hard stop relationship between the stop member 812 and the recess 815 allow elastic deformations to the retaining member 812 while preventing plastic deformations or fracturing.

It should be appreciated that the retaining member 812 should not be limited to the exemplary illustration provided in FIGS. 56 and 57. Rather, in some embodiments, the retaining member can include any type or combination of geometries and spatial association with the cable interfacing sidewall. As a non-limiting example, the retaining member can include a horizontal member that encloses the retention pocket similar in form and function to a lid or latch. Additionally, the recess and/or protruding ridge may be omitted, in some embodiments—such as in the foregoing example. It should be noted, however, that embodiments including a horizontal member or that remove the horizontal member or the stop member may not benefit from all of the aforementioned advantages afforded to retaining member 812 of FIG. 57.

In some embodiments, the object retained within the retention pocket 810 is a cable. The cable can be any cable but preferably, the cable includes a source cable 110 or a return cable 118 associated with an electrosurgical system. The cable can serve as a conduit for transmitting RF current from a signal generator 102 to an electrosurgical instrument 104. In the case of a bipolar electrosurgical instrument, the cable can serve as both a source cable and a return cable. In the case of a monopolar electrosurgical instrument, the cable can be one or both of the source cable 110 electrically coupled between the signal generator 102 and the electrosurgical instrument 104 or the return cable 118 electrically coupled between the return electrode 106 and the signal generator 102.

Figure 58:
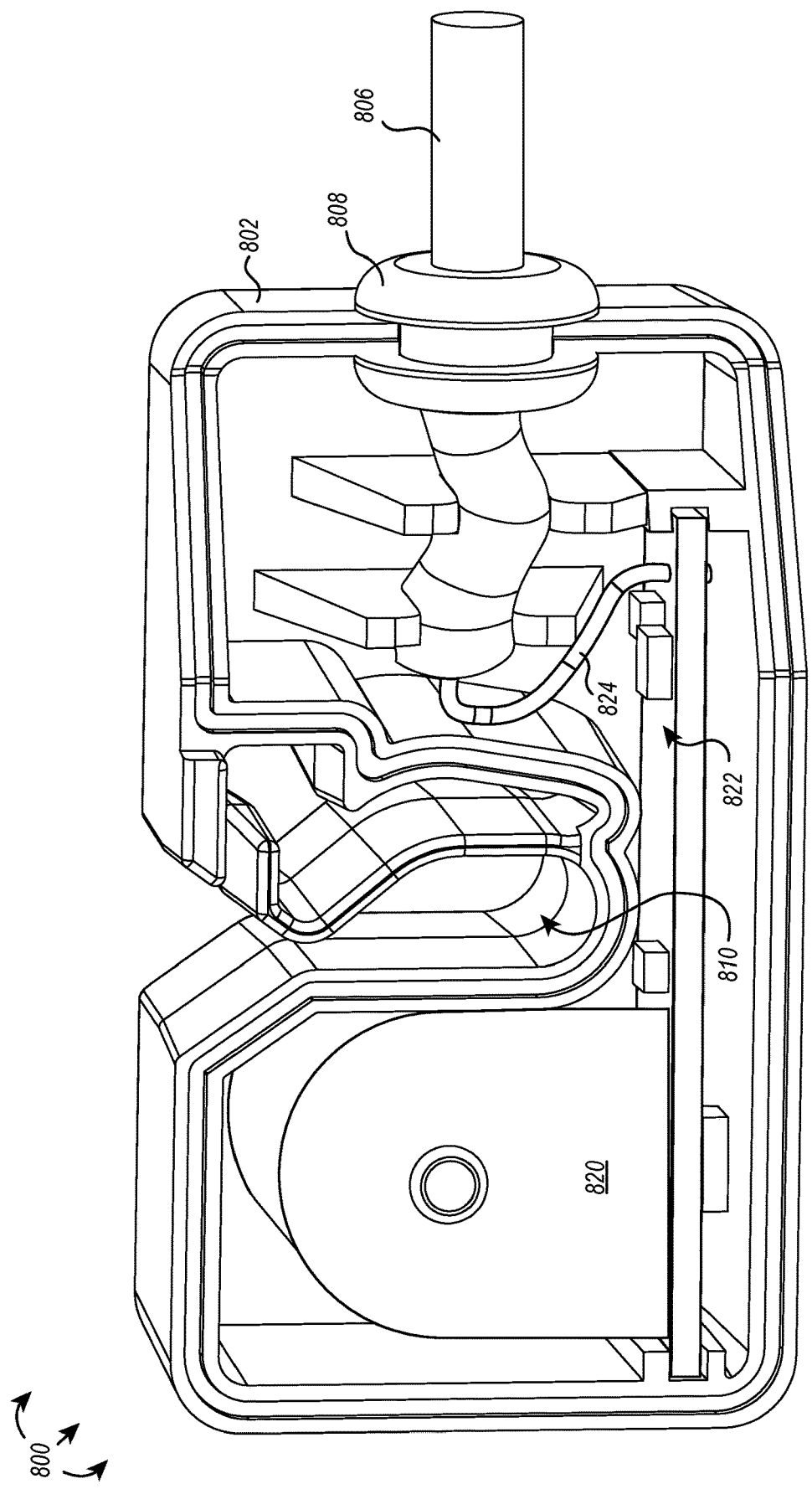
FIG. 58 illustrates a partial cross-sectional view of the exemplary remote activation clip of FIG. 56.

When the cable is disposed within the retention pocket 810, the RF current sensor 800 can detect activation of the RF current through the cable and/or the RF current passing through the cable. In some embodiments, and as shown in FIG. 58, the RF current sensor 800 can include a sensor element 820 housed within the sensor body 802 that detects the activation and/or current of the RF current passing through the cable retained within the retention pocket 810. The sensor element 820 can be any sensor that can detect current within the cable, including, for example, an RF current sensor.

In some embodiments, it may be difficult to detect activation of RF current and/or RF current with a single pass of the cable through the retention pocket 810. In a monopolar system, the RF current signal from the cable can be amplified by looping the cable multiple times through the retention pocket 810. In a bipolar system, the RF current signal can be amplified by separating the source and return strands and looping one of the source or return strands—but not the other—multiple times through the retention pocket 810.

Additionally, or alternatively, it may be advantageous for the sensor element to register detection of RF current above a lower or baseline threshold. For example, a cable may include a low base level of current passing therethrough, even when the electrosurgical instrument is not being used, which could give a false positive indication of RF current passing therethrough. In some embodiments, the baseline threshold is at least 1 mA, at least 5 mA, at least 10 mA, at least 25 mA, at least 50 mA, at least 75 mA, at least 100 mA, at least 150 mA, at least 200 mA, at least 300 mA, at least 400 mA, at least 500 mA, at least 600 mA, at least 700 mA, at least 800 mA, or at least 900 mA.

In addition to the sensor element 820, the sensor body 802 can house various additional internal components of the sensor 800. For example, as illustrated in FIG. 58, the RF current sensor 800 can include a printed circuit board (or similar electronic medium) in electrical communication with the sensor element 820 and which is also in electrical communication with a lead 824. The lead 824 can, in some embodiments, transmit analog data detected and transmitted by the sensor element 820. Additionally, or alternatively, the lead 824 can transmit digital data representative of the signal data (e.g., an activation signal and/or a current signal) detected by the sensor element 820.

In some embodiments, the sensor cable 806 communicates an activation signal or a current signal derived from the detected RF current to a smoke evacuation device. When received by the smoke evacuation device, the activation signal and/or current signal, can cause a vacuum source to be activated for a period of time and/or cause the vacuum source to generate a defined smoke evacuation flow rate. In some embodiments, the activation signal and/or the current signal are proportional to the detected RF current and thereby cause an effect at the smoke evacuation device that is commensurate with the detected signal.

For example, if the RF current sensor detects activation of the RF current, the sensor cable can communicate instructions to the smoke evacuation device to turn on the vacuum system to a low setting. If the RF current sensor fails to detect RF current thereafter, the sensor cable can communicate instructions to the smoke evacuation device to deactivate the vacuum system. In some embodiments, the deactivation is immediate. In other embodiments, the vacuum system runs for a defined period of time to ensure capture and conveyance of any smoke generated at the surgical site. It should be appreciated that the sensor cable can communicate any pre-defined (e.g., turn vacuum system on high) or user-defined instruction in response to the RF current sensor detecting activation of the RF current through the associated cable.

As an additional example, the if the RF current sensor detects activation of the RF current followed by sustained RF current, the sensor cable can communicate instructions to the smoke evacuation device to create a high smoke evacuation flow rate (e.g., by turning the vacuum system on its highest setting).

In some embodiments, the sensor cable 806 is physically coupled to the RF current sensor 800 and can electrically communicate with the RF current sensor 800 and the smoke evacuation device 120. In some embodiments, the sensor cable 806 is also physically coupled to the smoke evacuation device 120. In yet other embodiments, the sensor cable communicates wirelessly with the smoke evacuation device.

Figure 59:
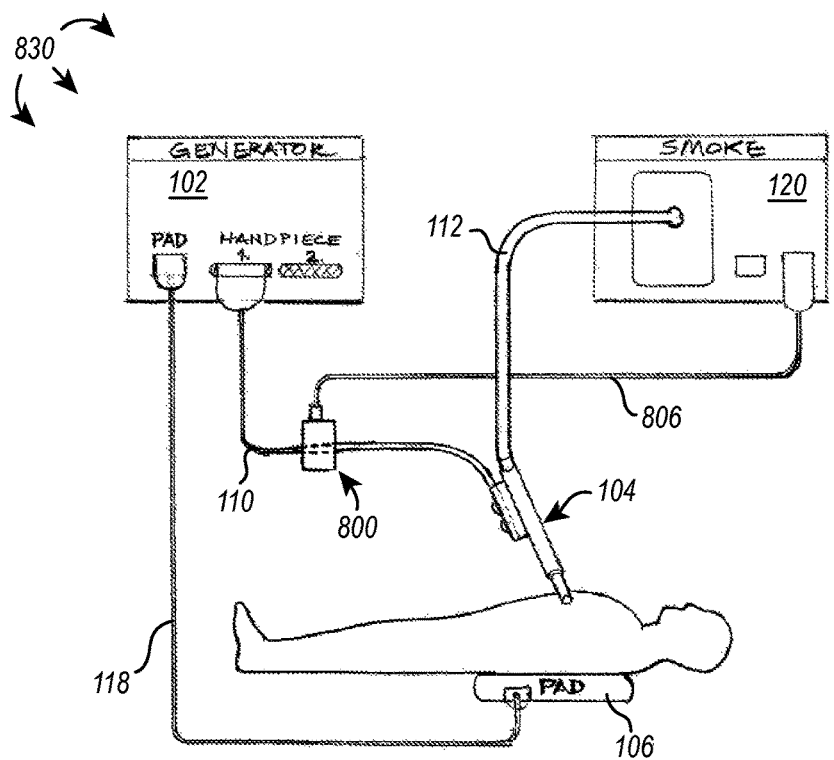
FIG. 59 illustrates a remote activation clip associated with a cable leading to the electrosurgical instrument of the depicted electrosurgical system.

As provided above, the RF current sensor 800 can, in some embodiments, selectively clip onto a source cable 110 and/or a return cable 118 and be retained thereon, detecting RF activation events and/or RF current through the cable 110, 118. For example, as illustrated in FIG. 59, an electrosurgical system 830 can include a signal generator 102 that generates an RF current and communicates the RF current to an electrosurgical instrument 104 (illustrated as a monopolar electrosurgical instrument) through a source cable 110. The RF current is transmitted through the patient and received at the return electrode 106, completing the circuit to the signal generator 102 through return cable 118. As illustrated, a vacuum hose 112 extends from the smoke evacuation device 120 to the surgical site proximate the electrosurgical instrument 104 and is positioned to extract smoke generated by the electrosurgical instrument 104 and convey the smoke to the smoke evacuation device 120 for filtering/processing.

The electrosurgical system 830 additionally includes an RF current sensor 800 removably associated with the source cable 110 and connected to the smoke evacuation device 120 by sensor cable 806. The RF current sensor 800 can detect an activation of RF current passing through the source cable 110, and in response to detecting the activation of RF current, the RF current sensor 800 can communicate an activation signal to the smoke evacuation device 120. In response to receiving the activation signal, the smoke evacuation device 120 can activate a vacuum source for a defined period of time or to generate a defined smoke evacuation flow rate. In some embodiments, the defined period of time or the defined smoke evacuation flow rate is proportional to the activation signal or a plurality of previously detected activation signals. For example, if the RF current sensor 800 detects a series of RF activation events in close temporal proximity, the RF current sensor 800 can instruct the smoke evacuation device 120 to activate the vacuum system for a prolonged period of time, as the plurality of detected activation signals can be indicative of successive electrosurgical events that can in the aggregate generate sufficient smoke to warrant prolonged smoke evacuation.

It should be appreciated that the RF current sensor 800 can additionally, or alternatively, detect RF current through source cable 110 and communicate instructions to the smoke evacuation device 120 in a similar fashion as described above.

Figure 60:
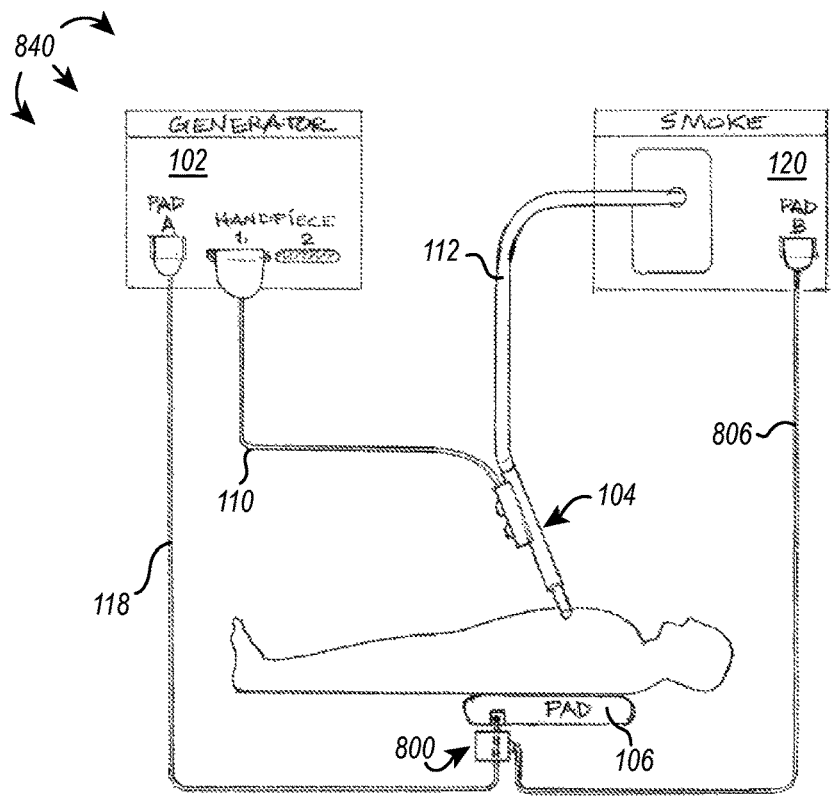
FIG. 60 illustrates a remote activation clip associated with a cable extending from the return electrode of the depicted electrosurgical system.

As shown in FIG. 60, an electrosurgical system 840 can include a similar setup as described above with respect to electrosurgical system 830. That is, an electrical circuit for transmitting RF current can be formed from the signal generator 102, to a source cable 110, electrosurgical instrument 104, return electrode 106, and return cable 118, completing the electrical circuit at the signal generator 102. Instead of the RF current sensor 800 being positioned on the source cable 110, as described above with respect to FIG. 59, the RF current sensor 800 is removably attached to the return cable 118. However, similar to the RF current sensor 800 of FIG. 59, the RF current sensor 800 of FIG. 60 is connected to the smoke evacuation device 120 by sensor cable 806.

The RF current sensor 800 of FIG. 60 can detect an activation of RF current passing through the return cable 118, and in response to detecting the activation of RF current, the RF current sensor 800 can communicate an activation signal to the smoke evacuation device 120. Similarly, it should be appreciated that the RF current sensor 800 can additionally, or alternatively, detect RF current through return cable 118 and communicate instructions to the smoke evacuation device 120 in a similar fashion as described above.

Figure 61:
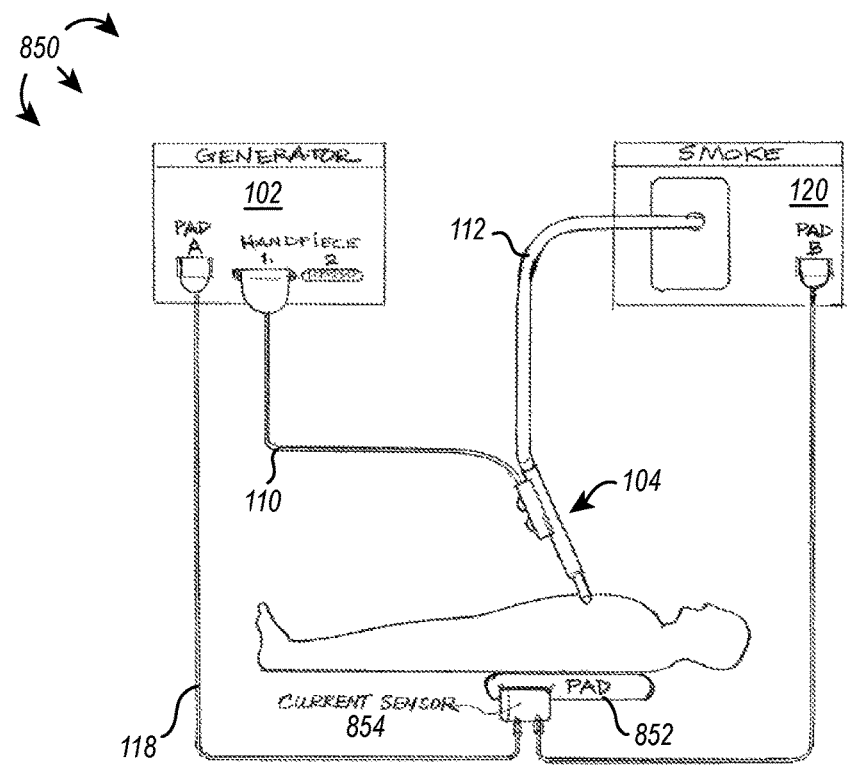
FIG. 61 illustrates a current sensor associated with the return electrode of the depicted electrosurgical system.

As shown in FIG. 61, an electrosurgical system 850 can include a similar setup as described above with respect to electrosurgical systems 830 and 840. That is, an electrical circuit for transmitting RF current can be formed from the signal generator 102, to a source cable 110, electrosurgical instrument 104, return electrode 852, and return cable 118, completing the electrical circuit at the signal generator 102. However, instead of the RF current sensor 800 being releasably connected to the source cable 110 (as in FIG. 59) or to the return cable 118 (as in FIG. 60), the RF current sensor 854 is integrally formed within the return electrode 852. The return electrode 852 includes pigtails or other electrical outlets that electrically couple the return electrode 852 to the signal generator 102, thereby completing the circuit, and also allow electrical coupling of the return electrode 852 with the smoke evacuation device 120 through a sensor cable 856.

The RF current sensor 854 within the return electrode 852 detects RF current activation as the RF current is received and passes through the return electrode 852. Additionally, the RF current sensor 854 can detect RF current passing through return electrode 852. In response to the current sensor 854 detecting RF current activation and/or the RF current passing through the return electrode 852, the current sensor 854 can communicate with the smoke evacuation device 120 to activate and modulate smoke evacuation flow rate and/or a period of time the smoke evacuation device 120 is activated, as described herein.

Figure 62:
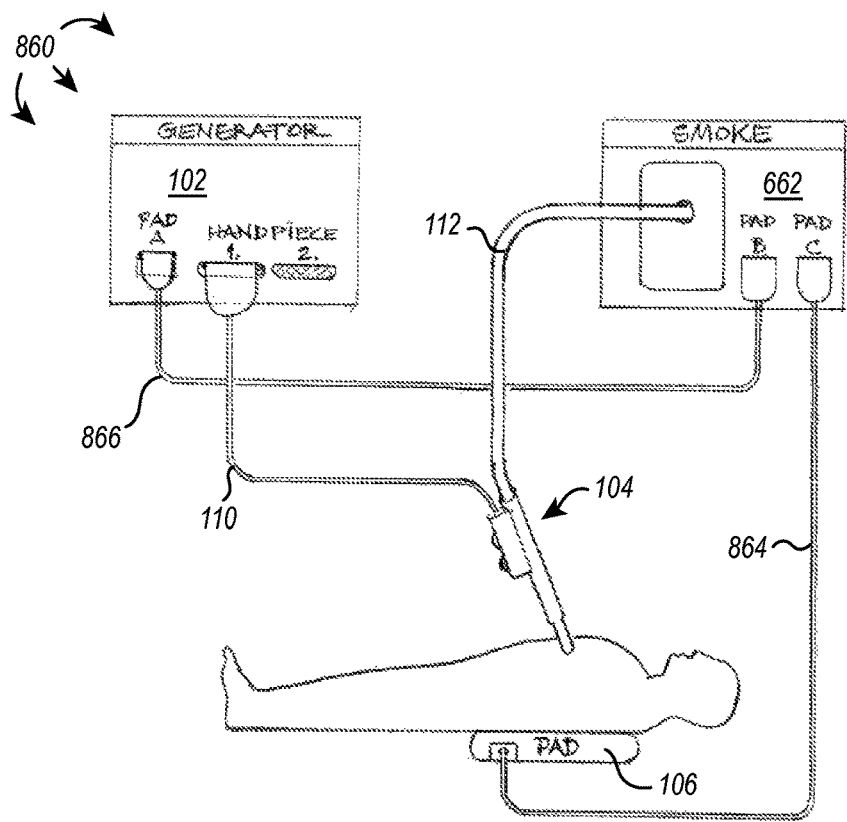
FIG. 62 illustrates a current sensor associated with the smoke evacuation device of the depicted electrosurgical system.

In some embodiments, and as illustrated in FIG. 62, a smoke evacuation device 662 can include an RF current sensor integrally formed therein. In the electrosurgical system 860 incorporating the smoke evacuation device 862, a signal generator 102 can generate an RF current and communicate the RF current to an electrosurgical instrument 104 (again illustrated as a monopolar electrosurgical instrument) through the resource cable 110. The RF current is transmitted through the patient and received at the return electrode 106 and completes the circuit to the signal generator 102 by passing through the smoke evacuation device 862 along a series of return cables 864, 866. More particularly, the RF current is passed between the return electrode 106 and the smoke evacuation device 862 via first return cable 864, and the RF current is passed between the smoke evacuation device 862 and the signal generator 102 via second return cable 866. As the RF current passes through the smoke evacuation device 862, the integrally formed RF current sensor can detect one or both of an RF activation event or RF current passing therethrough. Upon detecting activation of RF current and/or RF current passing through the smoke evacuation device 862, the integrally formed RF current sensor can communicate directly or indirectly with the vacuum system to activate and/or modulate airflow into the smoke evacuation device for a defined or dynamic period of time.

Figure 63:
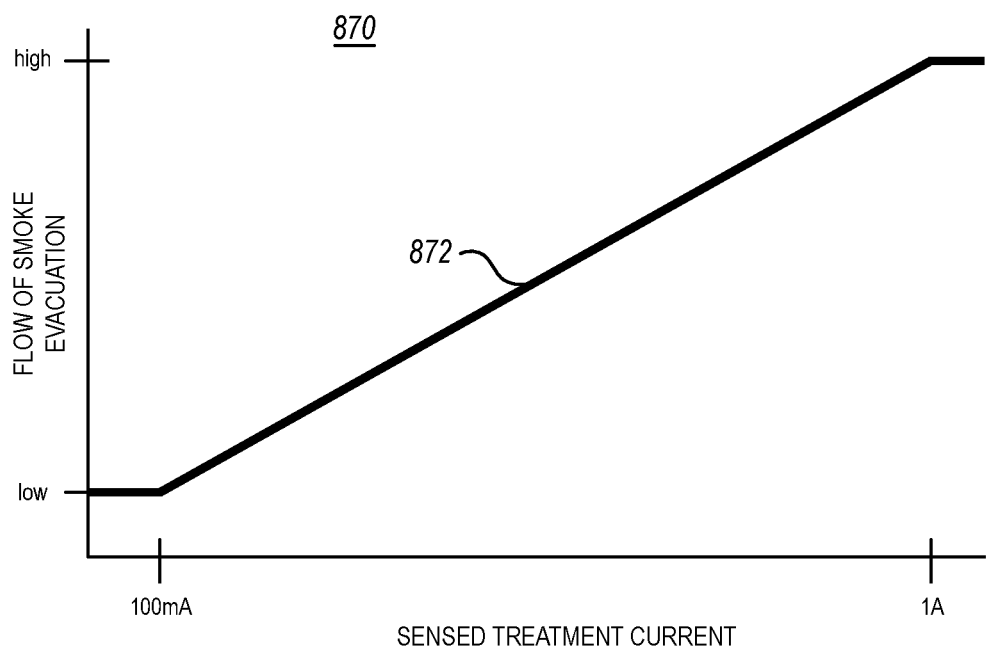
FIG. 63 illustrates an exemplary graph depicting a potential smoke evacuation flow rate with respect to the sensed treatment current from current sensors described herein.

In some embodiments, the RF current sensor can dynamically adjust the smoke evacuation flow rate in response to a sensed treatment current. For example, as shown in the graph 870 illustrated in FIG. 63, the smoke evacuation flow rate can be dynamically adjusted based on the current detected by the RF current sensor. As the current increases, the flow rate increases, and as the current decreases, the flow rate decreases.

It should be appreciated that although graph 870 illustrates a smoke evacuation curve 872 having a linear relationship between the sensed treatment current in the smoke evacuation flow rate, other relationships are possible. For example, the smoke evacuation flow rate may increase logarithmically or exponentially with respect to a sensed treatment current. In some embodiments, it may be advantageous to increase the smoke evacuation flow rate rapidly at the lower end of the sensed treatment current to ensure that any smoke generated at the surgical site has sufficient suction port extraction and conveyance to the smoke evacuation device.

In some embodiments, it may be advantageous to increase the smoke evacuation flow rate slowly at the lower end of the sensed treatment current within a rapid increase in the smoke evacuation flow rate before, at, or after the predefined treatment current or smoke generation is known to occur. In doing so, the smoke evacuation device is not activated until smoke is presumed to be generated, thereby preserving the life of the smoke evacuation device or components thereof, such as the smoke filter.

Figure 64:
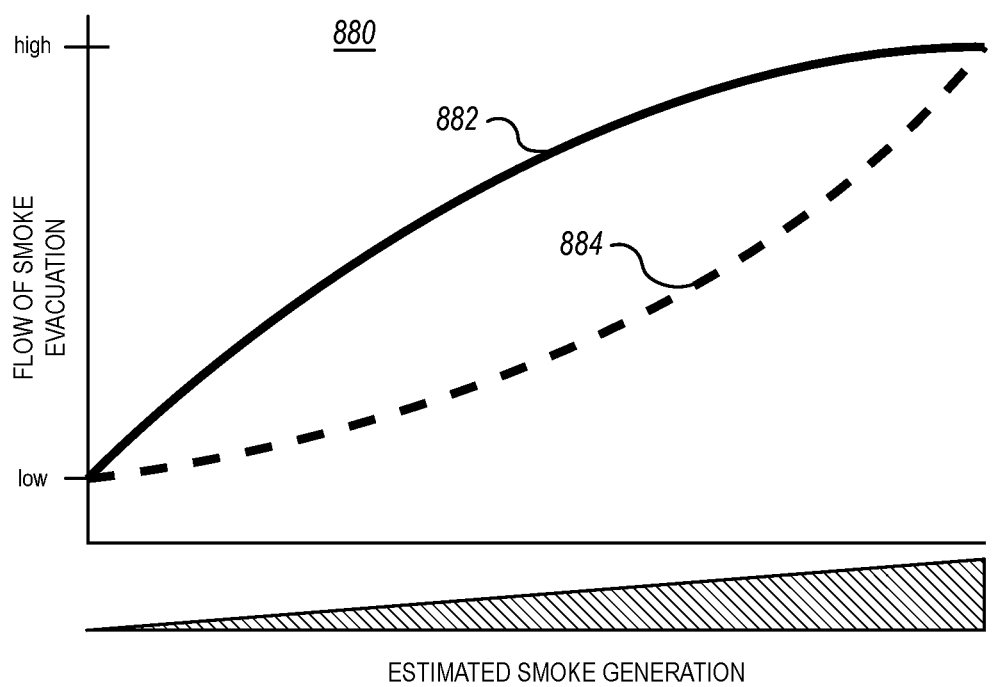
FIG. 64 illustrates an exemplary graph depicting potential smoke evacuation flow rates with respect to an estimated amount or volume of generated smoke.

In some embodiments, the detected current can be used to derive an estimate of the treatment power delivered to tissue, and in turn, the estimated treatment power delivered to tissue can be correlated with a tissue effect and the smoke generated as a result of such a tissue effect. Accordingly, in some embodiments, the detected current can be used to infer an estimated amount or volume of smoke, and that information can be used to dynamically adjust the smoke evacuation flow rate. For example, as illustrated in the graph 880 of FIG. 64, an amount or volume of estimated smoke generation can be derived based on the detected current, and the smoke evacuation flow rate can be adjusted accordingly.

In one embodiment, and as represented by the first smoke evacuation curve 882, the smoke evacuation flow rate can correlate with an estimated smoke generation in a logarithmic fashion. In another embodiment, and as represented by the second smoke evacuation curve 884, smoke evacuation flow rate can correlate with an estimated smoke generation in a polynomial or exponential fashion. In some embodiments, the smoke evacuation flow rate can correlate with an estimated smoke generation linearly (not shown).

Thus, implementations of the present disclosure enable a smoke evacuation flow rate to be dynamically modified in a way that is proportional to and/or dependent upon the current detected by the current sensor. In some embodiments, however, the direct correlation between the detected current in the smoke evacuation flow rate may not be optimal. For example, different currents may affect tissue differently and thereby cause differential smoke production that is difficult to account for when only correlating the detected current and the smoke evacuation flow rate. Furthermore, continued exposure to single or different currents may result in a smoke plume that would be unaccounted for when only correlating the detected current in the smoke evacuation flow rate.

Accordingly, implementations of the present disclosure further enable a smoke evacuation flow rate to be dynamically modified in a way that is proportional to and/or dependent upon a tissue effect and resulting smoke generation that is caused by a given treatment power. In some embodiments, the energy associated with an activation of RF current can be estimated by multiplying the treatment power by the activation time. The estimated energy can be correlated with an amount or volume of smoke produced from exposure to the estimated energy, and the smoke evacuation flow rate can be adjusted based on this amount or volume of smoke.

Similarly, the energy associated with a plurality of activations of RF current and/or energy associated with continuous RF current can be estimated by multiplying the treatment power by the activation time for each activation of RF current and/or exposure to continuous RF current. The total estimated energy can be correlated with an amount or volume of smoke produced from exposure to the total estimated energy, and the smoke evacuation flow rate can be adjusted based on this amount or volume of smoke.

While the embodiments described herein have been directed to electrosurgical instruments with smoke evacuation features, the present disclosure is not intended to be so limited. Rather, the present disclosure is broadly directed to any hand-held instrument that includes fluid (e.g., liquids, gases, vapors, smoke, or combinations thereof) evacuation or delivery features as described herein. By way of non-limiting example, such hand-held instruments may include dental instruments (e.g., drills, polishing tools, scalers, compressed air tools, suction tools, irrigation tools, carries detection tools, water flossing tool (e.g., waterpik)), soldering tools (e.g., heated tools, smoke collection tools, desoldering tools), high speed grinding and polishing tools (e.g., Dremel tools, carving tools, manicure tools, dental lab grinders/polishers), laser treatment instruments, laser surgical instruments, light probes, suction handles (e.g., Yankauer), blasting tools (e.g., sandblast, gritblast), shockwave therapy tools, ultrasonic therapy tools, ultrasonic probe tools, ultrasonic surgical tools, adhesive application instruments, glue guns, pneumatic pipettes, welding tools, RF wrinkle therapy hand pieces, phaco hand pieces, shears, shaver, or razor hand pieces, micro drill hand pieces, vacuum hand pieces, small parts handling hand pieces, tattoo needle handles, small torch hand pieces, electrology hand pieces, low speed grinding, polishing and carving tools, permanent makeup hand pieces, electrical probe hand pieces, ferromagnetic surgical hand pieces, surgical plasma hand pieces, argon beam surgical hand pieces, surgical laser hand pieces, surgical suction instruments (e.g., liposuction cannulas), surgical suction cannulas, microdermabrasion hand pieces, fiberoptic camera handles, microcamera hand pieces, pH probe hand pieces, fiberoptic and LED light source hand pieces, hydrosurgery hand pieces, orthopedic shaver, cutter, burr hand pieces, wood burning tools, electric screwdrivers, electronic pad styluses, and the like.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A smoke evacuation system, comprising:
   a housing at least partially surrounding an enclosure;
   an airflow path extending inside the enclosure from an inlet port to an outlet port of the smoke evacuation system; and
   a cooling mechanism configured to induce airflow through the enclosure to cool the enclosure, the cooling mechanism comprising:
     a first rotary element disposed within the airflow path, the first rotary element being configured to rotate when a pressurized gas flows through the airflow path; and
     a second rotary element disposed outside the airflow path and within the housing, the second rotary element being linked to the first rotary element such that rotation of the first rotary element causes the second rotary element to rotate, rotation of the second rotary element circulates air throughout the enclosure.

2. The smoke evacuation system of claim 1, further comprising a pump configured to pressurize a gas within the airflow path.

3. The smoke evacuation system of claim 2, further comprising a motor configured to power the pump.

4. The smoke evacuation system of claim 3, wherein the motor has a work output and wherein the induced airflow is proportional to the work output of the motor.

5. The smoke evacuation system of claim 1, wherein the second rotary element is linked to the first rotary element by a rotary element coupler.

6. The smoke evacuation system of claim 5, wherein the rotary element coupler comprises one or more ball bearings and wherein the rotary element coupler is disposed in-line with the airflow path so as to prevent leaking at the rotary element coupler.

7. A smoke evacuation system, comprising:
   a housing at least partially surrounding an enclosure;
   an airflow path extending inside the enclosure from an inlet port to an outlet port of the smoke evacuation system; and
   a cooling mechanism configured to induce airflow through the enclosure to cool the enclosure, the cooling mechanism comprising:
     a first rotary element disposed within the airflow path, the first rotary element being configured to rotate when a pressurized gas flows through the airflow path; and
     a second rotary element disposed outside the airflow path and within the housing, rotation of the second rotary element being configured to circulate air throughout the enclosure.

8. The smoke evacuation system of claim 7, further comprising a pump configured to pressurize a gas within the airflow path.

9. The smoke evacuation system of claim 8, further comprising a motor configured to power the pump.

10. The smoke evacuation system of claim 9, wherein the motor has a work output and wherein the induced airflow is proportional to the work output of the motor.

11. The smoke evacuation system of claim 7, wherein the first rotary element and the second rotary element are linked together such that rotation of the first rotary element causes the second rotary element to rotate.

12. The smoke evacuation system of claim 11, wherein the first and second the second rotary elements are linked together by a rotary element coupler.

13. The smoke evacuation system of claim 12, wherein the rotary element coupler comprises one or more ball bearings and wherein the rotary element coupler is disposed in-line with the airflow path so as to prevent leaking at the rotary element coupler.

14. A smoke evacuation system, comprising:
   a housing at least partially surrounding an enclosure;
   an airflow path extending inside the enclosure from an inlet port to an outlet port of the smoke evacuation system, the airflow path comprising a filter, a pump, and an exhaust mechanism; and
   a cooling mechanism configured to induce airflow through the enclosure to cool the enclosure, the cooling mechanism comprising:
     a first rotary element disposed within the airflow path, the first rotary element being configured to rotate when a pressurized gas flows through the airflow path; and
     a second rotary element linked to the first rotary element, the second rotary element being disposed outside the airflow path and within the housing, rotation of the second rotary element being configured to circulate air throughout the enclosure.

15. The smoke evacuation system of claim 14, further comprising a motor configured to power the pump.

16. The smoke evacuation system of claim 14, wherein the first rotary element and the second rotary element are linked together such that rotation of the first rotary element causes the second rotary element to rotate.

17. The smoke evacuation system of claim 16, wherein the first and second the second rotary elements are linked together by a rotary element coupler.

18. The smoke evacuation system of claim 17, wherein the rotary element coupler comprises one or more ball bearings and wherein the rotary element coupler is disposed in-line with the airflow path so as to prevent leaking at the rotary element coupler.

19. The smoke evacuation system of claim 14, wherein the exhaust mechanism comprises a cover over the outlet port, the covering being mounted on one or more resilient members.

20. The smoke evacuation system of claim 14, wherein the exhaust mechanism comprises a diffuser having a plurality of vanes that are spaced apart and angled such that the diffuser is configured to disperse the airflow in a variety of directions as the airflow exits the smoke evacuation system.

* * * * *